(12) United States Patent
Katakura et al.

(10) Patent No.: US 9,617,255 B2
(45) Date of Patent: *Apr. 11, 2017

(54) ORGANIC ELECTROLUMINESCENT ELEMENT, AND ILLUMINATION DEVICE AND DISPLAY DEVICE EACH COMPRISING THE ELEMENT

(75) Inventors: Rie Katakura, Hino (JP); Eisaku Katoh, Hachioji (JP); Hideo Taka, Inagi (JP)

(73) Assignee: KONICA MINOLTA, INC., Tokyo (JP)

(*) Notice: Subject to any disclaimer, the term of this patent is extended or adjusted under 35 U.S.C. 154(b) by 901 days.

This patent is subject to a terminal disclaimer.

(21) Appl. No.: 13/145,842

(22) PCT Filed: Jan. 21, 2010

(86) PCT No.: PCT/JP2010/050692
§ 371 (c)(1),
(2), (4) Date: Jul. 22, 2011

(87) PCT Pub. No.: WO2010/090077
PCT Pub. Date: Aug. 12, 2010

(65) Prior Publication Data
US 2011/0272687 A1 Nov. 10, 2011

(30) Foreign Application Priority Data
Feb. 6, 2009 (JP) ................ 2009-025871

(51) Int. Cl.
*H01L 51/54* (2006.01)
*C07D 471/04* (2006.01)
(Continued)

(52) U.S. Cl.
CPC ......... *C07D 471/04* (2013.01); *C07D 405/14* (2013.01); *C07D 409/14* (2013.01);
(Continued)

(58) Field of Classification Search
CPC .............. C09K 11/06; C09K 211/1029; C09K 2211/1088; C09K 2211/185; C07D 405/14;
(Continued)

(56) References Cited

U.S. PATENT DOCUMENTS 8,114,530 B2 * 2/2012 Iwakuma ............... C09K 11/06
252/301.16
8,790,793 B2 * 7/2014 Yasukawa et al. ......... 428/690
(Continued)

FOREIGN PATENT DOCUMENTS

JP 2005-112765 A 4/2005
JP 2007-126403 A 5/2007
(Continued)

OTHER PUBLICATIONS

Translation of JP 2009-021336 (publication date Jan. 2009).*
(Continued)

*Primary Examiner* — Dawn Garrett
(74) *Attorney, Agent, or Firm* — Cantor Colburn LLP

(57) ABSTRACT

Provided is an o organic electroluminescence element comprising an anode, a cathode and a plurality of composing layers including a light emitting layer sandwiched between the anode and the cathode, wherein an electron transport layer containing the compound represented by Formula (1) is included in the composing layers; the light emitting layer contains a phosphorescence emitting organic metal complex; and the cathode or one composing layer adjacent to the cathode contains a metal or a metal compound belonging to Group 1 or Group 2 of the periodic table of elements, provided that the metal exhibits a standard electrode potential larger than −3 V vs. SHE in a system of the metal ion ($M^{n+}$)/the metal (M):

(Continued)

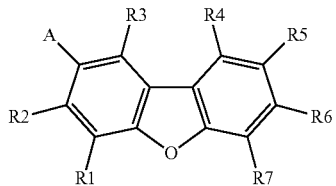

Formula (1)

16 Claims, 3 Drawing Sheets

(51) Int. Cl.
C07D 405/14 (2006.01)
C07D 409/14 (2006.01)
C07D 413/14 (2006.01)
C07D 417/14 (2006.01)
C07D 421/14 (2006.01)
C07D 495/04 (2006.01)
C07D 519/00 (2006.01)
C09K 11/06 (2006.01)
H01L 51/00 (2006.01)
H05B 33/18 (2006.01)
H05B 33/20 (2006.01)
H01L 51/50 (2006.01)

(52) U.S. Cl.
CPC ......... C07D 413/14 (2013.01); C07D 417/14 (2013.01); C07D 421/14 (2013.01); C07D 495/04 (2013.01); C07D 519/00 (2013.01); C09K 11/06 (2013.01); H01L 51/0072 (2013.01); H01L 51/0073 (2013.01); H05B 33/18 (2013.01); H05B 33/20 (2013.01); C09K 2211/1029 (2013.01); C09K 2211/1044 (2013.01); C09K 2211/1088 (2013.01); C09K 2211/1466 (2013.01); C09K 2211/185 (2013.01); H01L 51/0081 (2013.01); H01L 51/5048 (2013.01)

(58) Field of Classification Search
CPC .. C07D 413/14; C07D 495/04; C07D 421/14; C07D 409/14
See application file for complete search history.

(56) References Cited

U.S. PATENT DOCUMENTS

| 8,951,650 | B2* | 2/2015 | Yasukawa et al. | 428/690 |
| 2007/0224446 | A1* | 9/2007 | Nakano et al. | 428/690 |
| 2008/0238305 | A1 | 10/2008 | Kondo et al. | |
| 2008/0265763 | A1 | 10/2008 | Furugori et al. | |
| 2009/0017330 | A1* | 1/2009 | Iwakuma et al. | 428/690 |
| 2009/0091253 | A1* | 4/2009 | Yasukawa et al. | 313/504 |
| 2009/0167165 | A1 | 7/2009 | Otsu et al. | |
| 2010/0207105 | A1* | 8/2010 | Katakura et al. | 257/40 |

FOREIGN PATENT DOCUMENTS

| JP | 2007-180277 A | 7/2007 |
| JP | 2007-311460 A | 11/2007 |
| JP | 2008-060379 A | 3/2008 |
| JP | 2008-074939 A | 4/2008 |
| JP | 2008-270190 A | 11/2008 |
| JP | 2009-021336 A | 1/2009 |
| JP | 2009021336 A | 1/2009 |
| JP | 2009-155300 A | 7/2009 |
| JP | 2009-158848 A | 7/2009 |
| JP | 2009-263579 A | 11/2009 |
| JP | 2009-267255 A | 11/2009 |
| JP | 2010-034548 A | 2/2010 |
| WO | 2007/132886 A1 | 11/2007 |
| WO | 2007132886 A1 | 11/2007 |
| WO | 2008132965 A1 | 11/2008 |
| WO | 2008/146838 A1 | 12/2008 |
| WO | 2008146838 A1 | 12/2008 |

OTHER PUBLICATIONS

International Search Report for International Application No. PCT/JP2010/050692 mailing date of Apr. 27, 2010 with English Translation.
Extended European Search Report for Application No./Patent No. 10738415.8-2111/2395573, dated Jul. 5, 2012.
Lee, J. et al., "High efficiency organic light-emitting devices with Al/NaF cathode", Applied Physics Letters, AIP, American Institute of Physics, Melville, NY, US, vol. 82, No. 2, Jan. 13, 2003, pp. 173-175.
Shinjiro Okada et al. "Substituent effects of iridium complexes for highly efficient red OLEDs", Dalton Transactions, No. 9, Jan. 1, 2005, p. 1583.
Notice of Reasons for Refusal for Japanese Patent Application No. 2010-549426, drafted Jan. 8, 2014, with English translation.
European Office Action corresponding to Application No. 10738415.8-1354; Date of Mailing: Oct. 23, 2015.
J. Lee et al. "High efficiency organic light-emitting devices with Al/NaF cathode" Applied Physics Letters, vol. 82, No. 2, Jan. 13, 2003, pp. 173-175.
Extended European Search Report corresponding to Application No. 16157776.2-1354; Date of Mailing: May 4, 2016.
J. Lee et al.,"High Efficiency Organic Light-Emitting Devices with Al/NaF Cathode" Applied Physics Letters, vol. 82, No. 2, Jan. 13, 2003, pp. 173-175.

* cited by examiner

LIGHT

LIGHT

ORGANIC ELECTROLUMINESCENT ELEMENT, AND ILLUMINATION DEVICE AND DISPLAY DEVICE EACH COMPRISING THE ELEMENT

CROSS REFERENCE TO RELATED APPLICATIONS

This is a U.S. national stage application of International Application No. PCT/JP2010/050692, filed on 21 Jan. 2010. Priority under 35 U.S.C. 119(a) and 35 U.S.C. 365(b) is claimed from Japanese Application No. JP 2009-025871, filed 6 Feb. 2009, the disclosure of which is also incorporated herein by reference.

TECHNICAL FIELD

The present invention relates to an organic electroluminescence element, a display device and a lighting device provided with the organic electroluminescence element.

BACKGROUND

Conventionally, an emission type electronic display device includes an electroluminescence display (hereinafter, referred to as an ELD). A constituent element of an ELD includes such as an inorganic electroluminescence element and an organic electroluminescence element (hereinafter, referred to as an organic EL element). An inorganic electroluminescence element has been utilized as a flat light source, however, it requires a high voltage of alternating current to operate an emission element.

On the other hand, an organic electroluminescence element is an element provided with a constitution comprising an emitting layer containing a emitting substance being sandwiched with a cathode and an anode, and an exciton is generated by an electron and a hole being injected into the emitting layer to be recombined, resulting emission utilizing light release (fluorescence and phosphorescence) at the time of deactivation of said exciton; the emission is possible at a voltage of approximately a few to a few tens volts, and an organic electroluminescence element is attracting attention with respect to such as superior viewing angle and high visual recognition due to a self-emission type as well as space saving and portability due to a completely solid element of a thin layer type.

As an investigation of an organic EL element for practical use, an organic EL element using phosphorescent emission from an excited triplet state was reported by M. A. Baldo at al in Princeton University, Nature, vol. 395, pp 151-154 (1998). Since then, there was investigated extensively materials which exhibit phosphorescent emission at room temperature and they were reported in Nature, vol. 403, no. 17, pp 750-753 (2000) and the U.S. Pat. No. 6,097,147.

Furthermore, in the organic EL element using phosphorescence luminescence which was discovered recently, it is theoretically possible to realize about 4 times of the luminescence efficiency compared with the known element using phosphorescence luminescence. Therefore, there have been investigated throughout the world, to begin with, the material itself, the layer composition of the emitting element and the electrode.

For example, many compounds were prepared for synthetic study by S. Lamansky et al, in J. Am. Chem. Soc, vol. 123, p. 4304 (2001) focusing on heavy metal complexes, such as an iridium complex system.

Thus, although it is a method having very high potential, the organic EL element using phosphorescence luminescence has problems to be solved. It differs greatly from the organic electroluminescence element using fluorescence luminescence in the following point. The method of controlling the location of a luminescence center, especially, to perform recombination inside the light emitting layer and to emit light stably, has been an important technical investigational work from the viewpoint of improving efficiency and lifetime of the element.

Then, there is well known in recent years the element of the multilayer lamination type equipped with the hole transport layer (located in the anode side of the light emitting layer) and the electron transport layer (located in the cathode side of the light emitting layer), both transport layers each respectively adjoining the light emitting layer (for example, refer to Patent document 1).

Especially when blue phosphorescence luminescence is used, since the blue phosphorescence emitting material itself has high T1, development of peripheral materials and control of the precise luminescence center are required strongly.

In recent years, in the light emitting layer of the organic EL element using a phosphorescence emitting material, there are disclosed as follows: the technology using a dibenzothiophene derivative as a host material (for example, refer to Patent document 1); and the technology using a dibenzothiophene derivative and a dibenzofuran derivative as a hole injection ingredient and/or a luminescence ingredient (for example, refer to Patent document 2).

However, from the viewpoint of providing an organic EL element exhibiting high light emitting efficiency with low driving voltage and excellent in heat stability and raw stock stability with long lifetime, it is still insufficient and a further solution has been investigated.

On the other hand, from the requirements of larger area, lower cost and higher productivity, the expectation for a wet method (it is called a wet process etc.) is great. Since film formation can be achieved at low temperature compared with film formation with a vacuum process, the damage of an underlaying organic layer can be reduced and it attracts great expectation from the field of improvement of light emitting efficiency and lifetime of an element.

However, in the organic EL element using blue phosphorescence luminescence, in order to realize wet film forming, it has been found that the electron transport material has a problem. From a practical viewpoint, the conventionally known electron transport materials are still insufficient in respect of solution stability and driving voltage. Further technological improvement is indispensable.

PRIOR TECHNOLOGICAL DOCUMENTS

Patent Documents

Patent document 1: JP-A No. 2007-126403
Patent document 2: JP-A No. 2005-112765

SUMMARY OF THE INVENTION

Problems to be Solved by the Invention

An object of the present invention is to provide an organic EL element exhibiting high light emitting efficiency with low driving voltage and excellent in heat stability and raw stock stability with long lifetime, and also to provide a display device and a lighting device provided with the aforesaid organic electroluminescence element.

Means to Solve the Problems

An object of the present invention described above has been achieved by the following constitutions.

1. An organic electroluminescence element comprising an anode, a cathode and a plurality of composing layers including a light emitting layer sandwiched between the anode and the cathode, wherein an electron transport layer containing at least one compound represented by Formula (1) is included in the composing layers; the light emitting layer contains a phosphorescence emitting organic metal complex; and the cathode or one composing layer adjacent to the cathode contains a metal or a metal compound belonging to Group 1 or Group 2 of the periodic table of elements, provided that the metal exhibits a standard electrode potential larger than −3 V vs. SHE in a system of the metal ion ($M^{n+}$)/the metal (M).

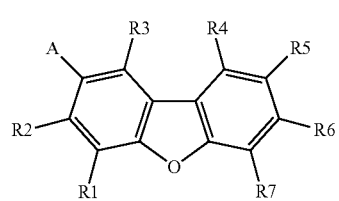

Formula (1)

(In Formula, R1 to R7 each represent a hydrogen atom or a substituent. "A" represents a phenyl group or an aromatic heterocyclic group, provided that "A" contains at least one of a carbazole ring, an azacarbazole ring, a dibenzofuran ring and a dibenzothiophene ring as a partial structure.)

2. The organic electroluminescence element of the aforesaid item 1, wherein the compound represented by Formula (1) is a compound represented by Formula (2).

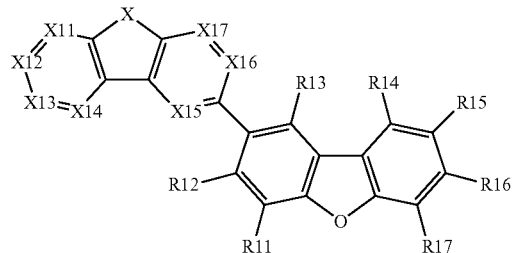

Formula (2)

(In Formula, R11 to R17 each represent a hydrogen atom or a substituent, X represents —O—, —S—, or —N(R10)-, and R10 represents a hydrogen atom or a substituent. X11 to X17 represents —C(R18)=, or —N=, and R18 represents a hydrogen atom or a substituent. When a plurality of —C(R18)= exists, a plurality of R18s may be the same or different, provided that at least one of R10 to R18 represents a substituent.)

3. The organic electroluminescence element of the aforesaid item 2, wherein X in Formula (2) represents —N(R10)-; R11 to R14, R16 and R17 each represent a hydrogen atom; and X11, X12 and X14 to X17 each represent —CH= or —N=.

4. The organic electroluminescence element of the aforesaid item 2, wherein X in Formula (2) represents —O— or —S—; R11 to R14, R16 and R17 each represent a hydrogen atom; and X11, X12 and X14 to X17 each represent —CH=.

5. The organic electroluminescence element of the aforesaid item 1, wherein the compound represented by Formula (1) is a compound represented by Formula (3).

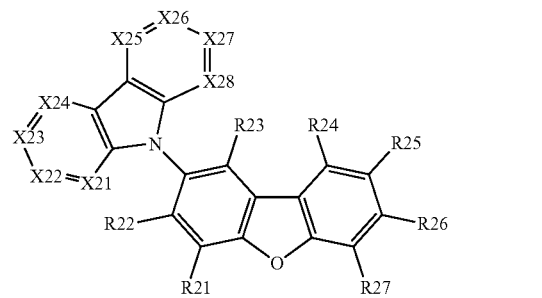

Formula (3)

(In Formula, R21 to R27 each represent a hydrogen atom or a substituent, X21 to X28 each represents —C(R28)=, or —N=, and R28 represents a hydrogen atom or a substituent. When a plurality of —C(R28)= exists, a plurality of R28s may be the same or different, provided that at least one of R21 to R28 represents a substituent.)

6. The organic electroluminescence element of the aforesaid item 5, wherein R21 to R24, R26 and R27 in Formula (3) each represent a hydrogen atom; and X21, X22, X24, X25, X27 and X28 each represent —CH= or —N=.

7. The organic electroluminescence element of the aforesaid item 1, wherein the compound represented by Formula (1) is a compound represented by Formula (4).

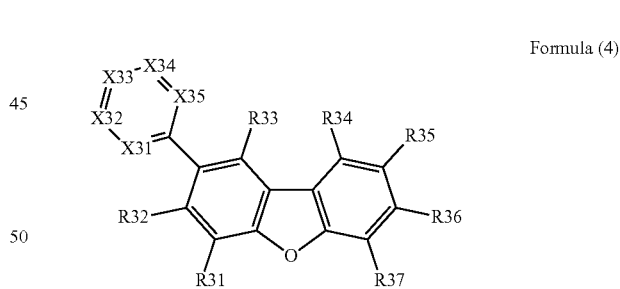

Formula (4)

(In Formula, R31 to R37 each represent a hydrogen atom or a substituent. X31 to X35 each represents —C(R38)=, or —N=, and R38 represents a hydrogen atom or a substituent. Provided that at least one of X31 to X35 represents —C(R38)= in which R38 represents a substituent. When a plurality of —C(R38)= exists, a plurality of R38s may be the same or different.)

8. The organic electroluminescence element of the aforesaid item 7, wherein R31 to R34, R36 and R37 in Formula (4) each represent a hydrogen atom; and X33 represents —CH=, or —N=.

9. The organic electroluminescence element of any one of the aforesaid items 1 to 8, wherein the compound represented by any one of Formulas (1) to (4) contains as a partial structure at least one pyridine ring or one condensed aromatic heterocycle containing a pyridine ring.

10. The organic electroluminescence element of any one of the aforesaid items 1 to 9,
wherein the metal element is sodium, potassium or cesium.

11. The organic electroluminescence element of any one of the aforesaid items 1 to 10,
wherein the phosphorescence emitting organic metal complex is a compound represented by Formula (5).

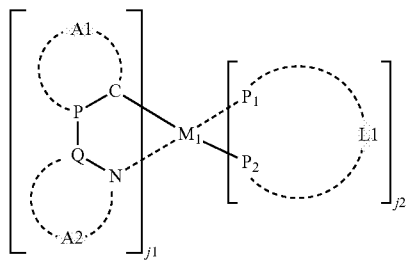

Formula (5)

[In Formula, P and Q each represent a carbon atom or a nitrogen atom, and A1 represents a group of atoms necessary to form an aromatic hydrocarbon ring or an aromatic heterocycle together with P—C. A2 represents a group of atoms necessary to form an aromatic heterocycle together with Q-N. $P_1$-L1-$P_2$ represents a bidentate ligand, and $P_1$ and $P_2$ each independently represent a carbon atom, a nitrogen atom, or an oxygen atom. L1 represents a group of atoms necessary to form a bidentate ligand together with $P_1$ and $P_2$. j1 is an integer of 1 to 3, and j2 is an integer of 0 to 2, provided that the sum of j1 and j2 is 2 or 3. $M_1$ represents a metal element of Group 8 to Group 10 in the periodic table.]

12. The organic electroluminescence element of the aforesaid item 11,
wherein the compound represented by Formula (5) is a compound represented by Formula (6).

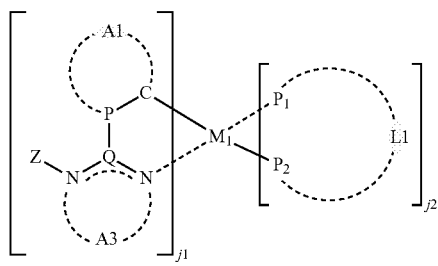

Formula (6)

[In Formula, Z represents a hydrocarbon ring group or a heterocyclic group. P and Q each represent a carbon atom or a nitrogen atom, and A1 represents a group of atoms necessary to form an aromatic hydrocarbon ring or an aromatic heterocycle together with P—C. A3 represents —C($R_{O1}$)═C($R_{O2}$)—, —N═C($R_{O2}$)—, —C($R_{O1}$)═N—, or —N═N—, and $R_{O1}$ and $R_{O2}$ each represent a hydrogen atom or a substituent. $P_1$-L1-$P_2$ represents a bidentate ligand, and $P_1$ and $P_2$ each independently represent a carbon atom, a nitrogen atom, or an oxygen atom. L1 represents a group of atoms necessary to form a bidentate ligand together with $P_1$ and $P_2$. j1 is an integer of 1 to 3, and j2 is an integer of 0 to 2, provided that the sum of j1 and j2 is 2 or 3. $M_1$ represents a transition metal element of Group 8 to Group 10 in the periodic table.]

13. The organic electroluminescence element of the aforesaid item 12,
wherein the compound represented by Formula (6) is a compound represented by Formula (7).

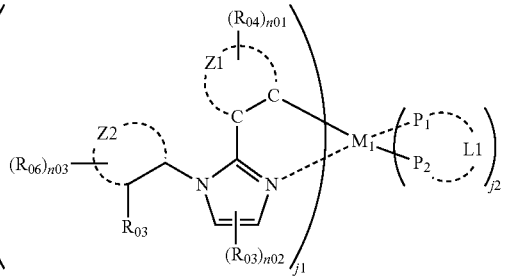

Formula (7)

[In Formula, $R_{O3}$ represents a substituent, $R_{O4}$ represents a hydrogen atom or a substituent, and a plurality of $R_{O4}$s may be joined together to form a ring. n01 is an integer of 1 to 4. $R_{O5}$ represents a hydrogen atom or a substituent, and a plurality of $R_{O5}$s may be joined together to form a ring. n02 is an integer of 1 to 2. $R_{O6}$ represents a hydrogen atom or a substituent, and a plurality of $R_{O6}$s may be joined together to form a ring. n03 is an integer of 1 to 4. Z1 represents a group of atoms necessary to form a 6-membered aromatic hydrocarbon ring, or a 5 or 6-membered aromatic heterocycle together with C—C. Z2 represents a group of atoms necessary to form a hydrocarbon ring or a heterocycle. $P_1$-L1-$P_2$ represents a bidentate ligand, and $P_1$ and $P_2$ each independently represent a carbon atom, a nitrogen atom, or an oxygen atom. L1 represents a group of atoms necessary to form a bidentate ligand together with $P_1$ and $P_2$. j1 is an integer of 1 to 3, and j2 is an integer of 0 to 2, provided that the sum of j1 and j2 is 2 or 3. $M_1$ represents a transition metal element of Group 8 to Group 10 in the periodic table. $R_{O3}$ and $R_{O6}$, $R_{O4}$ and $R_{O6}$, and $R_{O5}$ and R06 may be joined together to form a ring.]

14. The organic electroluminescence element of the aforesaid item 13,
wherein the compound represented by Formula (7) is a compound represented by Formula (8).

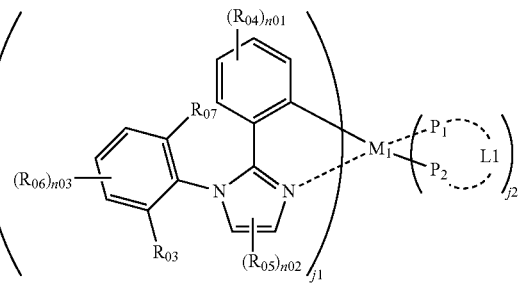

Formula (8)

[In Formula, $R_{O3}$ represents a substituent, $R_{O4}$ represents a hydrogen atom or a substituent, and a plurality of $R_{O4}$s may be joined together to form a ring. n01 is an integer of 1 to 4. $R_{05}$ represents a hydrogen atom or a substituent, and a plurality of $R_{05}$s may be joined together to form a ring. n02 is an integer of 1 to 2. $R_{06}$ represents a hydrogen atom or a substituent, and a plurality of $R_{06}$s may be joined together to form a ring. n03 is an integer of 1 to 3. $R_{07}$ represents a substituent or a single bond. $P_1$-L1-$P_2$ represents a bidentate ligand, and $P_1$ and $P_2$ each independently represent a carbon atom, a nitrogen atom, or an oxygen atom. L1 represents a group of atoms necessary to form a bidentate ligand together with $P_1$ and $P_2$. j1 is an integer of 1 to 3, and j2 is an integer of 0 to 2, provided that the sum of j1 and j2 is 2 or 3. $M_1$ represents a transition metal element of Group 8 to Group 10 in the periodic table.]

15. The organic electroluminescence element of any one of the aforesaid items 11 to 14,
    wherein $M_1$ represents iridium.
16. The organic electroluminescence element of any one of the aforesaid items 1 to 15,
    wherein at least two organic layers including the electron transport layer and the light emitting layer are formed with a wet method.
17. The organic electroluminescence element of any one of the aforesaid items 1 to 16,
    wherein the organic electroluminescence element emits a white light.
18. A lighting device comprising the organic electroluminescence element of any one of the aforesaid items 1 to 16.
19. A display device comprising the organic electroluminescence element of any one of the aforesaid items 1 to 16.

Effects of the Invention

By the present invention, it has been achieved to provide an organic electroluminescent element which has high emission efficiency with low driving voltage and excellent in heat resistance and raw stock stability, and has a long emission lifetime.

It has been achieved to provide a display device and a lighting device provided with the aforesaid organic EL element.

EMBODIMENTS TO CARRY OUT THE INVENTION

Figure 1:
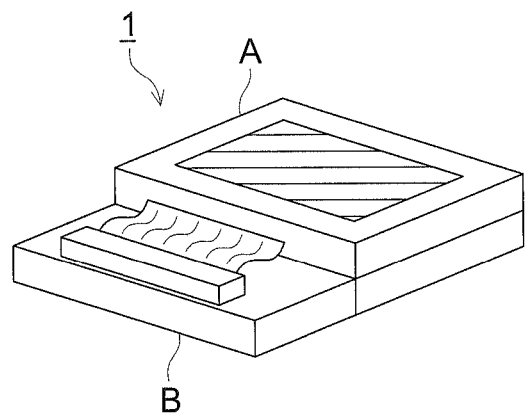
FIG. 1 is a schematic drawing to show an example of a display device constituted of an organic EL element.

In the organic EL element of the present invention, it has been achieved to provide an organic EL element exhibiting high light emitting efficiency with low driving voltage and excellent in heat stability and raw stock stability with long lifetime by forming any one of the structures described in claims 1 to 17.

It has also been achieved to provide a display device and a lighting device equipped with the above-described organic EL element.

Hereafter, the details of each structural element of the organic EL element of the present invention will be described successively.

In order to attain the above-mentioned object, the present inventors have continued investigation wholeheartedly. As a result, it was found out that an efficient and long-life organic electroluminescence element was obtained by using an electron transportation layer incorporating a compound represented with Formula (1).

Moreover, a dibenzofuran ring has high flatness and it became possible to provide a material with a high glass transition temperature (Tg) by using the dibenzofuran ring for a core skeleton. Although a carbazole ring and a fluorene ring are an aromatic ring having a similar skeleton to a dibenzofuran ring, the NH portion at the 9th place of a carbazole ring and the $CH_2$ portion at the 9th place of a fluorene ring have highly reactive and unstable. Therefore, although it is necessary to substitute the 9th place, flatness will be collapsed by introducing a substituent at that place.

On the other hand, there is no activity as described above in a dibenzofuran ring. Therefore, it is not required to introduce a substituent at the similar place to the NH portion at the 9th place of a carbazole ring and the $CH_2$ portion at the 9th place of a fluorene ring. And it is possible to maintain flatness in the dibenzofuran ring. As a result, it becomes possible to form a dense thin film, and the stability of membrane will be increased, and storage property will be also improved.

Moreover, the oxygen atom belonging to the 2nd period of the periodic table of the elements takes a charge state more unstable than the sulfur atom belonging to the 3rd period. Therefore, it was found out that a dibenzofuran derivative like the compound represented by Formula (1) of the present invention which contains an oxygen atom as a composition atom tends to pass an electron easily, as a result, it becomes easy for a carrier to move, and low driving voltage can be attained.

Furthermore, the substitution location A in Formula (1) will not lengthen the conjugate length, and it is the place which can be connected with other skeleton while keeping high triplet energy level (T1). Further, since synthetic introduction of a substituent is easier than the 4th place of a dibenzofuran ring, it is suitable for mass production nature.

Moreover, the alkali metal and the alkaline earth metal which are represented by lithium fluoride having a small work function are well known as an electron injection material. The present inventors examined in details about combination with the electron transport material of the present invention. It was found out that an organic EL element can be driven efficiently and at the same time, with low driving voltage by using together a metal or a metal compound (including a complex and a salt) belonging to Group 1 or Group 2 of the periodic table of elements and whose normal electrode potential is larger than −3 V vs. SEE in a system of $M^{n+}/M$.

The element having a large redox potential tends to easily receive an electron compared with the element having a small redox potential. The element having a large redox potential will easily be reduced to become in a metal state, as a result, an electron from the cathode will be easily transported through a metal to the electron transport layer. It became possible to provide an organic EL element of high efficiency with low driving voltage by using a combination of a dibenzofuran derivative of the present invention with an electron injection material.

In addition, an anode, a cathode, and a plurality of composing layers (the organic layers such as a hole injection layer, a hole transport layer, a light emitting layer, an electron transport layer, and an electron injection layer) sandwiched between the anode, all of which compose the organic EL element, will be described later in details.

The compounds represented by Formula (1) will be described below.

<<Compounds Represented by Formula (1)>>

Examples of a substituent represented by each of R1 to R7 in Formula (1) include: an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group); a cycloalkyl group (for example, a cyclopentyl group, and a cyclohexyl group); an alkenyl group (for example, a vinyl group and an allyl group); an alkynyl group (for example, an ethynyl group and a propargyl group); an aromatic hydrocarbon ring group (also called an aromatic carbon ring or an aryl group, for example, a phenyl group, a p-chlorophenyl group, a mesityl group, a tolyl group, a xylyl group, a naphthyl group, an anthryl group, an azulenyl group, an acenaphthenyl group, a fluorenyl group, a phenantolyl group, an indenyl group, a pyrenyl group, and a biphenyryl group); an aromatic heterocyclic group (for example, a pyridyl group, a pyrimidinyl group, a furyl group, a pyrrolyl group, an imidazolyl group, a benzoimidazolyl group, a pyrazolyl group, a pyradinyl group, a triazolyl group (for example, 1,2,4-triazole-1-yl group and 1,2,3-triazole-1-yl group), an oxazolyl group, a benzoxazolyl group, a thiazolyl group, an isooxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, a carbolinyl group, a diazacarbazolyl group (indicating a ring structure in which one of the carbon atoms constituting the carboline ring in the aforesaid carbolinyl group is replaced with a nitrogen atom), a quinoxalinyl group, a pyridazinyl group, a triazinyl group, a quinazolinyl group, and a phthalazinyl group), a quinoxalinyl group, a pyridazinyl group, a triazinyl group, a quinazolinyl group, a phthalazinyl group); a heterocyclic group (for example, a pyrrolidyl group, an imidazolidyl group, a morpholyl group, and an oxazolidyl group); an alkoxyl group (for example, a methoxy group, an ethoxy group, a propyloxy group, a pentyloxy group, an hexyloxy group, an octyloxy group, and a dodecyloxy group); a cycloalkoxy group (for example, a cyclopentyloxy group and a cyclohexyloxy group); an aryloxy group (for example, a phenoxy group and a naphthyloxy group); an alkylthio group (for example, a methylthio group, an ethylthio group, a propylthio group, a pentylthio group, a hexylthio group, an octylthio group, and a dodecylthio group); a cycloalkylthio group (for example, a cyclopentylthio group and a cyclohexylthio group); an arylthio group (for example, a phenylthio group and a naphthylthio group); an alkoxycarbonyl group (for example, a methyloxycarbonyl group, an ethyloxycarbonyl group, a butyloxycarbonyl group, an octyloxycarbonyl group, and a dodecyloxycarbonyl group); an aryloxycarbonyl group (for example, a phenyloxycarbonyl group and a naphthyloxycarbonyl group); a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphmylaminosulfonyl group, and a 2-pyridylaminosulfonyl group); an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, and a pyridylcarbonyl group); an acyloxy group (for example, an acetyloxy group, an ethylcarbonyloxy group, a butylcarbonyloxy group, an octylcarbonyloxy group, a dodecylcarbonyloxy group, and a phenylcarbonyloxy group); an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, and a naphthylcarbonylamino group); a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, and a 2-pyridylaminocarbonyl group); a ureido group (for example, a methylureido group, an ethylureido group, a pentylureido group, a cyclohexylureido group, an octylureido group, a dodecylureido group, a phenylureido group, a naphthylureido group, and a 2-oyridylaminoureido group); a sulfinyl group (for example, a methylsulfinyl group, an ethylsulfinyl group, a butylsulfinyl group, a cyclohexylsulfinyl group, a 2-ethylhexylsulfinyl group, a dodecylsulfinyl group, a phenylsulfinyl group, a naphthylsulfinyl group, and a 2-pyridylsulfinyl group); an alkylsulfonyl group (for example, a methylsulfonyl group, an ethylsulfonyl group, a butylsulfinyl group, a cyclohexylsulfonyl group, a 2-ethylhexylsulfonyl group, and a dodecylsulfonyl group, an arylsulfonyl group or a heteroarylsulfonyl group (for example, a phenylsulfonyl group, a naphthylsulfonyl group, and a 2-pyridylsulfonyl group); an amino group (for example, an amino group, an ethylamino group, a dimethylamino group, a butylamino group, a cyclopentylamino group, a dodecylamino group, an anilino group, a naphthylamino group, and a 2-pyridylamino group); a cyano group; a nitro group; a hydroxyl group; a mercapto group; a silyl group (for example, a trimethylsilyl group, a triisopropylsilyl group, a triphenylsilyl group, and a phenyldiethylsilyl group) and a phosphono group.

Moreover, these substituents may be further substituted by the above-mentioned substituent. Further, a plurality of these substituents may combine with each other to form a ring.

In Formula (1), a phenyl group represented by "A" contains at least one of carbazole ring, azacarbazole ring, dibenzofuran ring and a dibenzothiohene ring as a partial structure.

Here, "an azacarbazole ring" indicates a ring structure in which one or plural carbon atoms in the benzene ring constituting the aforesaid carbazole ring is replaced with one or plural nitrogen atoms. These rings may further have a substituent.

The aforesaid partial structure may be unsubstituted or may have a substituent. This substituent is synonymous with the substituent represented by R1 to R7 each in Formula (1).

Examples of an aromatic heterocyclic group represented by "A" in Formula (1) include: a pyridyl group, a pyrimidinyl group, a furyl group, a pyrrolyl group, an imidazolyl group, a benzoimidazolyl group, a pyrazolyl group, a pyradinyl group, a triazolyl group (for example, 1,2,4-triazole-1-yl group and 1,2,3-triazole-1-yl group), an oxazolyl group, a benzoxazolyl group, a thiazolyl group, an isooxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, a carbolinyl group, a diazacarbazolyl group (indicating a ring structure in which one of the carbon atoms constituting the carboline ring in the aforesaid carbolinyl group is replaced with a nitrogen atom), a quinoxalinyl group, a pyridazinyl group, a triazinyl group, a quinazolinyl group, and a phthalazinyl group. These groups may be unsubstituted or may have a substituent represented by each of R1 to R7 in Formula (1).

Further, the aforesaid aromatic heterocyclic group contains at least one of carbazole ring, azacarbazole ring, dibenzofuran ring and dibenzothiophene ring as a partial structure.

One of the preferable embodiments of the compounds represented by Formula (1) of the present invention is the compound represented by any one of the above-described Formulas (2), (3) and (4).

<<Compounds Represented by Formula (2)>>

In Formula (2), the substituents represented by R11 to R17 each are synonymous with the substituents represented by R1 to R7 each in Formula (1).

In —N(R10)- represented by X of Formula (2), the substituent represented by R10 is synonymous with the substituent represented by R1 to R7 each in Formula (1).

In X11 to X17 of Formula (2), the substituent represented by R18 in —C(R18)= is synonymous with the substituent represented by R1 to R7 each in Formula (1).

Further, among the compounds represented by Formula (2), preferable embodiments are the following (a) and (b).
(a) X of Formula (2) represents —N(R10)-; R11 to R14, R16 and R17 each represent a hydrogen atom; and X11, X12, X14 to X17 each represent —CH= or —N=.
(b) X of Formula (2) represents —O—, or —S—; R11 to R14, R16 and R17 each represent a hydrogen atom; and X11, X12, X14 to X17 each represent —CH=.

<<Compounds Represented by Formula (3)>>

In Formula (3), the substituents represented by R21 to R27 each are synonymous with the substituents represented by R1 to R7 each in Formula (1).

In X21 to X27 of Formula (3), the substituent represented by R28 in —C(R28)= is synonymous with the substituent represented by R1 to R7 each in Formula (1).

Further, among the compounds represented by Formula (3), preferable embodiments is the following (c).
(c) R21 to R24, R26 and R27 in Formula (3) each represent a hydrogen atom; and X21, X22, X24, X25, X27, and X28 each represent —CH=, or —N=.

<<Compounds Represented by Formula (4)>>

In Formula (4), the substituents represented by R31 to R37 each are synonymous with the substituents represented by R1 to R7 each in Formula (1).

In X31 to X37 of Formula (3), the substituent represented by R38 in —C(R38)= is synonymous with the substituent represented by R1 to R7 each in Formula (1).

Further, among the compounds represented by Formula (4), preferable embodiments is the following (d).
(d) R31 to R34, R36 and R37 in Formula (4) each represent a hydrogen atom; and X33 represents —CH=, or —N=.

Hereafter, more preferable embodiments of the compound represented by any one of Formulas (1), (2), (3) and (4) of the present invention will be described below.

<<Preferable Partial Structure>>

As a preferable embodiment of the compound represented by any one of Formulas (1), (2), (3) and (4) of the present invention is a compound having at least one pyridine ring or one condensed aromatic heterocycle containing the pyridine ring as a partial structure.

Here, "a condensed aromatic heterocycle containing the pyridine ring" indicates a condensed aromatic heterocycle such as β-carboline in which at least one of the rings composing the condensed ring is a pyridine ring.

<<Tg (Glass Transition Temperature, ° C.)>>

In order to increase the glass transition temperature of compound represented by any one of Formulas (1), (2), (3) and (4) of the present invention, it is efficient to incorporate a condensed ring such as a naphthalene ring or an anthracene ring in the compound.

However, an aromatic hydrocarbon ring of a condensed type will exhibits a small T1 (indicating an excited triplet state), and it is not suitable especially when it is used in combination with a blue phosphorescence dopant.

Then, it is desirable to introduce a condensed aromatic heterocycle such as a carbazole ring or a dibenzofuran ring, as a means for increasing Tg without lowering T1.

<<Preferably Incorporated Composing Layers and Preparation Method of the Preferably Incorporated Composing Layers>>

Although the compound represented by any one of Formulas (1), (2), (3) and (4) of the present invention is incorporated at least in an electron transport layer, it may be incorporated in other layer than an electron transport layer such as in a hole transport layer or in a light emitting layer.

As a preparation method for the compound represented by any one of Formulas (1), (2), (3) and (4) of the present invention, although there are a wet method (it is also called as a wet process) and a vacuum deposition method, a wet method is preferably used from the viewpoint of easily obtaining a homogeneous membrane and of being hard to generate a pinhole.

Here, examples of a wet process include: a spin coating method, a cast method, a die coating method, a blade coating method, a roll coating method, an inkjet method, a printing method, a spray coating method, and a curtain coating method. From the viewpoint of enabling to form a precise thin layer with a high productivity, a die coating method, a roll coating method, an inkjet method and a spray coating method are preferably used. These methods are suitable for applying to a roll to roll production method. It may be possible to use a different film production method for every layer.

When the composing layers are formed using a coating method (including a dispersion method) with the compound represented by any one of Formulas (1), (2), (3) and (4) of the present invention, although there is no limitation of solvents in particular, it is preferable that Tg of the above-described compound and the boiling point Tb of the solvent will satisfy the following Scheme (1).

$$Tg+10° C. \geq Tb \qquad \text{Scheme (1)}$$

Moreover, it is preferable that three or more organic layers which constitute the organic EL element of the present invention are produced by coating, and further, the cathode may also be formed by coating using silver nano particles.

Although specific examples of the compound represented by any one of Formulas (1), (2), (3) and (4) of the present invention will be shown in below, the present invention will not be limited to them.

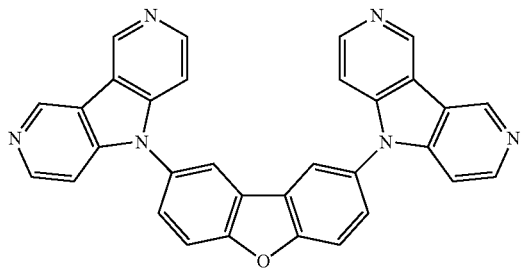
1
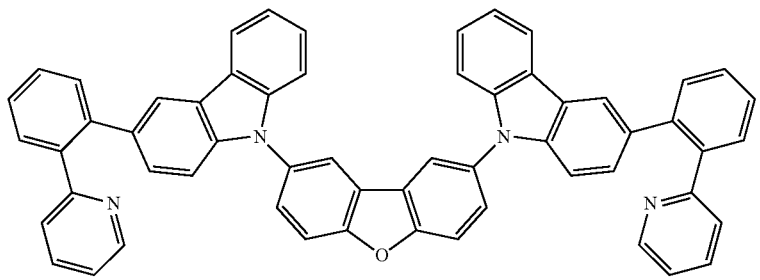
2
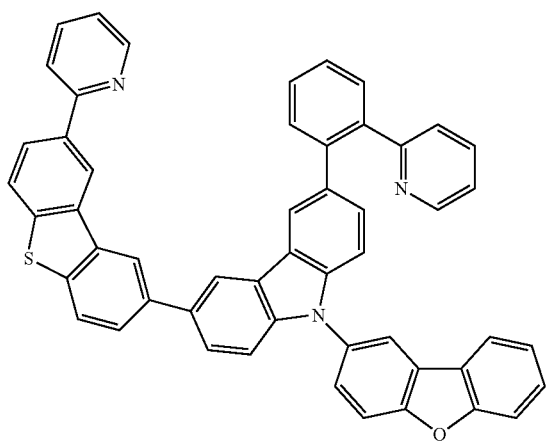
3
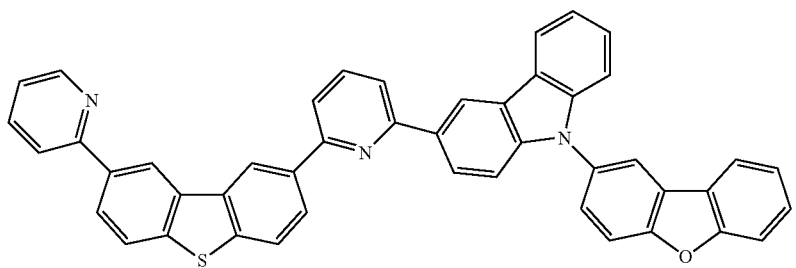
4
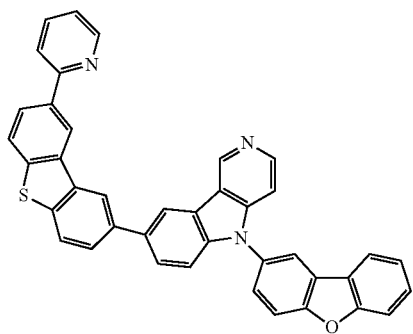
5
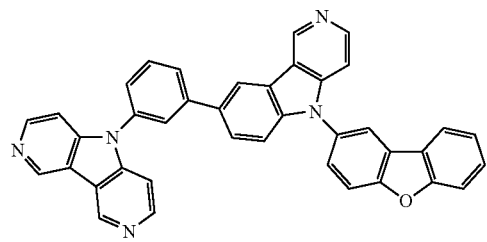
6

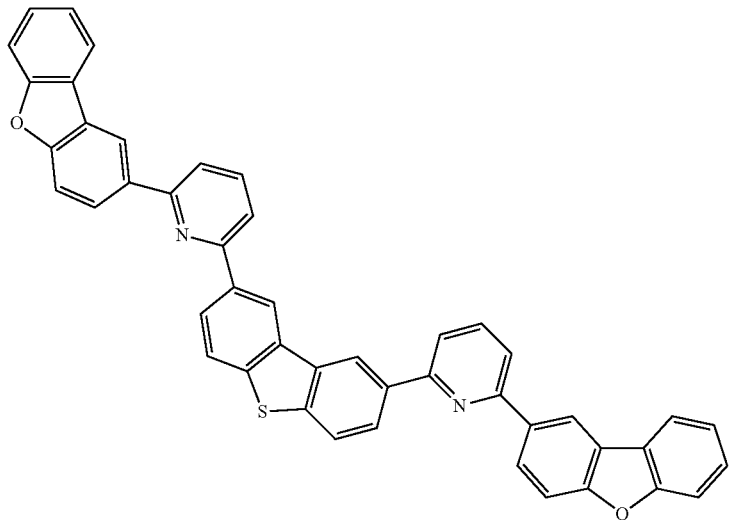
7
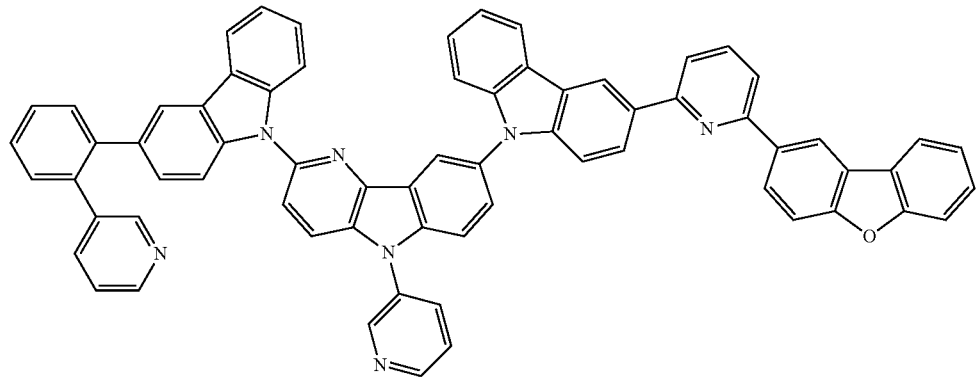
8
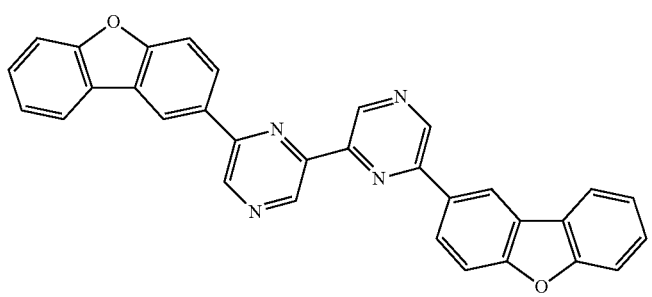
9
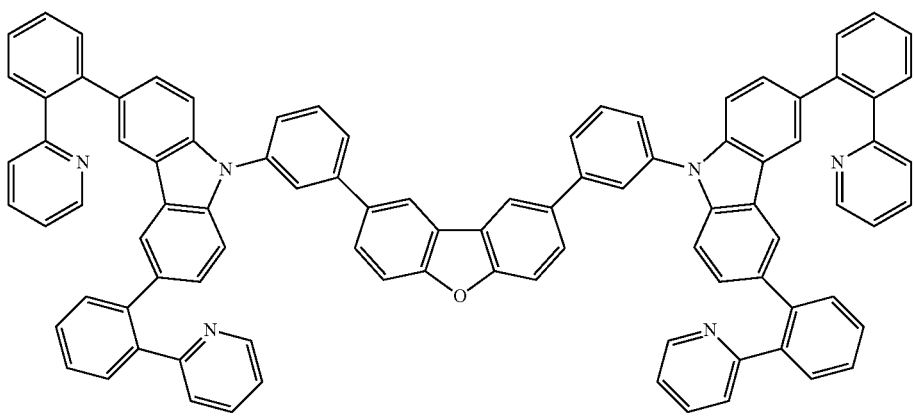
10

-continued
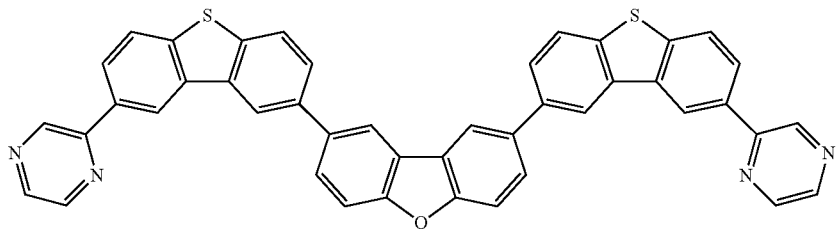
11
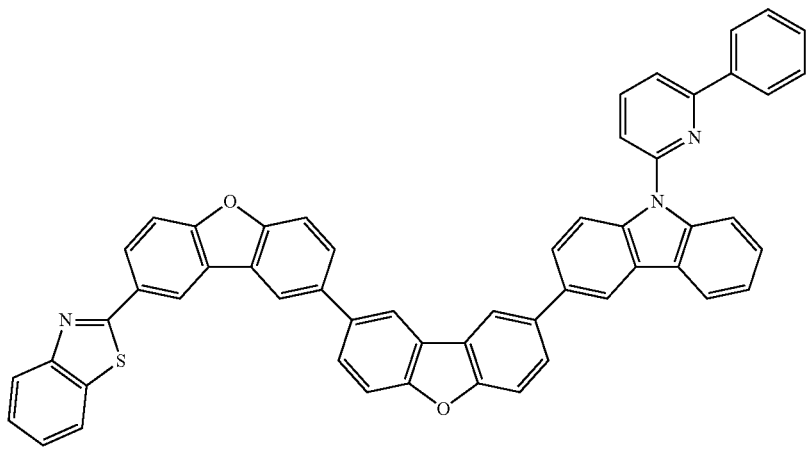
12
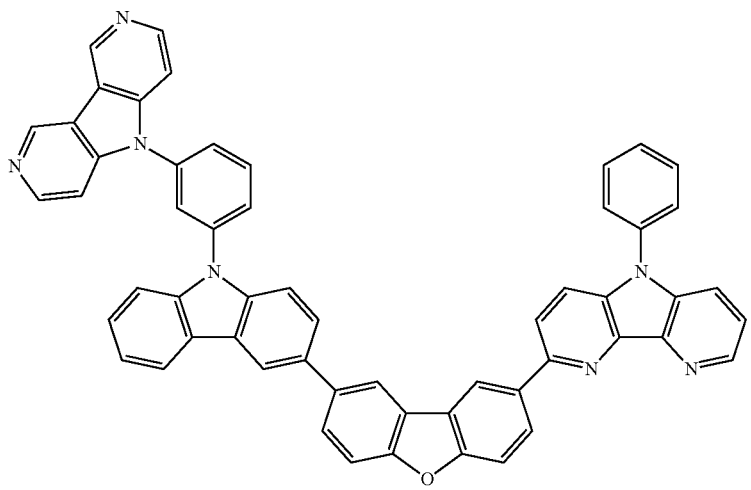
13
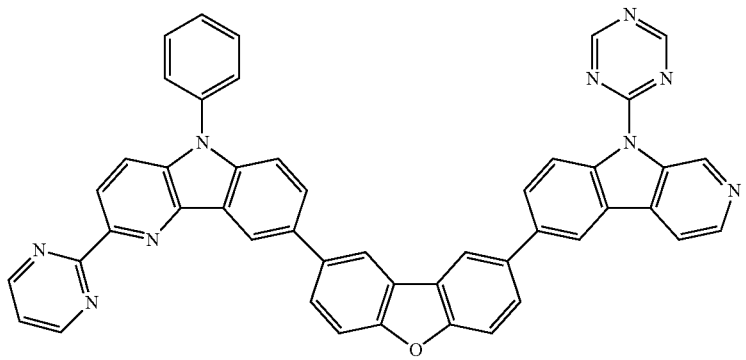
14

15
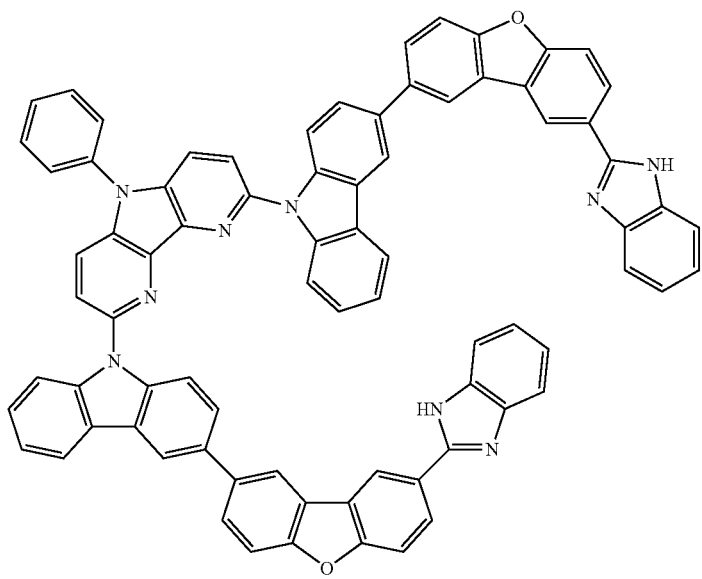
16
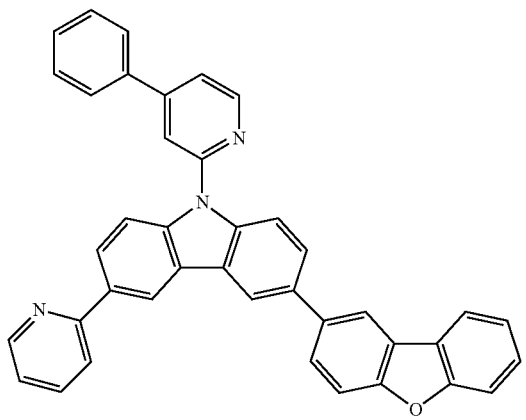
17
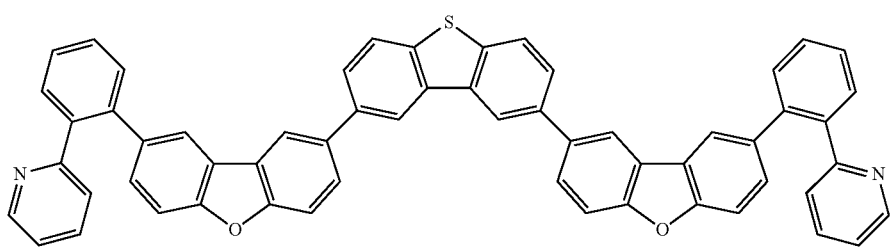

-continued
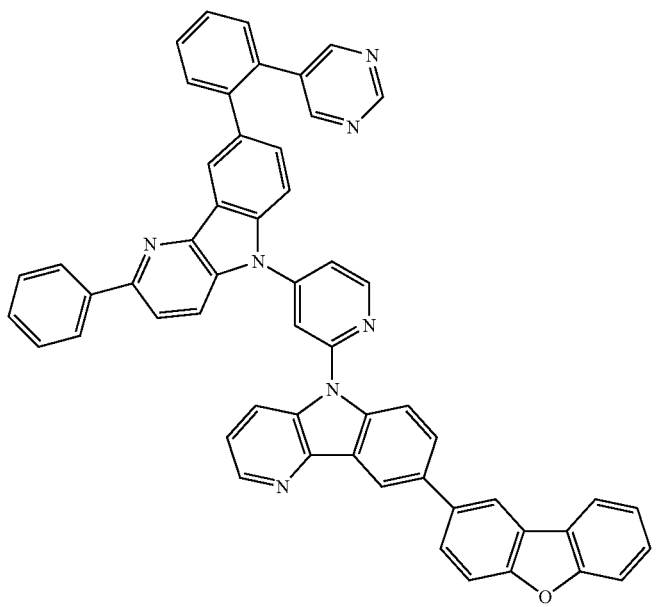
18
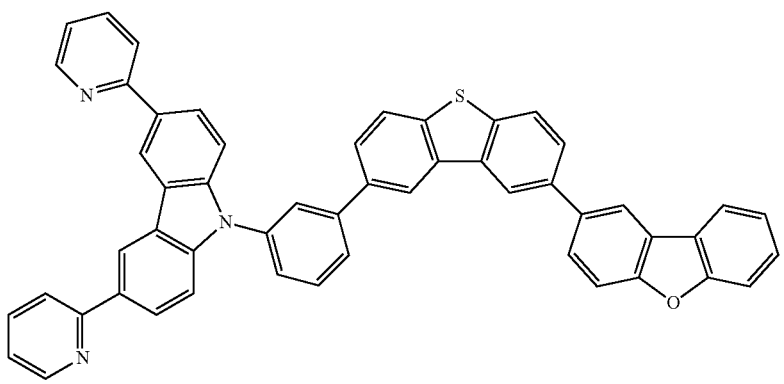
19
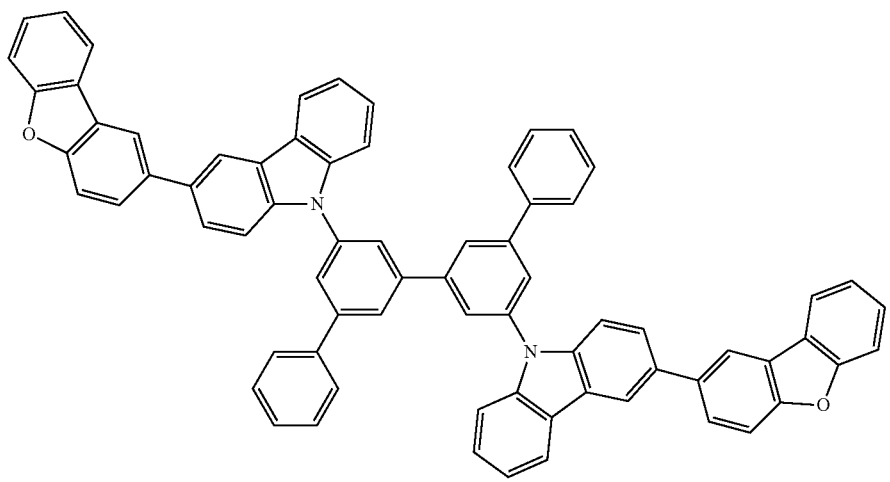
20

21
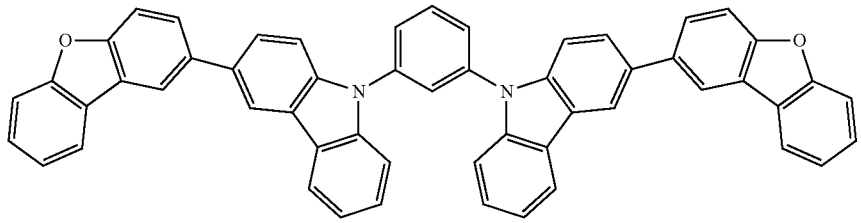
22
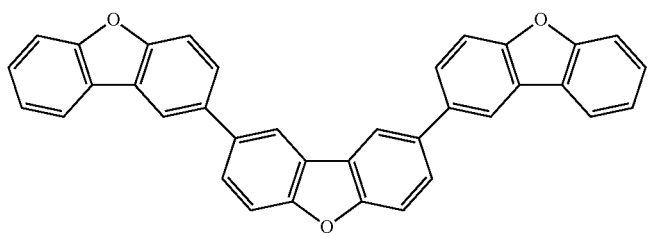
23
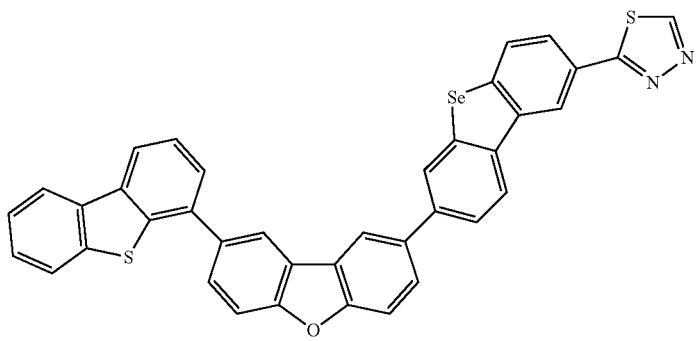
24
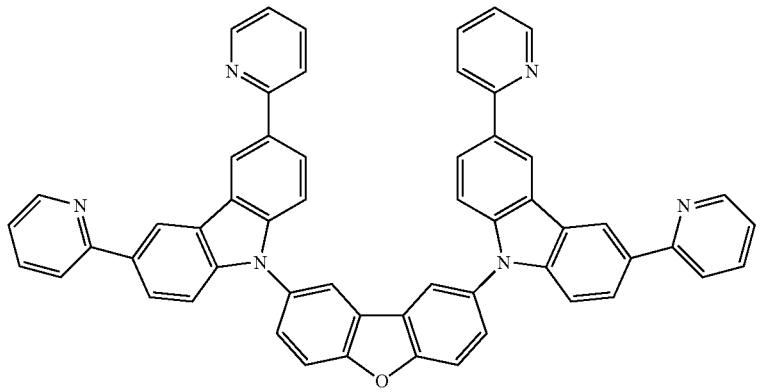
25
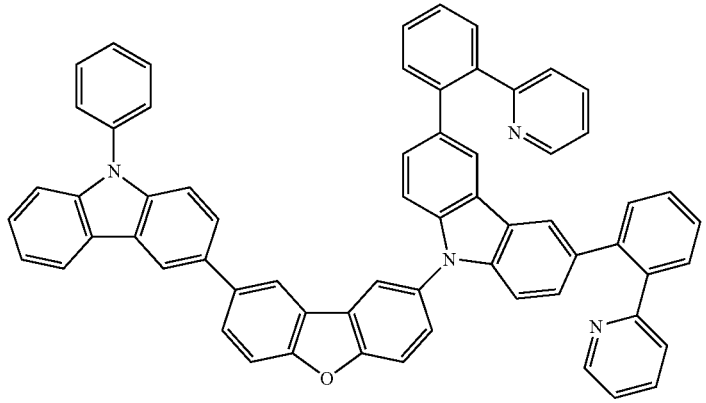

26
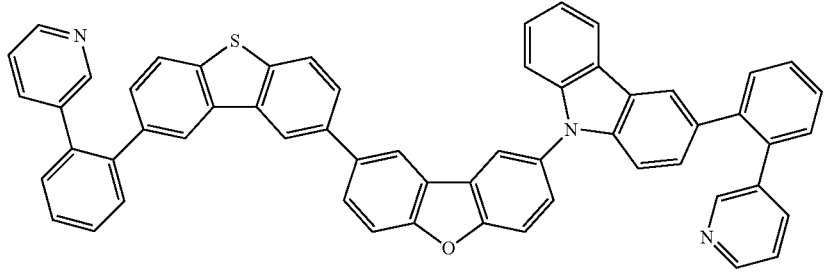
27
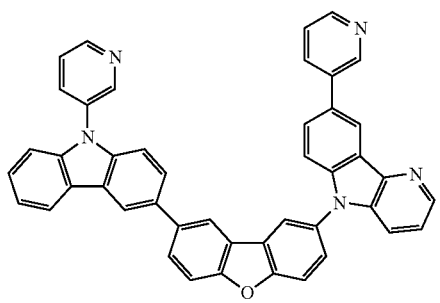
28
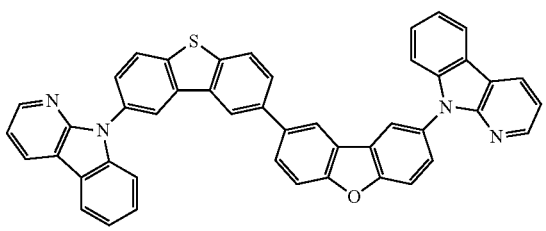
29
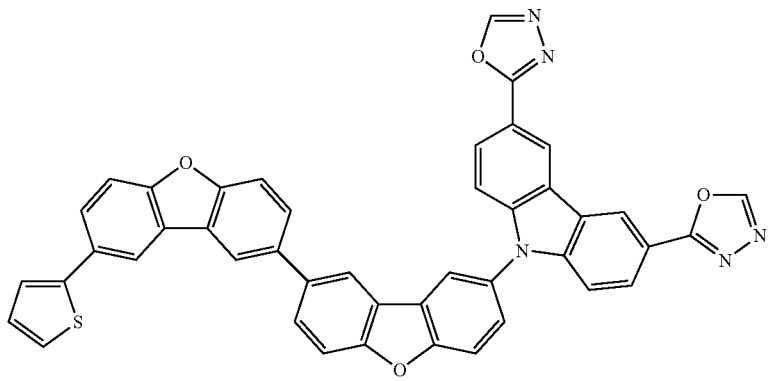
29'
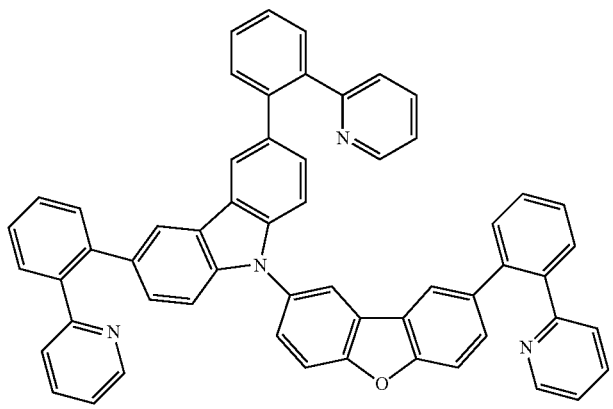

-continued
30
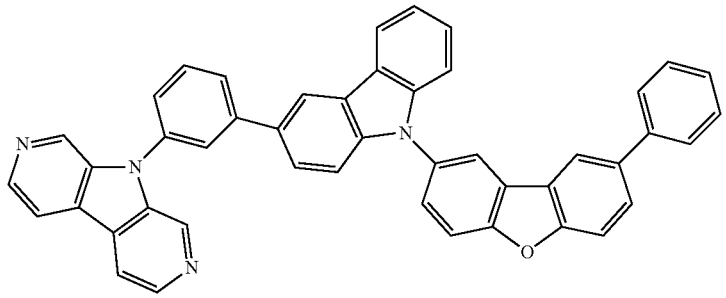
31
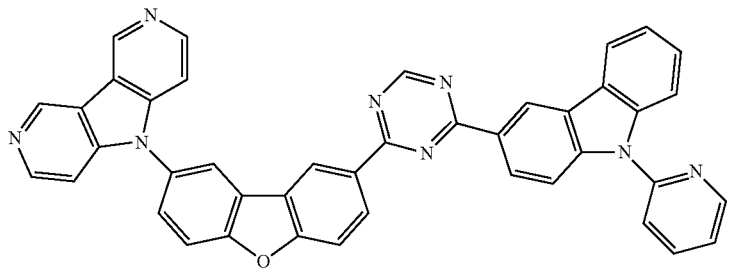
32
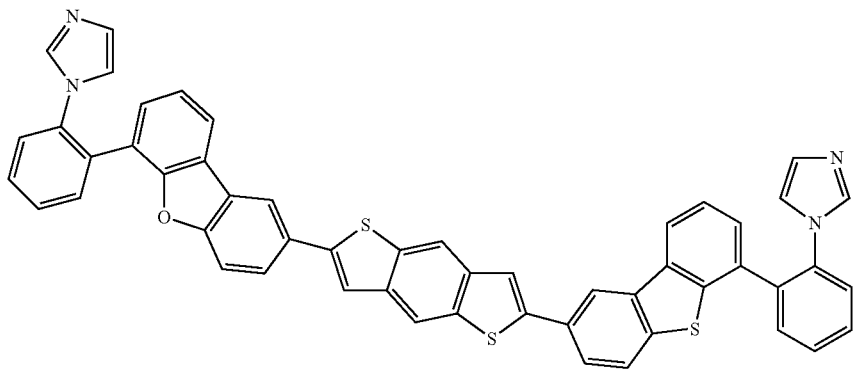
33
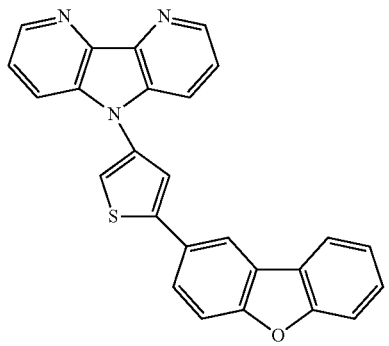
34
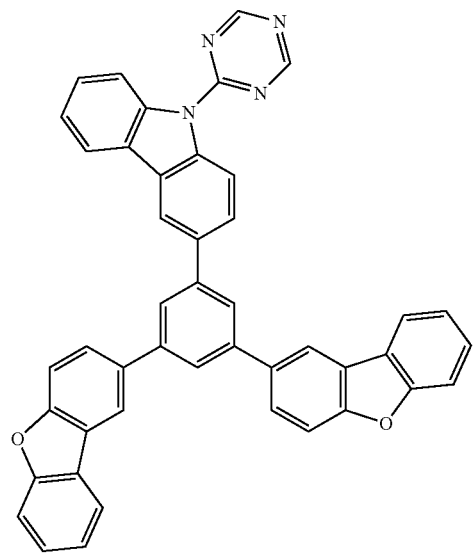

-continued
35
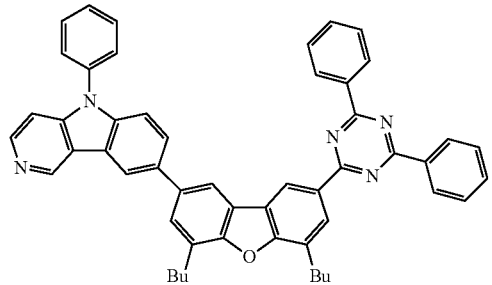
36
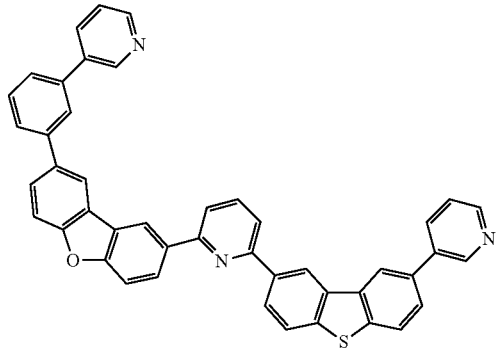
37
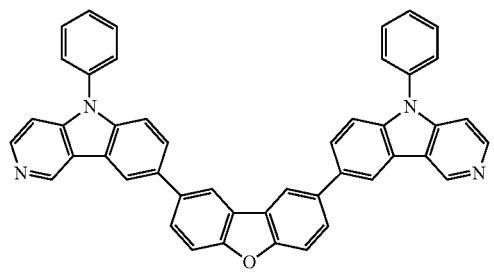
38
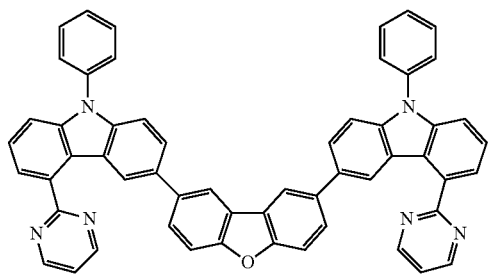
39
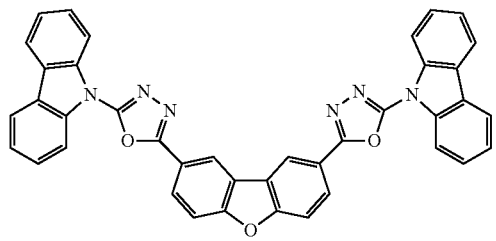
40
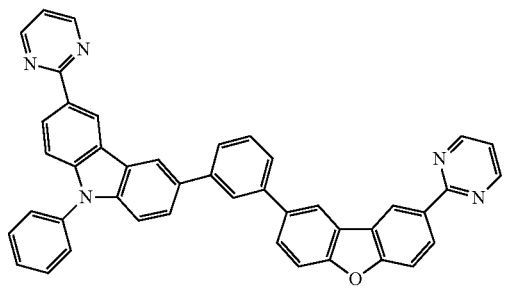
41
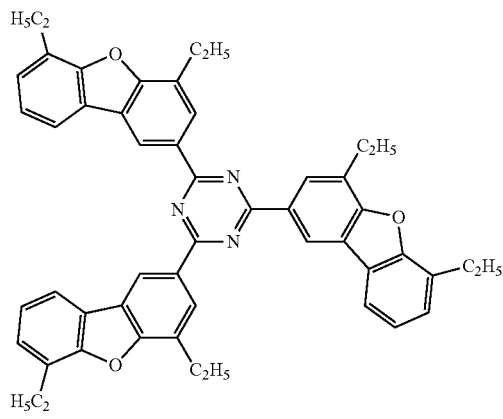
42
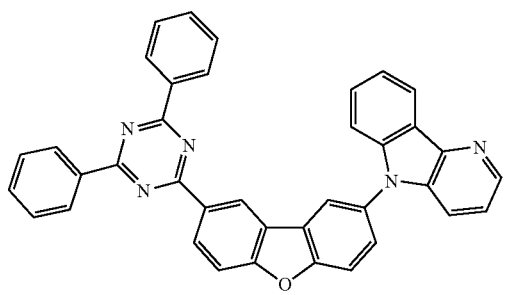
43
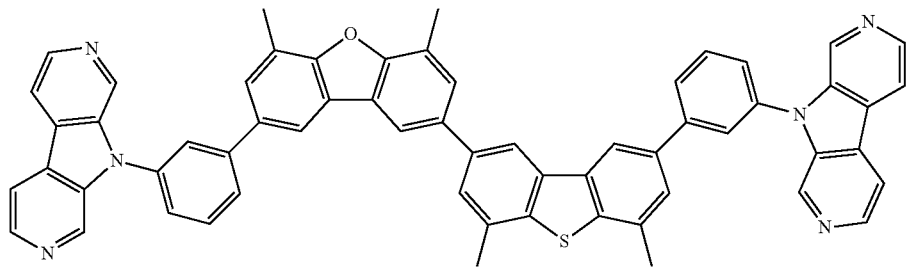

-continued
44
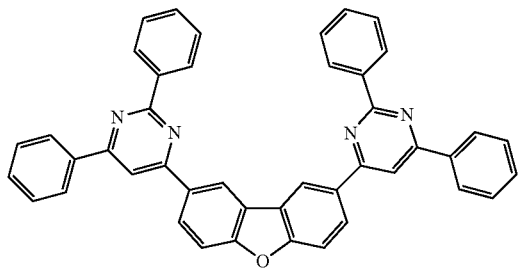
45
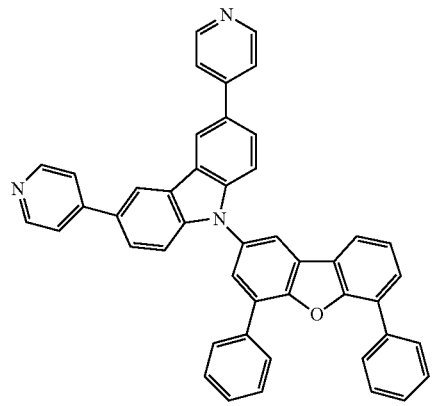
46
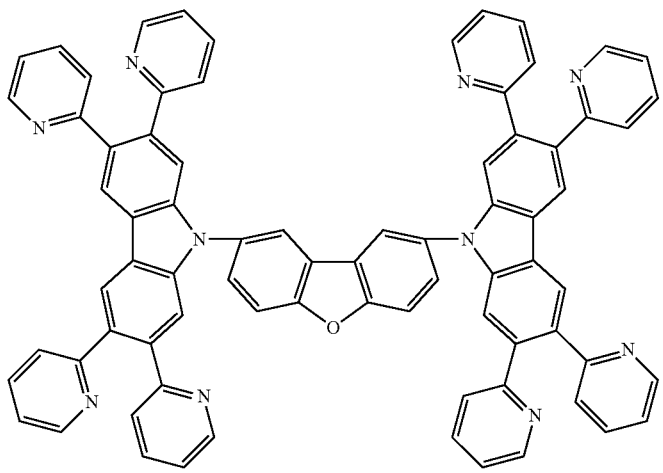
47
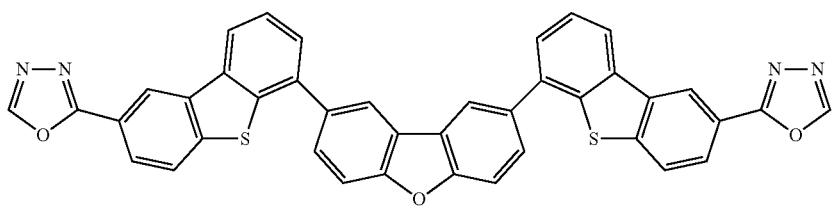
48
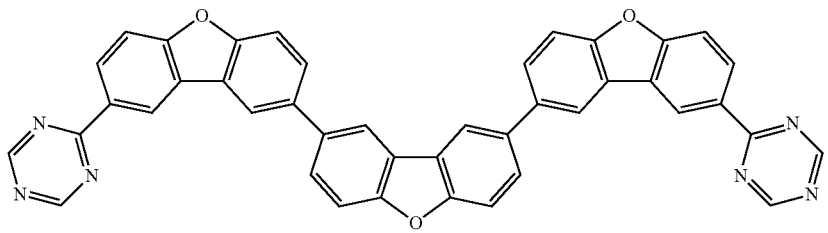
49
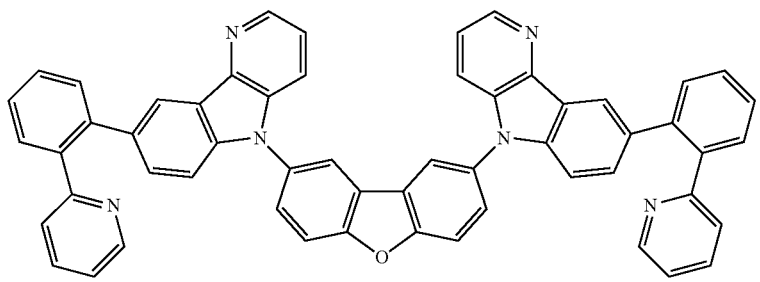

50
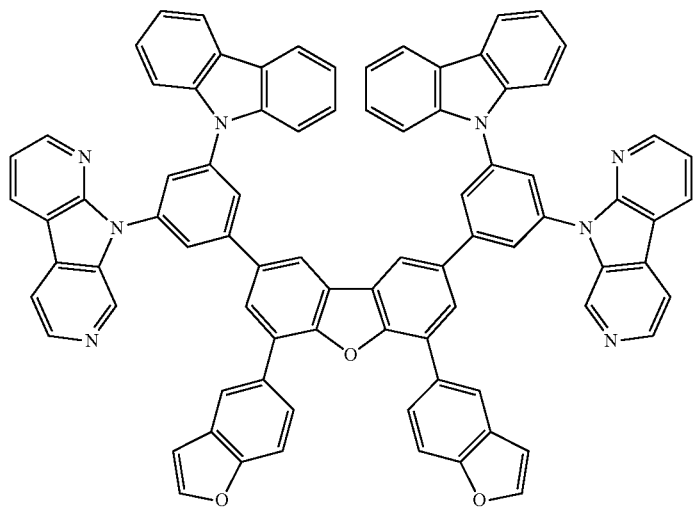
51
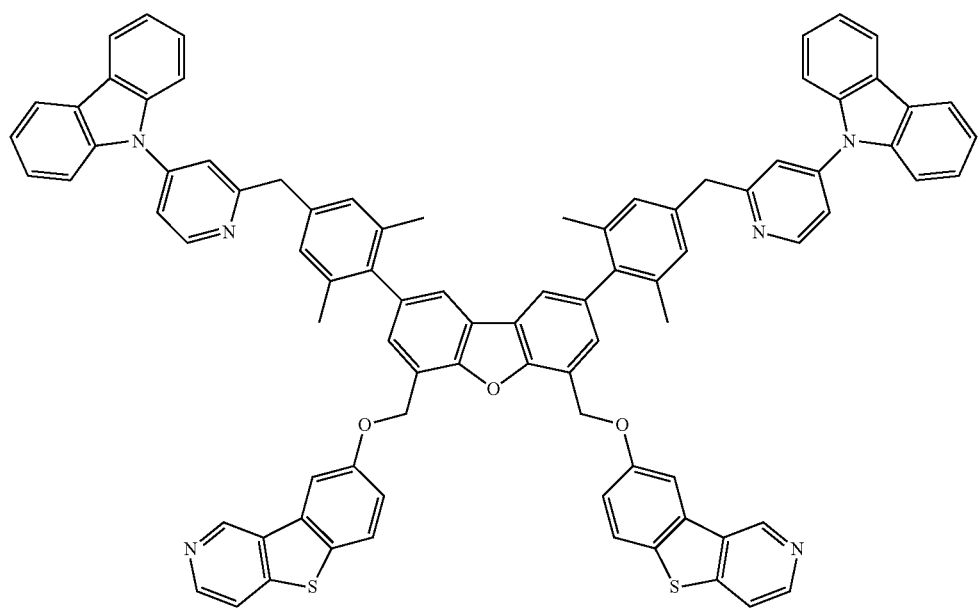
52
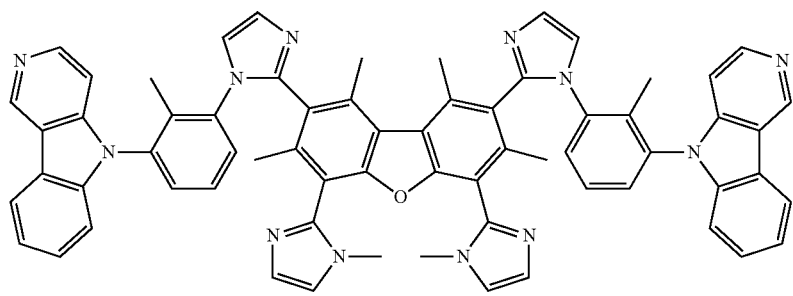

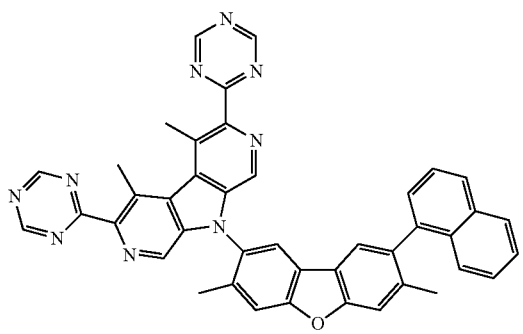

53

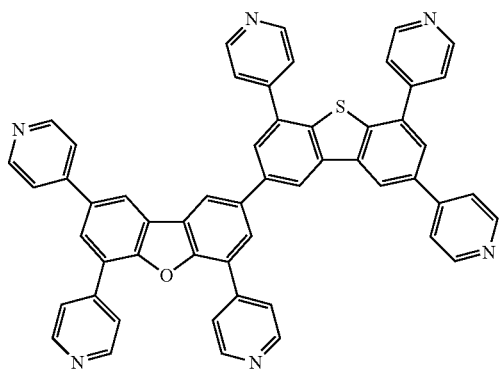

54

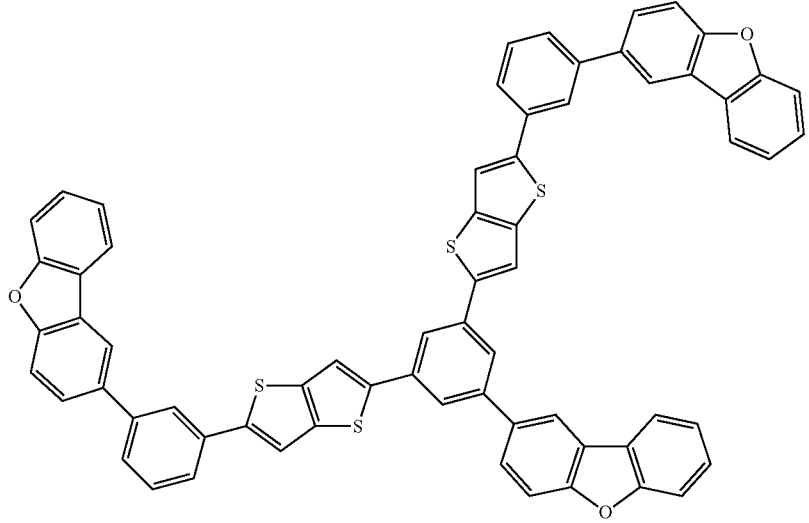

55

The compounds represented by any one of Formulas (1), (2), (3) and (4) of the present invention can be synthesized with reference to the well-known method described in WO 07/111,176, Chem. Mater., 2008, 20, 5951, Experimental Chemistry Lectures, the 5th edition (edited by The Chemical Society of Japan).

<<Compounds Represented by Formula (5)>>

As a phosphorescence emitting metal complex contained in the organic EL element of the present invention, the compounds represented by Formula (5) are preferable.

Hereafter, the compounds represented by Formula (5) will be described. Although the compound represented by Formula (5) is preferably contained as a light emitting dopant in a light emitting layer of an organic EL element of the present invention, it me be contained in other layer than the light emitting layer (the composing layer of the organic EL element of the present invention will be described later).

In Formula (5), examples of an aromatic hydrocarbon ring which is formed by A1 combined with P—C include: a benzene ring, a biphenyl ring, a naphthalene ring, an azulene ring, an anthracene ring, a phenanthrene ring, a pyrene ring, a chrysene ring, a naphthacene ring, a triphenylene ring, o-terphenyl ring, m-terphenyl ring, p-terphenyl ring, an acenaphthene ring, a coronene ring, a fluorene ring, a fluoanthrene ring, a naphthacene ring, a pentacene ring, a perylene ring, a pentaphene ring, a picene ring, a pyrene ring, a pyranthrene ring and an anthraanthrene ring.

These rings may further have a substituent represented by each of R1 to R7 in Formula (1).

In Formula (5), examples of an aromatic heterocycle which is formed by A1 combined with P—C include: a furan ring, a thiophene ring, an oxazole ring, a pyrrole ring, a pyridine ring, a pyridazine ring, a pyrrolidine ring, a pyrazine ring, a triazine ring, a benzimidazole ring, an oxadiazole ring, a triazole ring, an imidazole ring a pyrazole ring, a thiazole ring, an indole ring, a benzimidazole ring, a benzothiazole ring, a benzooxazole ring, a quinoxaline ring, a quinazoline ring, a phthalazine ring, a carbazole ring, and an azacarbazole ring.

Here, "an azacarbazole ring" indicates a ring structure in which one or plural carbon atoms in the benzene ring constituting the aforesaid carbazole ring is replaced with one or plural nitrogen atoms.

These rings may further have a substituent represented by each of R1 to R7 in Formula (1).

In Formula (5), examples of an aromatic heterocycle which is formed by A2 combined with Q-N include: an oxazole ring, an oxadiazole ring, an oxatriazole ring, an isoxazole ring, a tetrazole ring, a thiadiazole ring, a thiatriazole ring, an isothiazole ring, a pyrrole ring, a pyridine ring, a pyridazine ring, a pyrimidine ring, a pyrazine ring, a triazine ring, an imidazole ring, a pyrazole ring and a triazole ring.

These rings may further have a substituent represented by each of R1 to R7 in Formula (1).

In Formula (5), examples of a bidentate ligand represented by $P_1$-L1-$P_2$ include: phenylpyridine, phenylpyrazole, phenylimidazole, phenyltriazole, phenyltetrazole, pyrazabol, acetylacetone and picolinic acid.

In Formula (5), j1 represents an integer of 1 to 3, j2 represents an integer of 0 to 2, provided that the sum of j1 and j2 is 2 or 3. In particular, j2 is preferably 0.

In Formula (5), $M_1$ represents a transition metal element of Group 8 to Group 10 in the periodic table of the elements (it is simply called as a transition metal). In particular, $M_1$ is preferably iridium.

<<Compounds Represented by Formula (6)>>

Among the compounds represented by Formula (5) of the present invention, the compounds represented by Formula (6) are preferable.

In Formula (6), as a hydrocarbon ring group represented by Z, a non-aromatic hydrocarbon ring group and an aromatic hydrocarbon ring group are cited. And as a non-aromatic hydrocarbon ring group, a cyclopropyl group, a cyclopentyl group and a cyclohexyl group are cited. These groups may have no substituent or may have a substituent later mentioned.

Moreover, as an aromatic hydrocarbon ring group (it is called an aromatic hydrocarbon group or an aryl group), examples include: a phenyl group, p-chlorophenyl group, a mesityl group, a tolyl group, a xylyl group, a naphthyl group, an anthryl group, a azulenyl group, a acenaphthenyl group, a fluorenyl group, a phenanthryl group, an indenyl group, a pyrenyl group and a biphenylyl group.

These groups may have no substituent or may have a substituent represented by each of R1 to R7 in Formula (1).

In Formula (6), as a heterocyclic group represented by Z, there can be cited a non-aromatic heterocyclic group and an aromatic heterocyclic group. Examples of a non-aromatic heterocyclic group include a group derived from: an epoxy ring, an aziridine ring, a thiirane ring, an oxetane ring, an azethidine ring, a thiethane ring, a tetrahydrofuran ring, a dioxolane ring, a pyrrolidine ring, a pyrazolidine ring, an imidazolidine ring, an oxazolidine ring, a tetrahydrothiophene ring, a sulfolane ring, a thiazolidine ring, an □-caprolactone ring, an □-caprolactam ring, a piperidine ring, a hexahydropyridazine ring, a hexahydropyrimidine ring, a piperazine ring, a morpholine ring, a tetrahydropyran ring, a 1,3-dioxane rings, a 1,4-dioxane ring, a trioxane ring, a tetrahydrothiopyran ring, a thiomorpholine ring, a thiomorpholine 1,1-dioxide ring, a pyranose ring and a diazabicyclo [2,2,2]-octane ring.

These groups may have no substituent, or they may have a substituent represented by each of R1 to R7 in Formula (1).

Examples of an aromatic heterocyclic group include: a pyridyl group, a pyrimidinyl group, a furyl group, a pyrrolyl group, an imidazolyl group, a benzimidazolyl group, a pyrazolyl group, a pyrazinyl group, a triazolyl group (for example, 1,2,4-triazole-1-yl group, 1,2,3-triazole-1-yl group), an oxazolyl group, a benzoxazolyl group, a thiazolyl group, an isooxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, a carbolinyl group, a diazacarbazolyl group (indicating a ring structure in which one of carbon atoms constituting the carboline ring in the aforesaid carbolinyl group is replaced with one nitrogen atom), a quinoxalinyl group, a pyridazinyl group, a triazinyl group, a quinazolinyl group and a phthalazinyl group.

These groups may have no substituent, or they may have a substituent represented by each of R1 to R7 in Formula (1).

The group represented by Z is preferably an aromatic hydrocarbon ring group or an aromatic heterocyclic group.

Preferable examples of Z in Formula (6) are shown below, however, Z may have no substituent or may have further a substituent. Z is not limited to these examples. In addition, "*" indicated a linking position

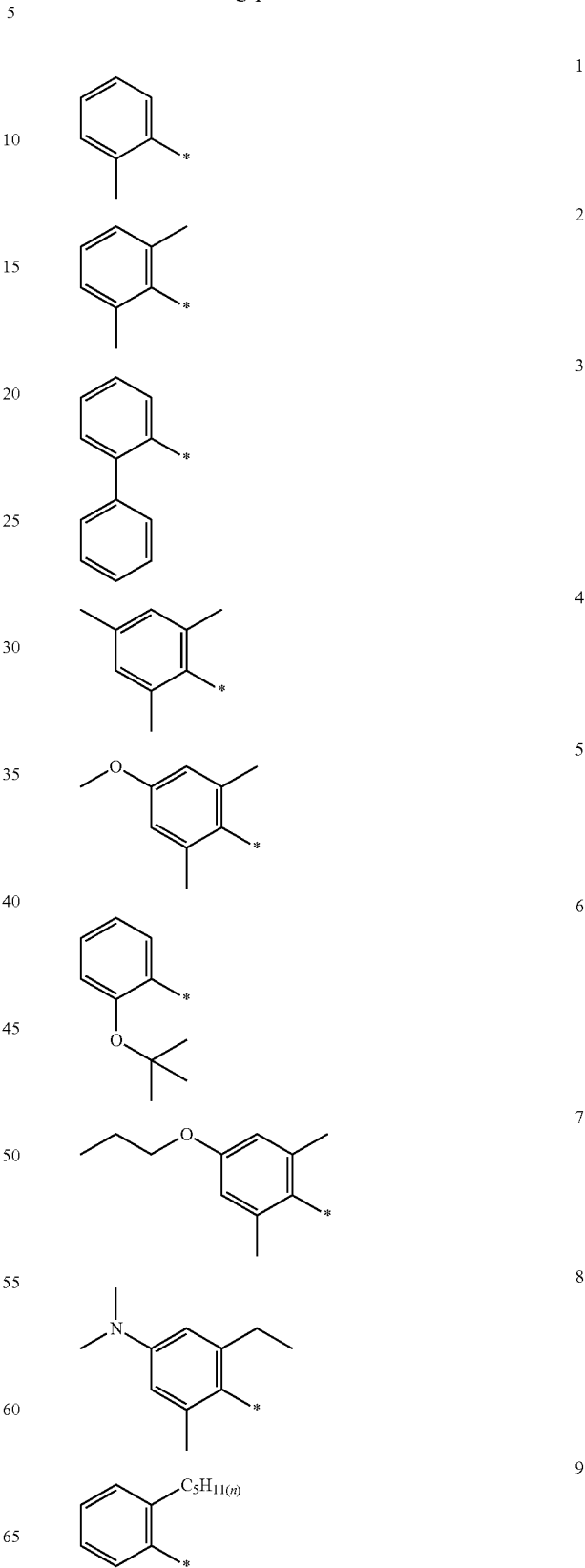

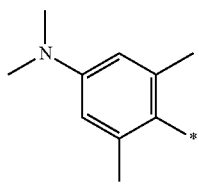
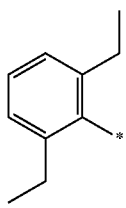
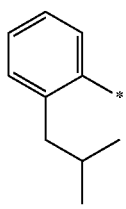
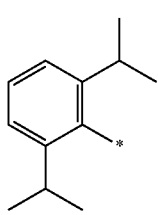
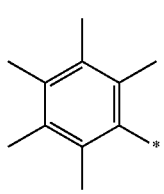
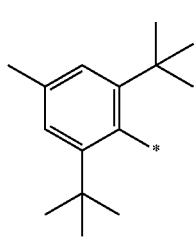
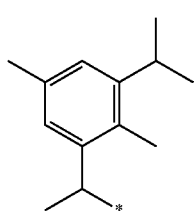
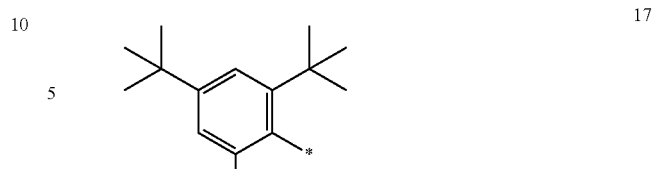
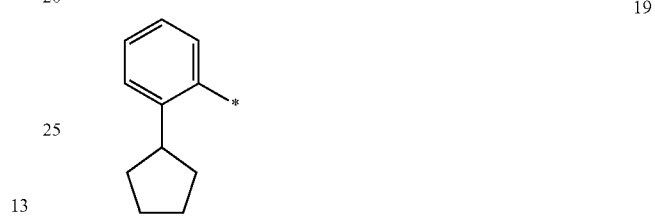
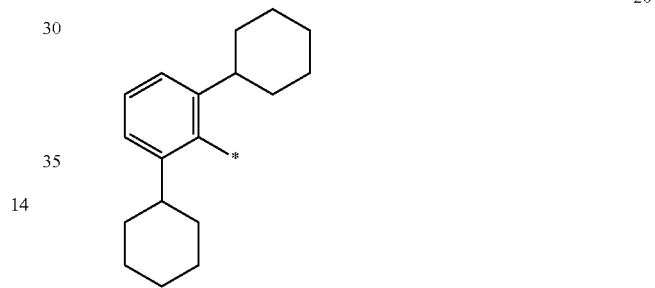
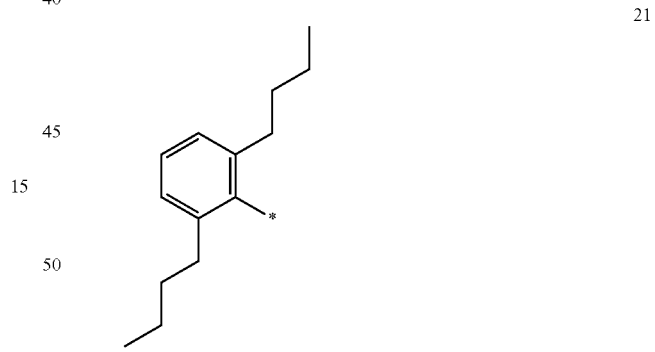
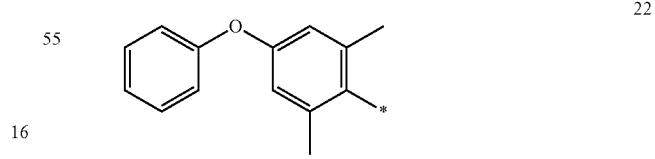

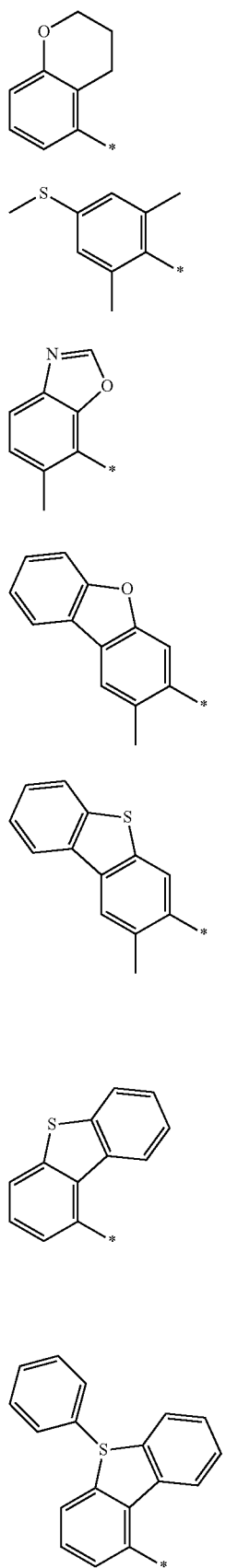
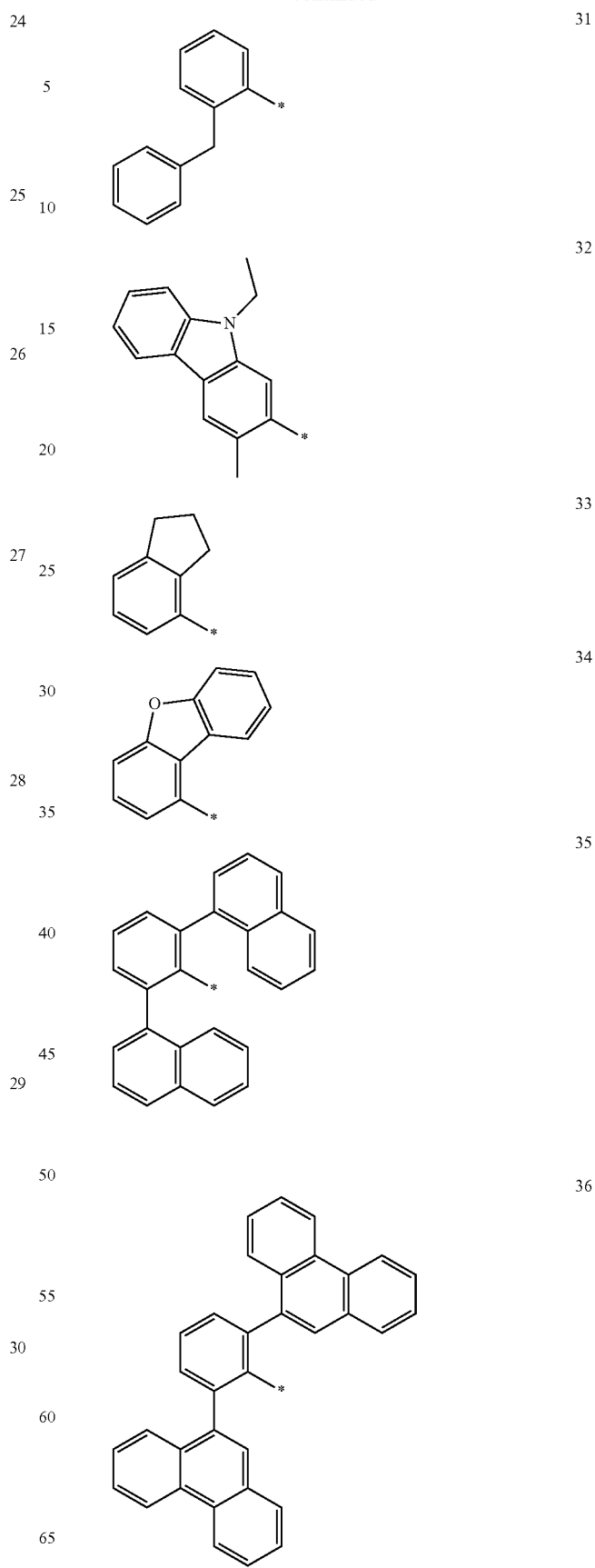

37
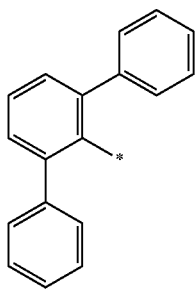
38
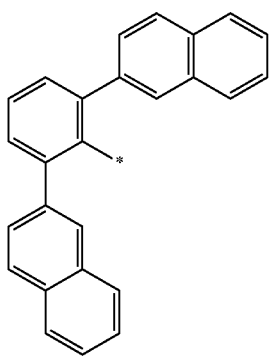
39
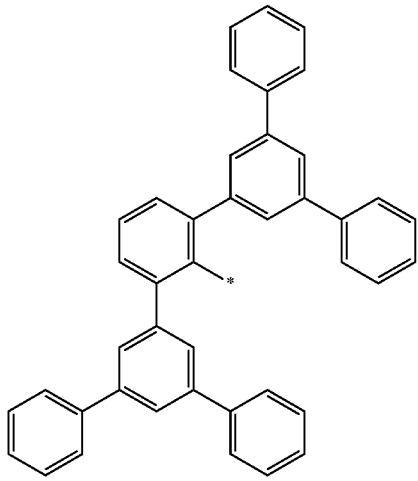
40
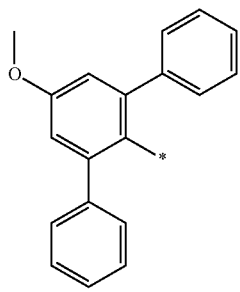
41
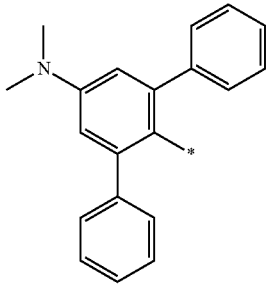
42
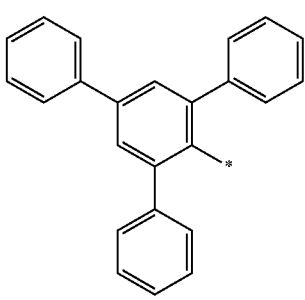
43
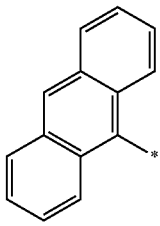
44
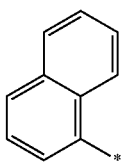
45
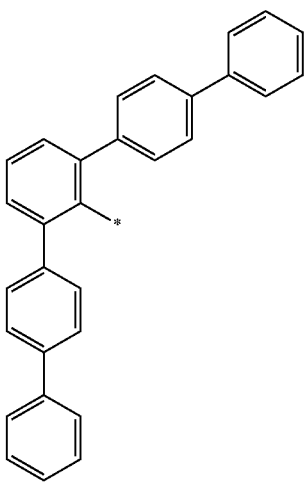

-continued
46
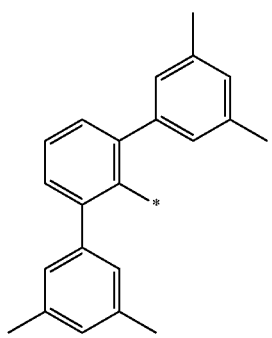
47
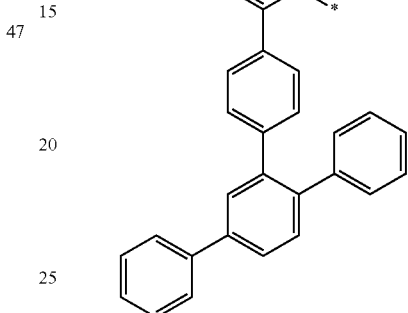
48
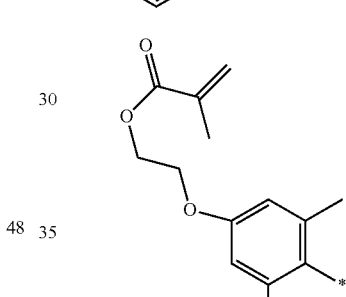
49
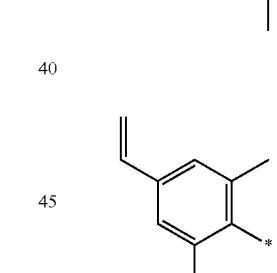
50
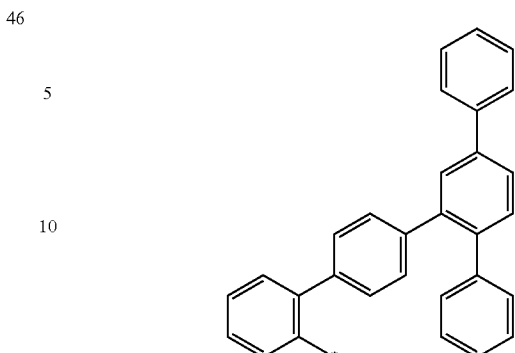
51
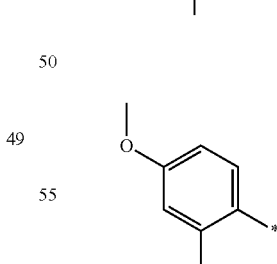
52
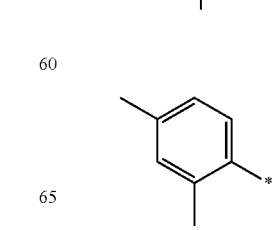
53
54

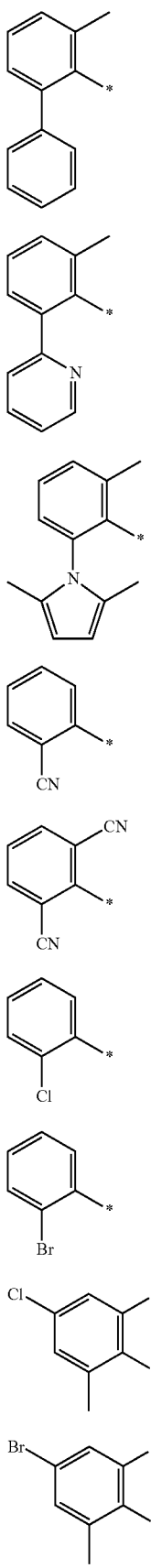
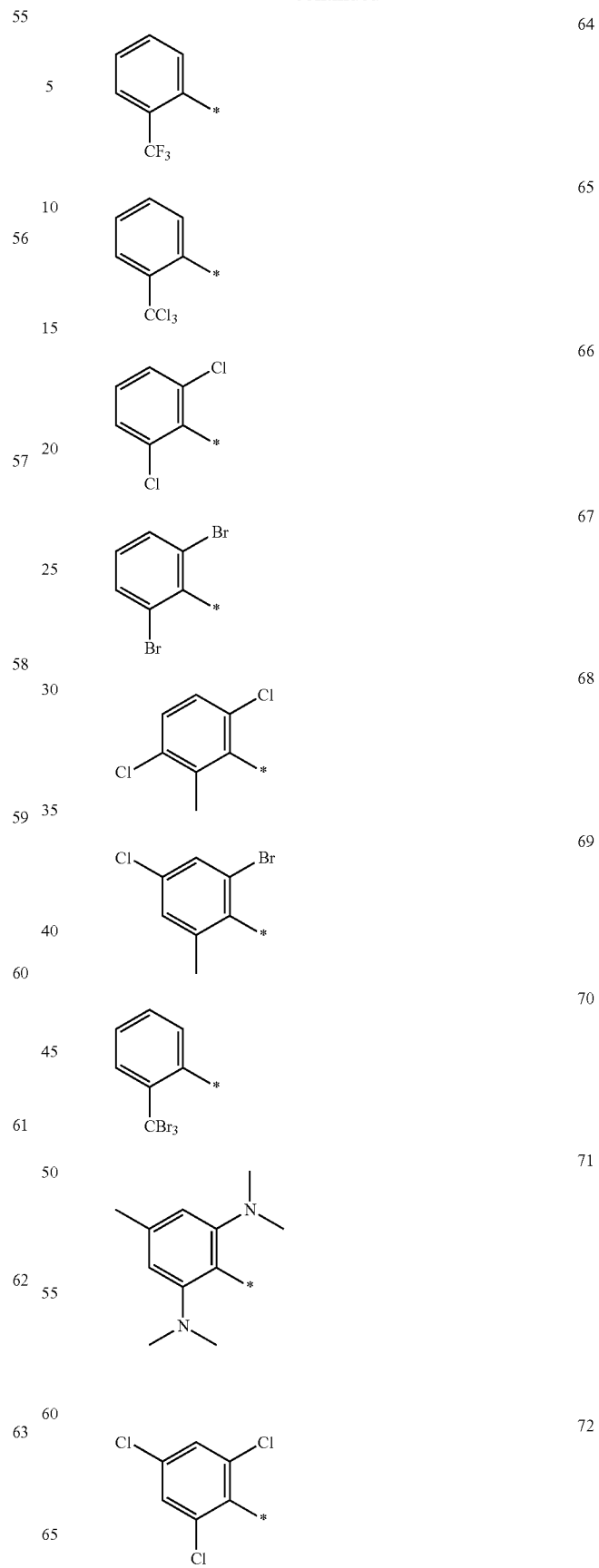

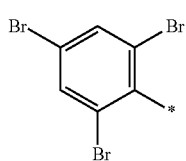
73
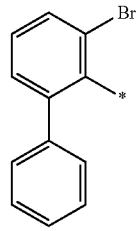
81
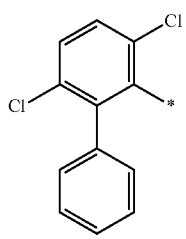
74
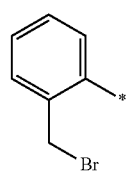
82
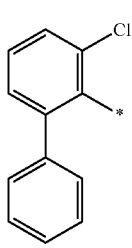
75
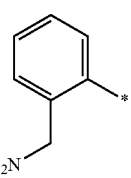
83
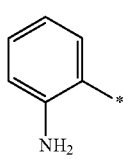
76
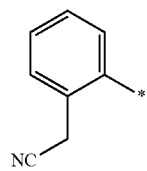
84
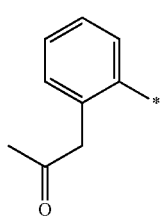
77
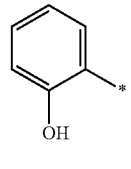
85
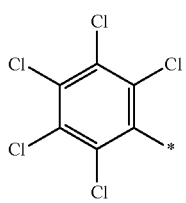
78
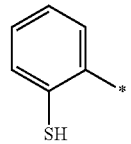
86
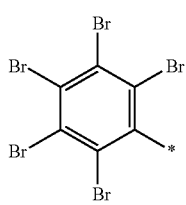
79
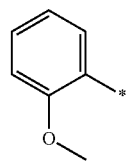
87
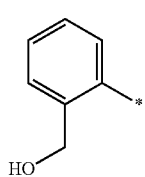
80
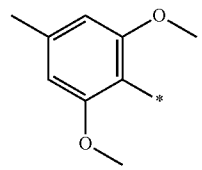
88

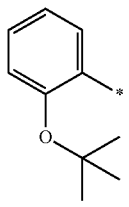
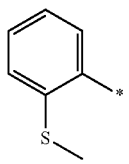
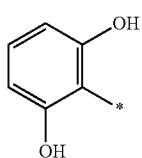
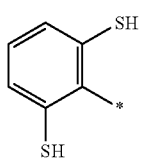
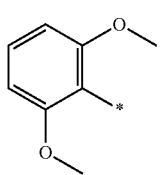
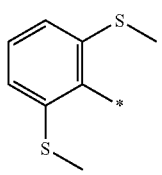
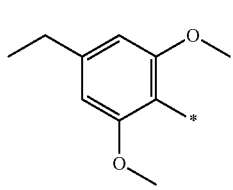
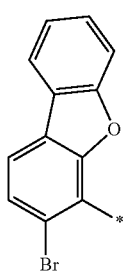
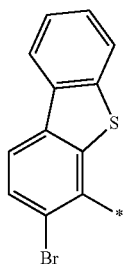
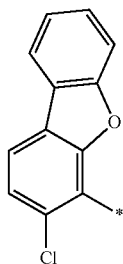
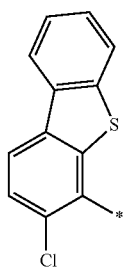
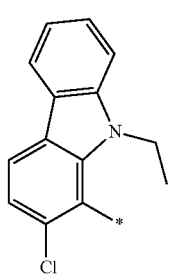
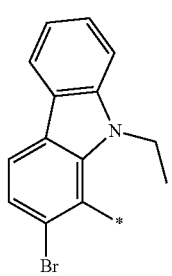

-continued
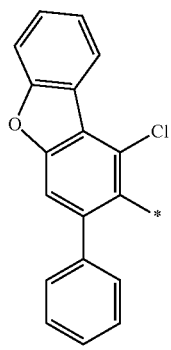
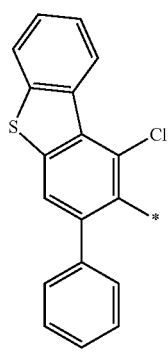
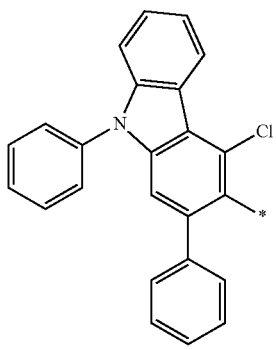
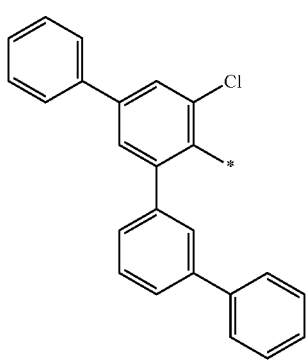
-continued
102
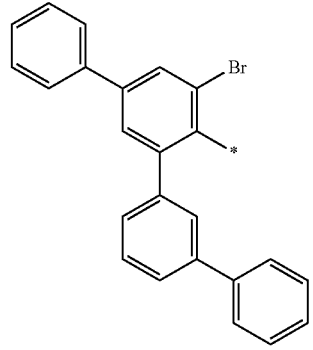
103
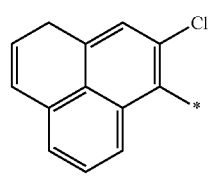
104
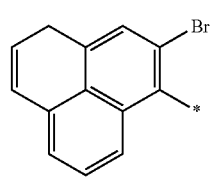
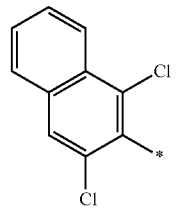
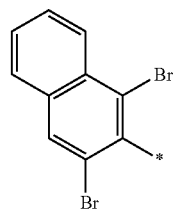
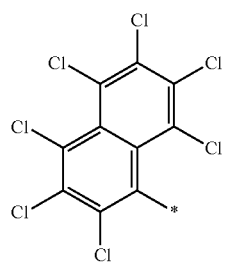
106
107
108
109
110
111

55
-continued
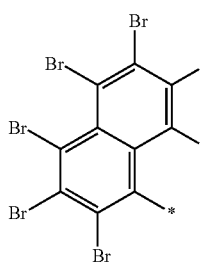 112
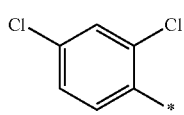 113
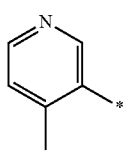 114
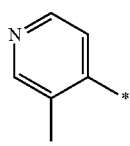 115
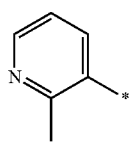 116
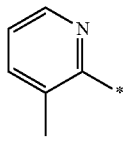 117
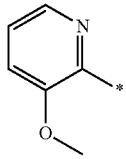 118
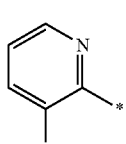 119
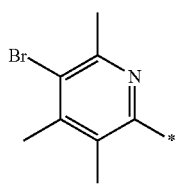 120
56
-continued
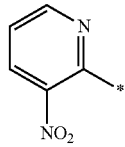 121
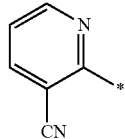 122
 123
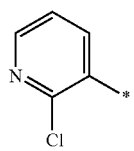 124
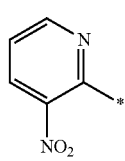 125
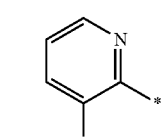 126
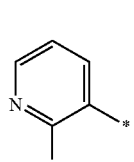 127
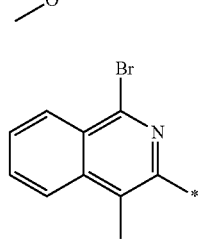 128
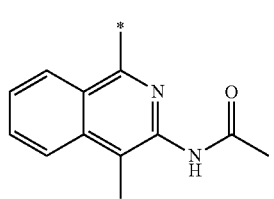 129

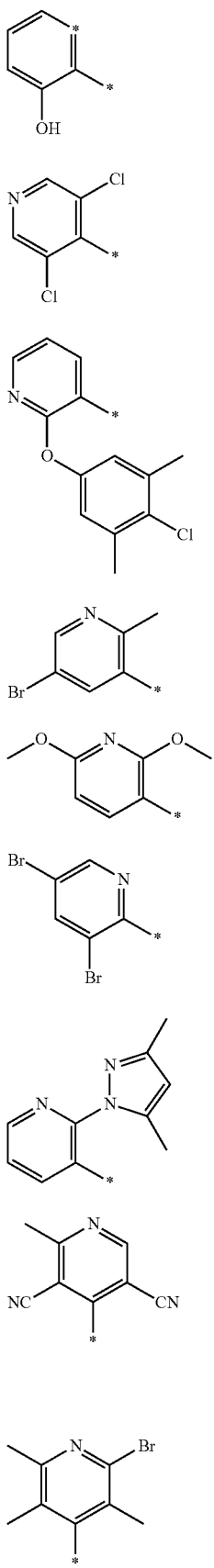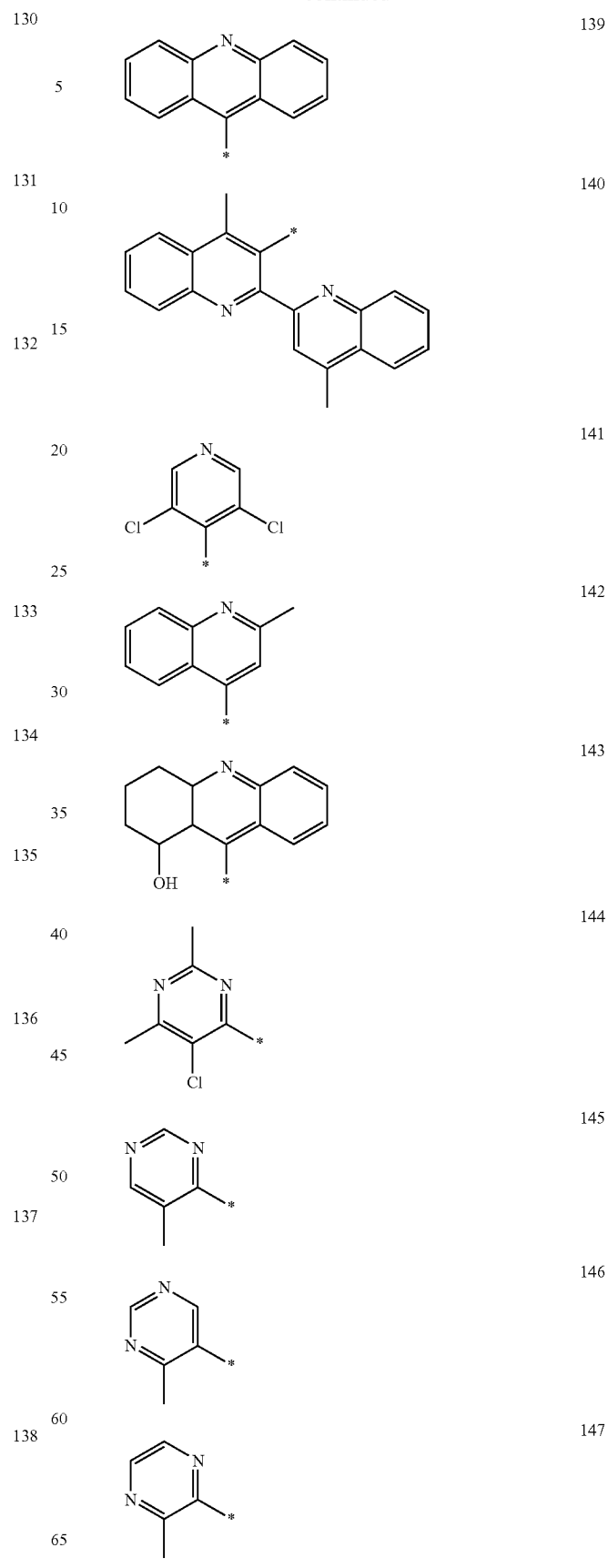

| | | |
|---|---|---|
| 148 | 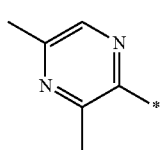 | 157 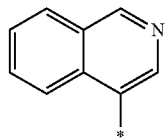 |
| 149 | 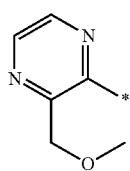 | 158 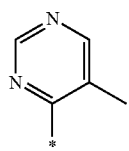 |
| 150 | 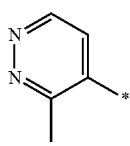 | 159 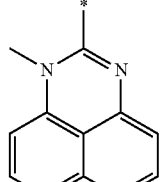 |
| 151 | 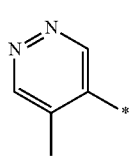 | 160 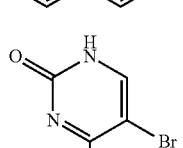 |
| 152 | 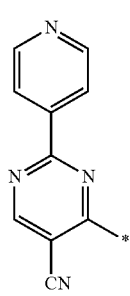 | 161  |
| 153 | 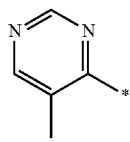 | 162 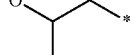 |
| 154 | 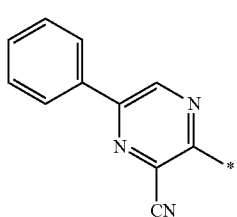 | 163 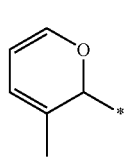 |
| 155 | 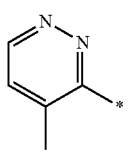 | 164 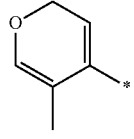 |
| 156 | 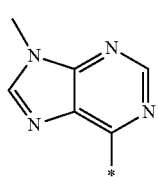 | 165 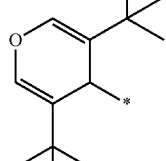 |
| | | 166 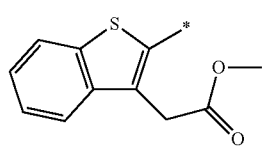 |

-continued
| | | |
|---|---|---|
| | 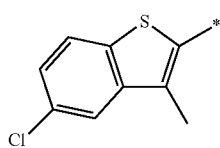 | 167 |
| | 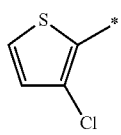 | 168 |
| | 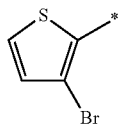 | 169 |
| | 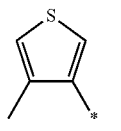 | 170 |
| | 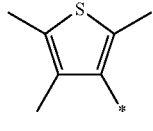 | 171 |
| | 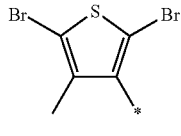 | 172 |
| | 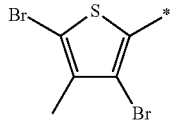 | 173 |
| | 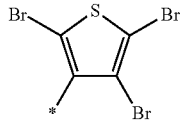 | 174 |
| | 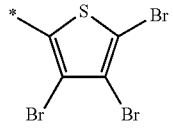 | 175 |
| | 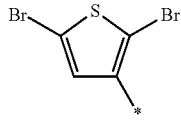 | 176 |
| | 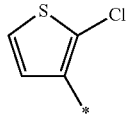 | 177 |
| | 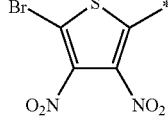 | 178 |
-continued
| | | |
|---|---|---|
| | 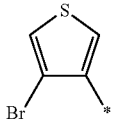 | 179 |
| | 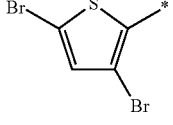 | 180 |
| | 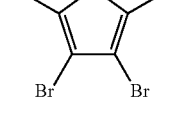 | 181 |
| | 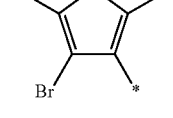 | 182 |
| | 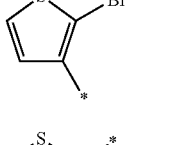 | 183 |
| | 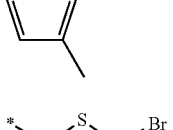 | 184 |
| | 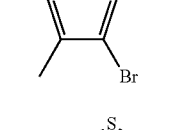 | 185 |
| | 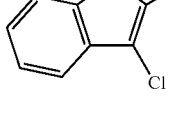 | 186 |
| | 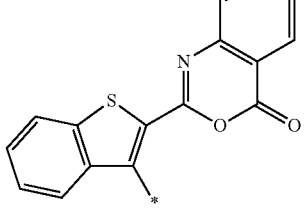 | 187 |
| | 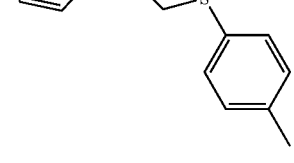 | 188 |

-continued
189 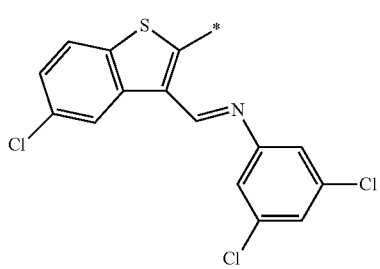
190 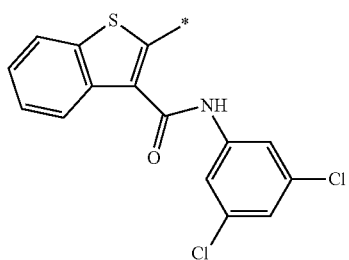
191 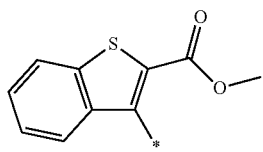
192 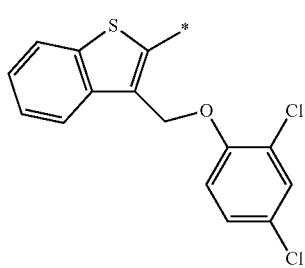
193 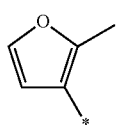
194 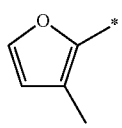
195 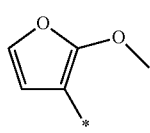
196 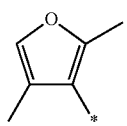
197 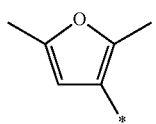
-continued
198 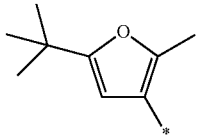
199 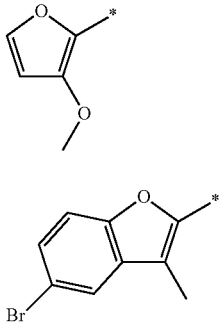
200 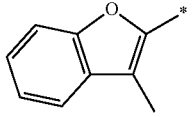
201 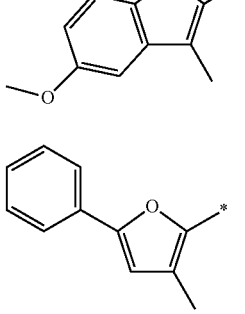
202 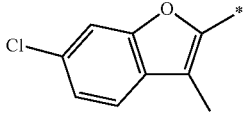
203 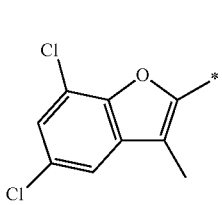
204 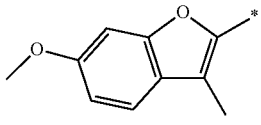

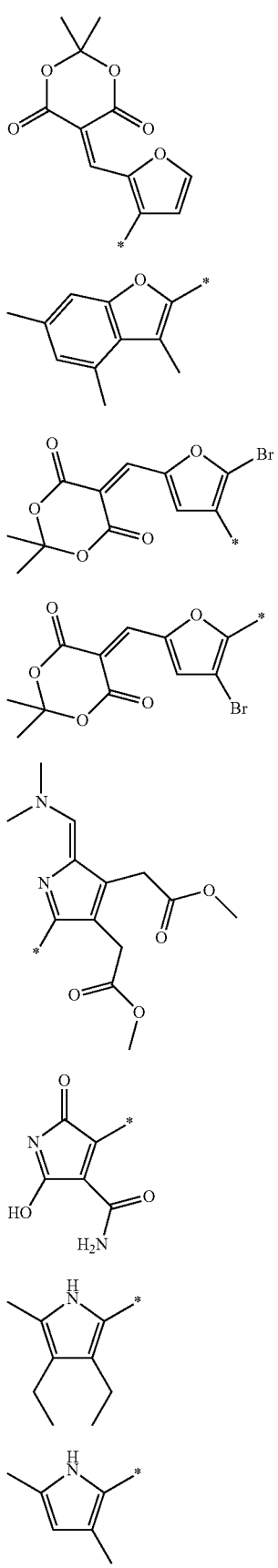
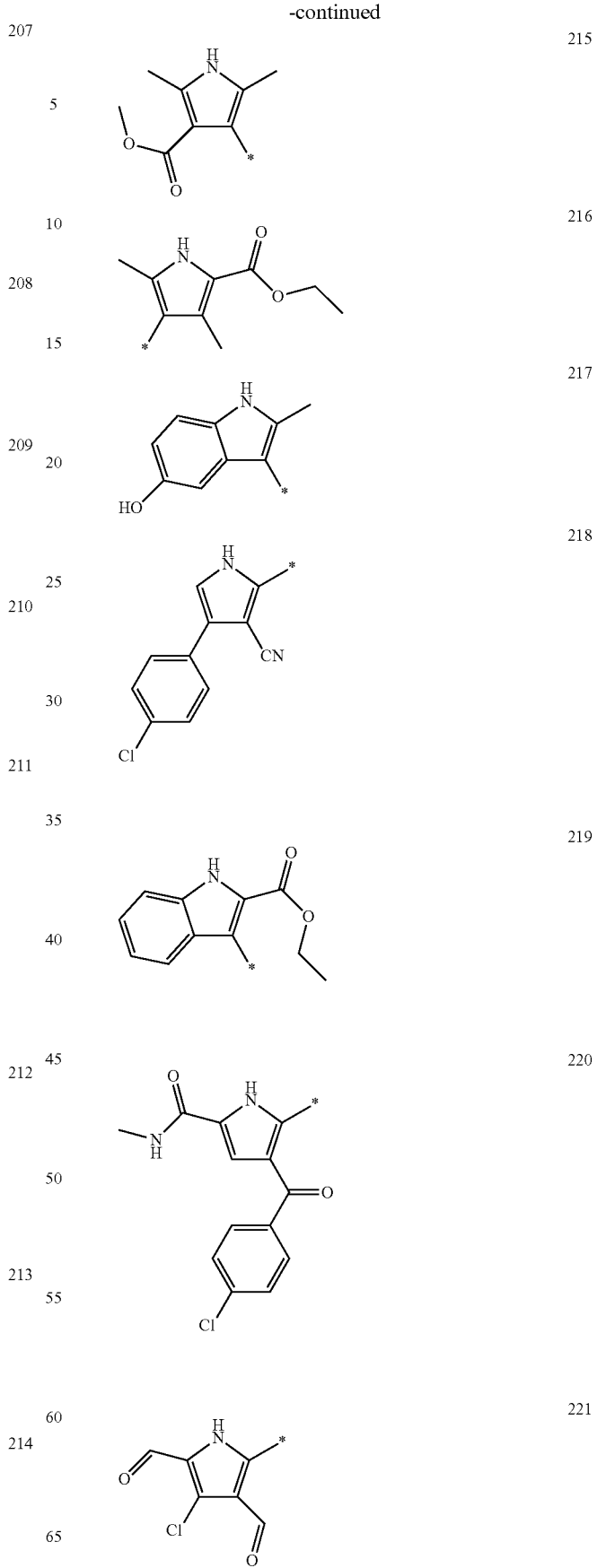

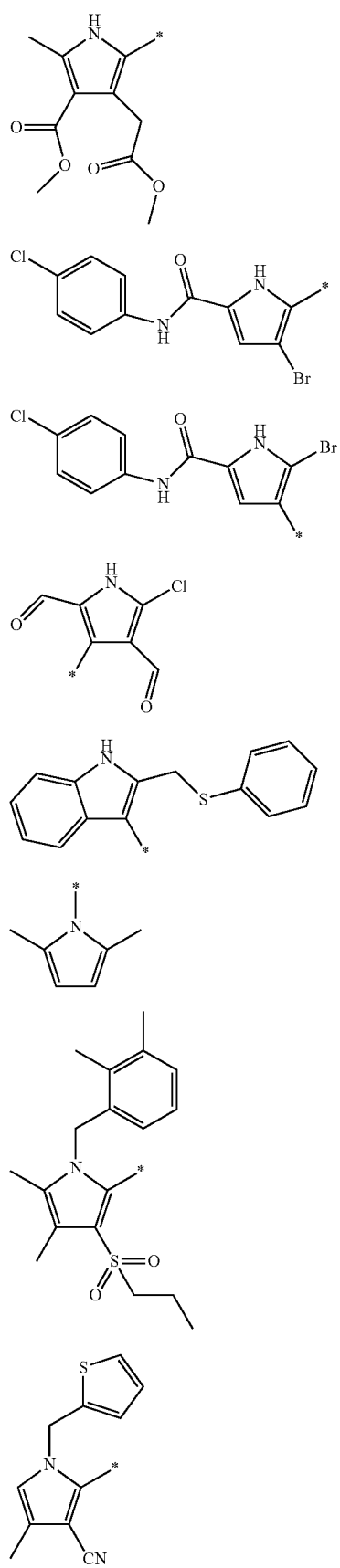
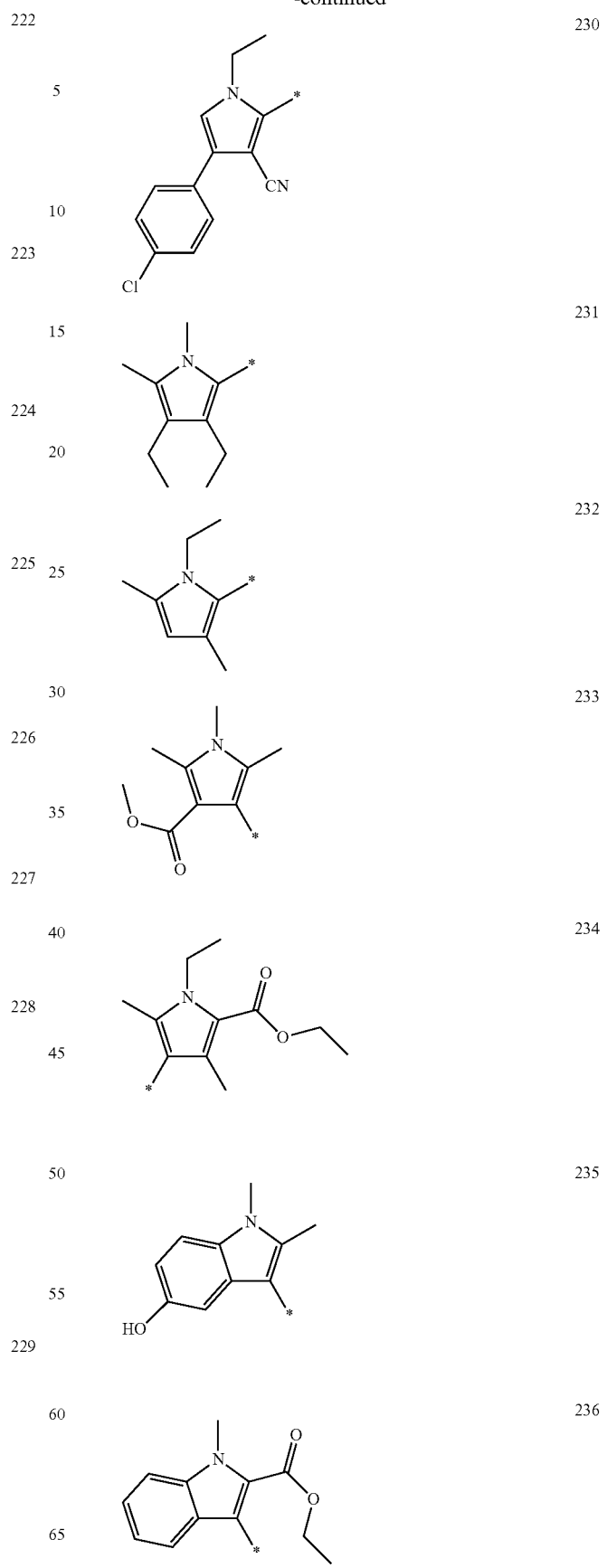

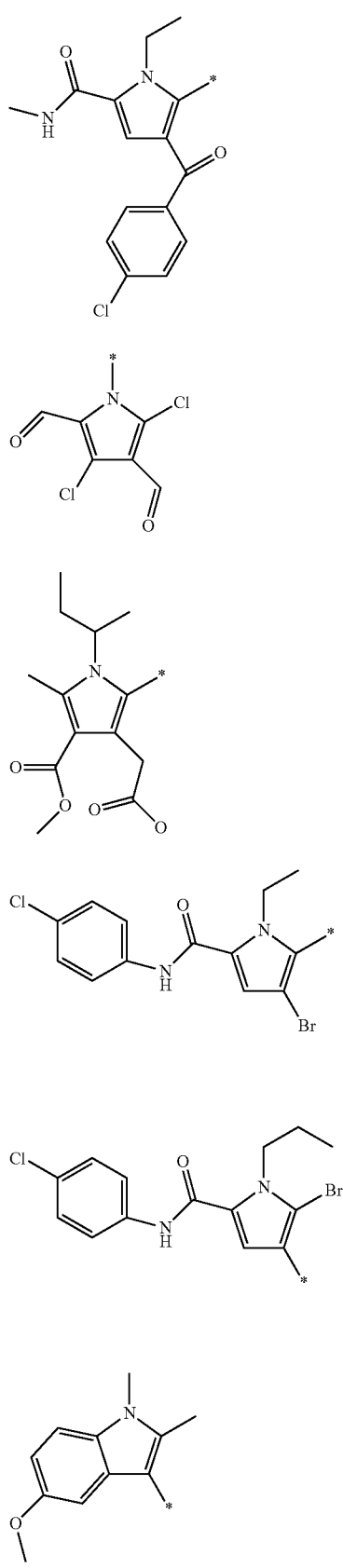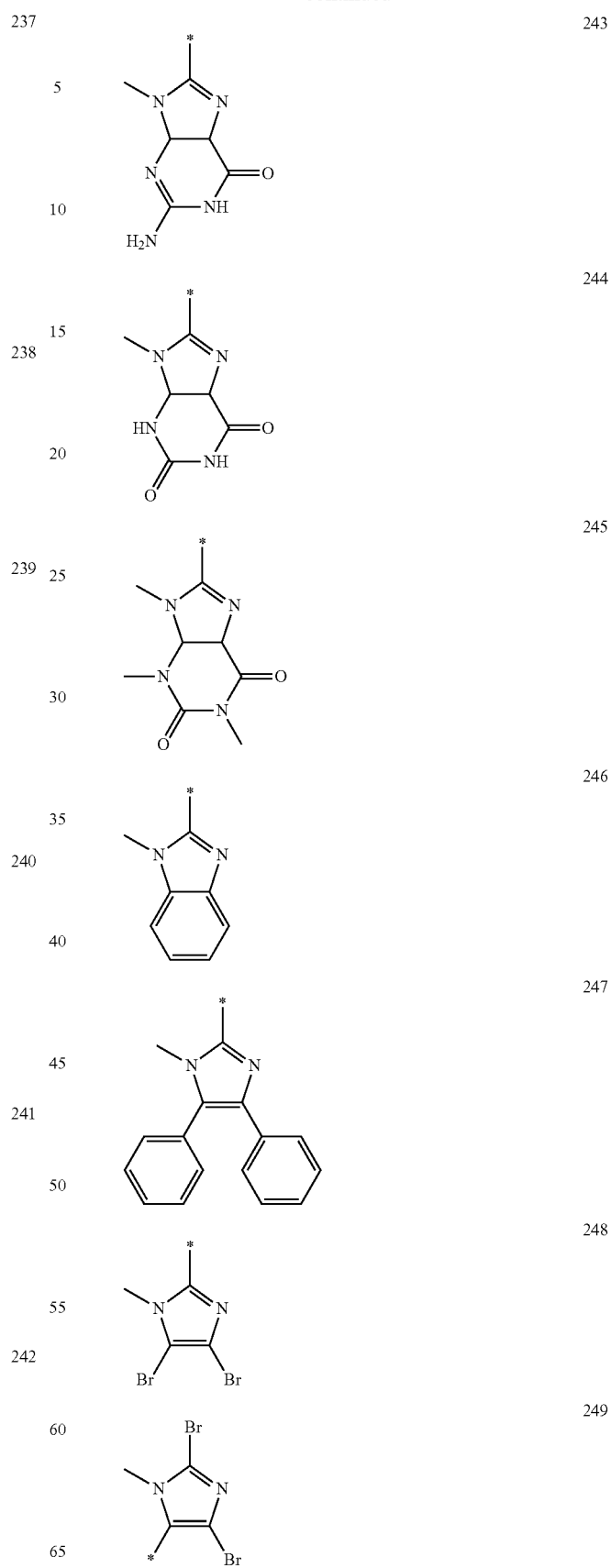

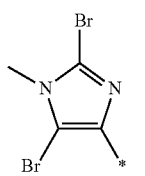
250
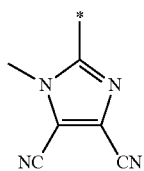
251
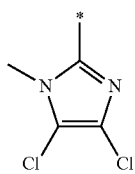
252
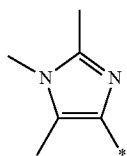
253
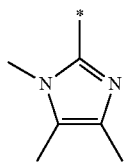
254
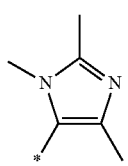
255
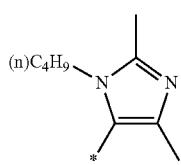
256
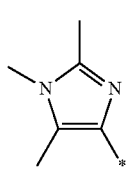
257
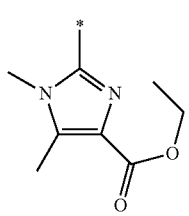
258
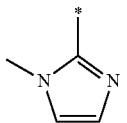
259
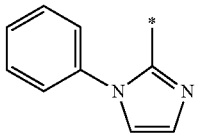
260
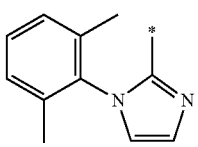
261
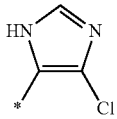
262
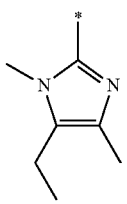
263
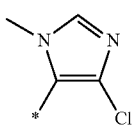
264
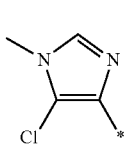
265
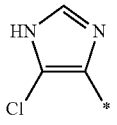
266
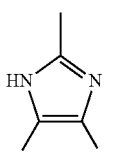
267
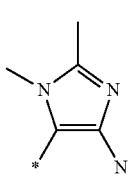
268

| | |
|---|---|
| 269 | 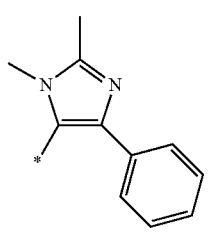 |
| 270 | |
| 271 | 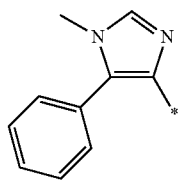 |
| 272 | 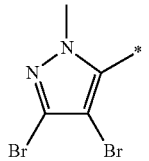 |
| 273 | 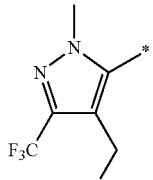 |
| 274 | 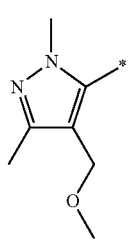 |
| 275 | 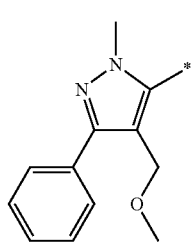 |
| 276 | |
| 277 | 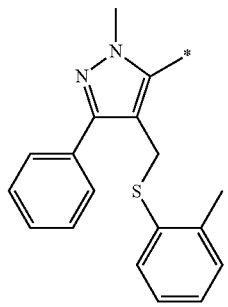 |
| 278 | |
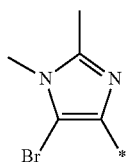
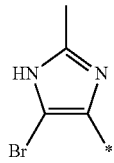
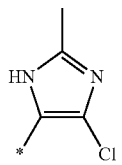
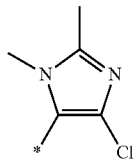
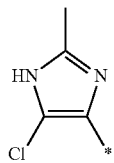
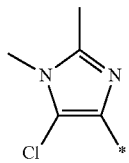
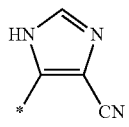
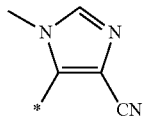
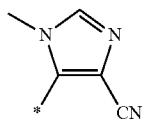
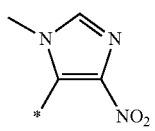

| | | |
|---|---|---|
| 286 | 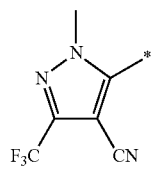 | 294 |
| 287 | 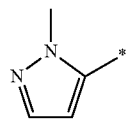 | 295 |
| 288 | 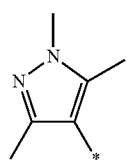 | 296 |
| 289 | 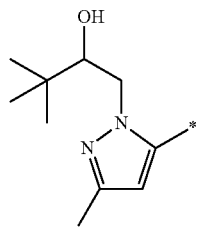 | 297 |
| 290 | 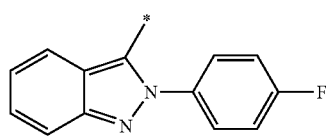 | 298 |
| 291 | 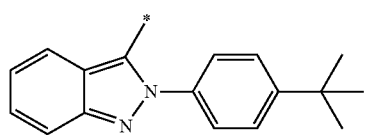 | 299 |
| 292 | 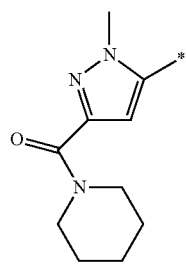 | 300 |
| 293 | 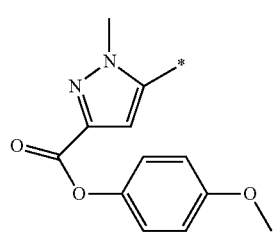 | 301 |
| | | 302 |
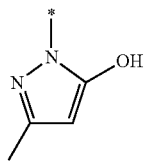
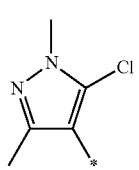
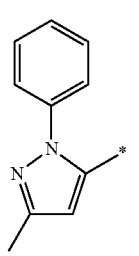
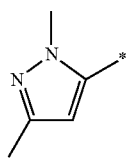
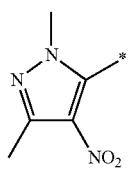
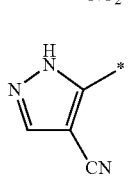
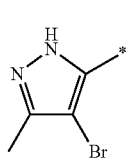
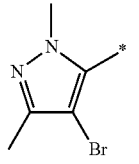
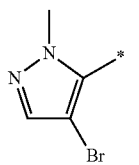

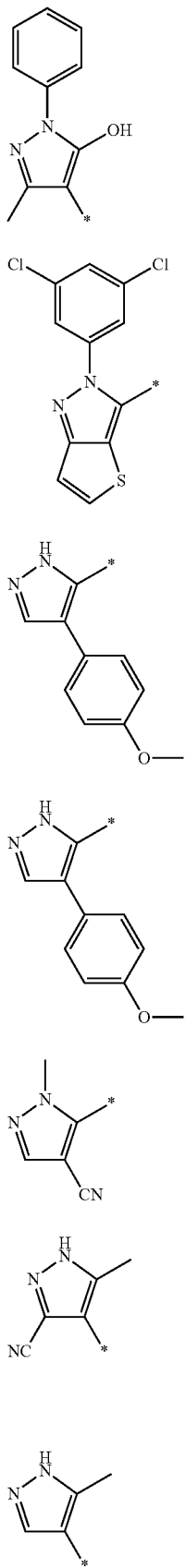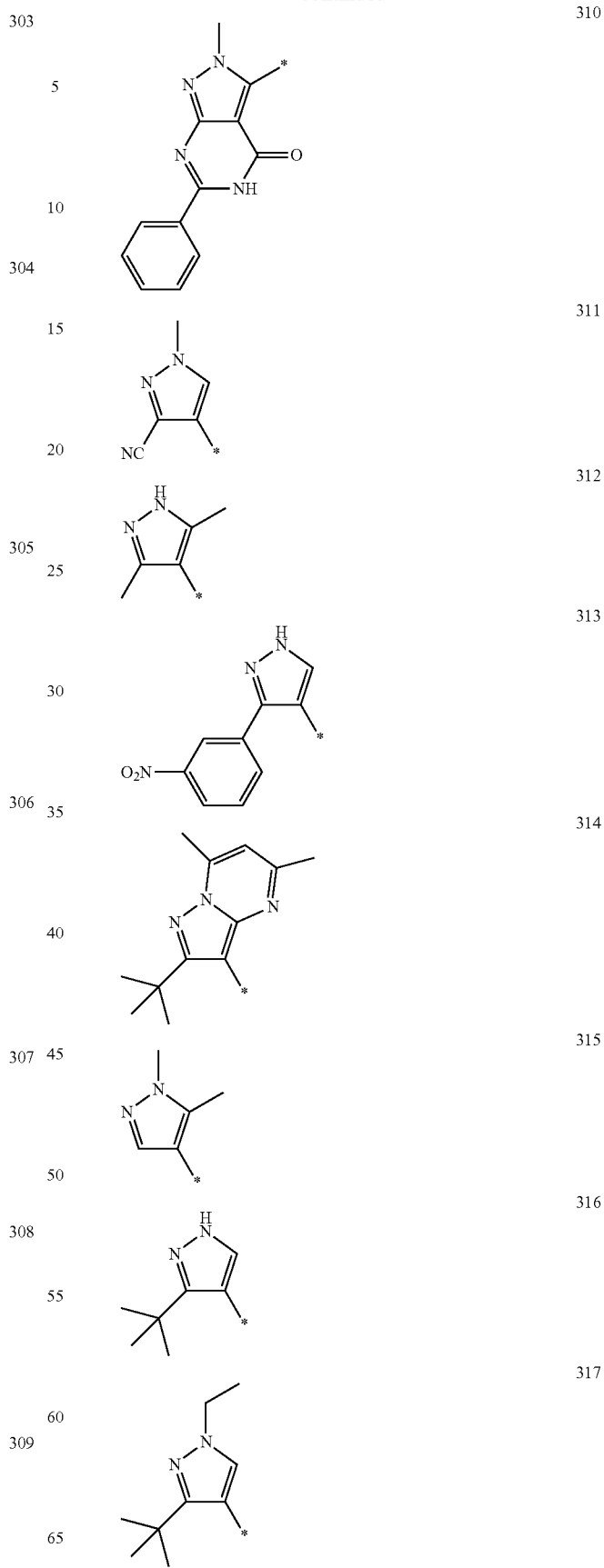

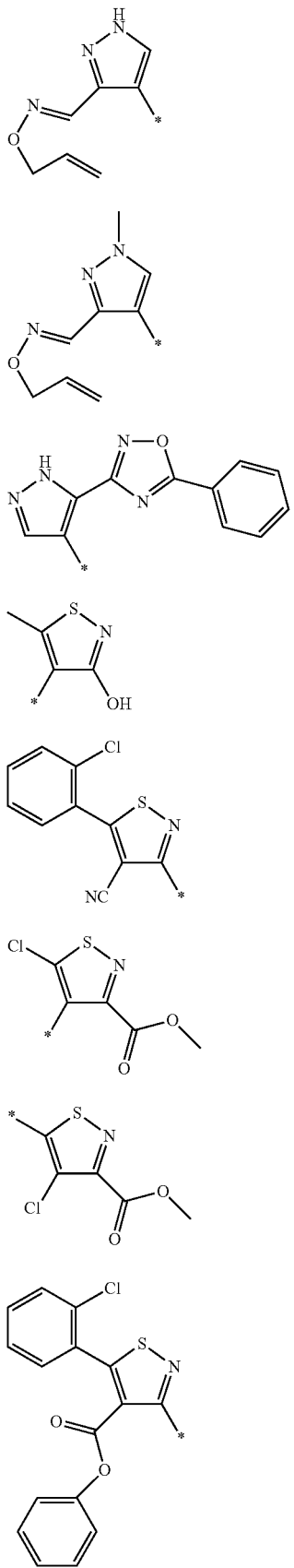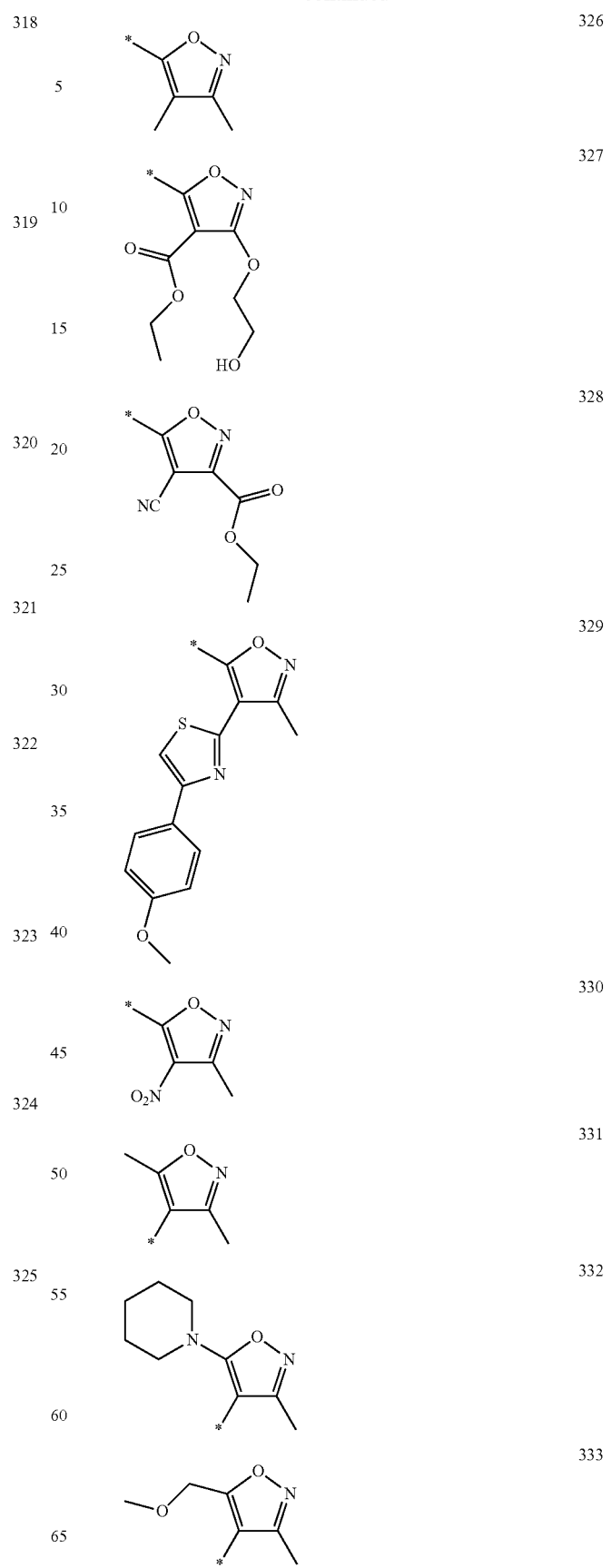

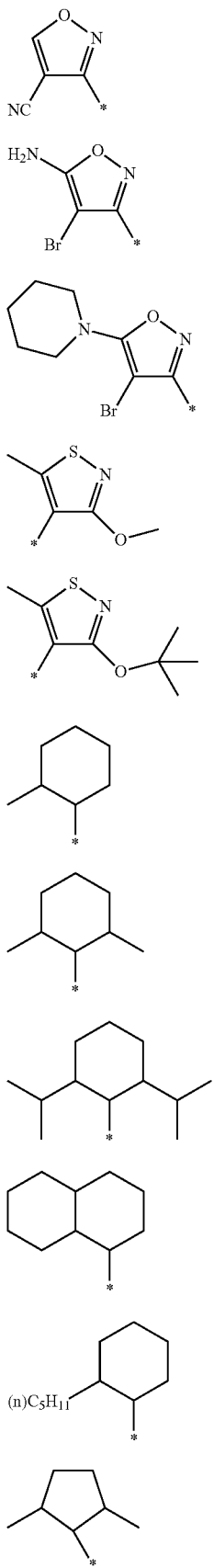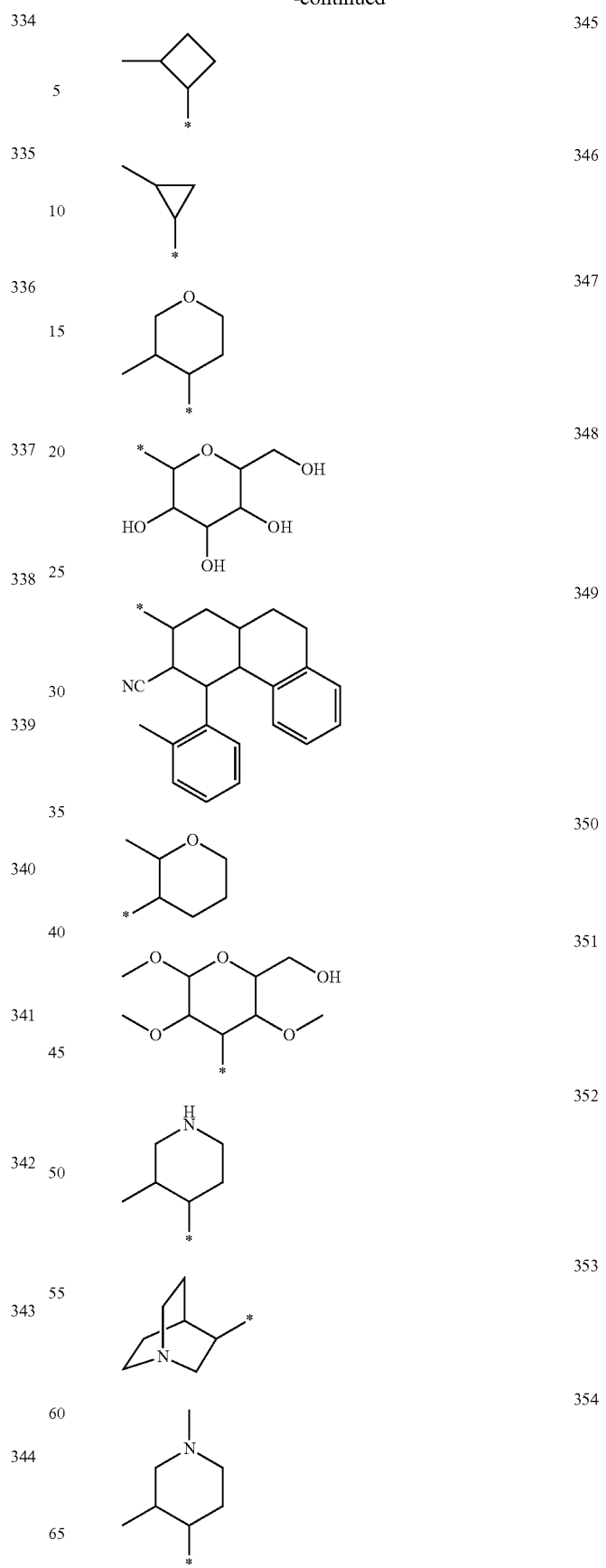

-continued
355 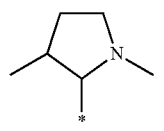
356 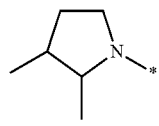
357 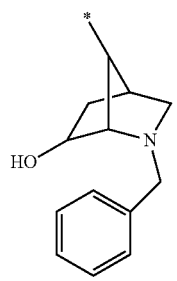
358 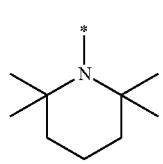
359 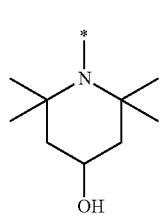
360 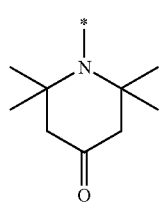
361 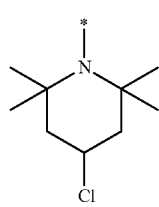
362 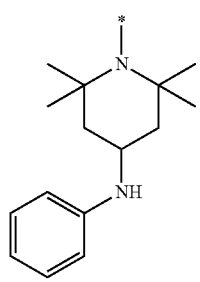
-continued
363 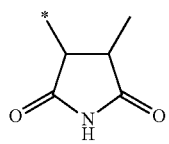
364 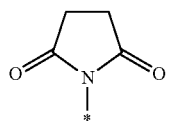
365 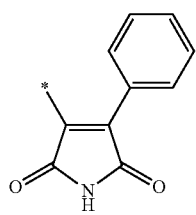
366 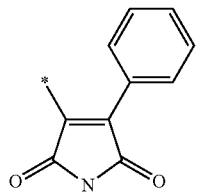
367 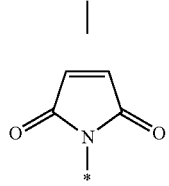
368 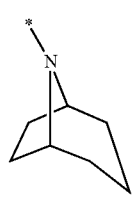
369 
370 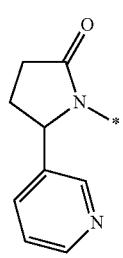

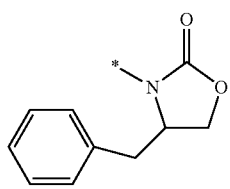
371
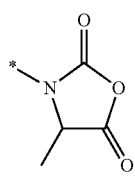
372
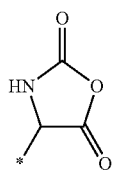
373
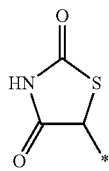
374
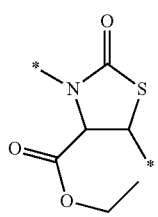
375
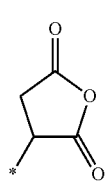
376
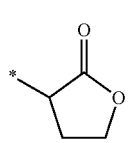
377
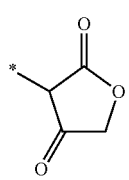
378
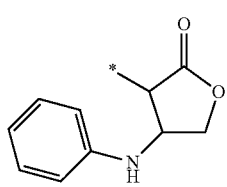
379
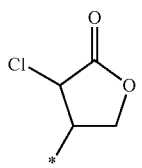
380
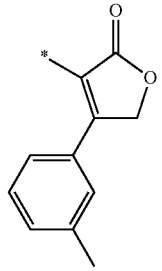
381
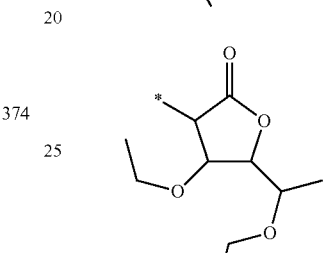
382
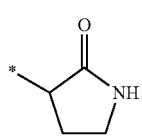
383
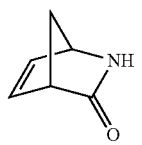
384
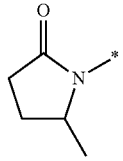
385
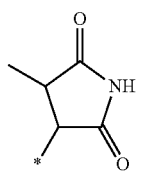
386
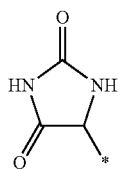
387

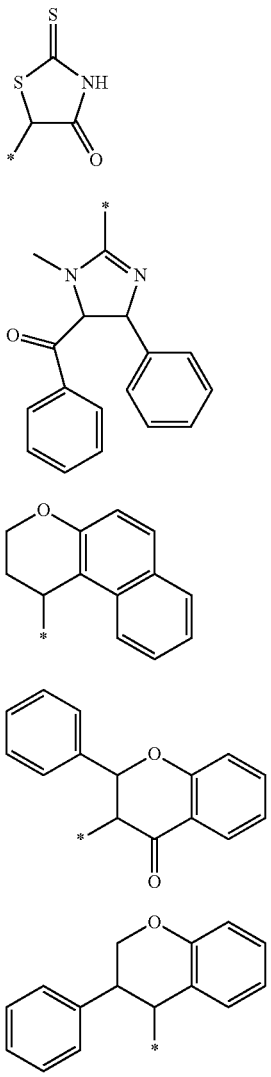

In Formula (6), examples of an aromatic hydrocarbon ring which is formed by A1 combined with P—C include: a benzene ring, a biphenyl ring, a naphthalene ring, an azulene ring, an anthracene ring, a phenanthrene ring, a pyrene ring, a chrysene ring, a naphthacene ring, a triphenylene ring, o-terphenyl ring, m-terphenyl ring, p-terphenyl ring, an acenaphthene ring, a coronene ring, a fluorene ring, a fluoanthrene ring, a naphthacene ring, a pentacene ring, a perylene ring, a pentaphene ring, a picene ring, a pyrene ring, a pyranthrene ring and an anthraanthrene ring.

These rings may further have a substituent represented by each of R1 to R7 in Formula (1).

In Formula (6), examples of an aromatic heterocycle which is formed by A1 combined with P—C include: a furan ring, a thiophene ring, an oxazole ring, a pyrrole ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an indole ring, a benzimidazole ring, a benzothiazole ring, a benzooxazole ring, a quinoxaline ring, a quinazoline ring, a phthalazine ring, a carbazole ring, a carboline ring and an azacarbazole ring.

Here, "an azacarbazole ring" indicates a ring structure in which one or plural carbon atoms in the benzene ring constituting the aforesaid carbazole ring is replaced with one or plural nitrogen atoms.

These rings may further have a substituent represented by each of R1 to R7 in Formula (1).

In —C($R_{01}$)=C($R_{02}$)—, —N=C($R_{02}$)—, and —C($R_{01}$)=N— each represented by A3 of Formula (6), the substituent represented by $R_{01}$ and $R_{02}$ each are synonymous with the substituent represented by R1 to R7 each in Formula (1).

In Formula (6), examples of a bidentate ligand represented by $P_1$-L1-$P_2$ include: phenylpyridine, phenylpyrazole, phenylimidazole, phenyltriazole, phenyltetrazole, pyrazabol, acetylacetone and picolinic acid.

Further, j1 represents an integer of 1 to 3, j2 represents an integer of 0 to 2, provided that the sum of j1 and j2 is 2 or 3. In particular, j2 is preferably 0.

In Formula (6), the transition metal element of Group 8 to Group 10 in the periodic table of the elements represented by $M_1$ is synonymous with the transition metal element of Group 8 to Group 10 in the periodic table of the elements represented by $M_1$ in Formula (5).

<<Compounds Represented by Formula (7)>>

One of the preferable embodiments of the compounds represented by Formula (6) of the present invention is the compound represented by the above-described Formula (7).

In Formula (7), the substituents represented by each of $R_{03}$, $R_{04}$, $R_{05}$, and $R_{06}$ each are synonymous with the substituents represented by R1 to R7 each in Formula (1).

A benzene ring is cited as a 6-membered aromatic hydrocarbon ring which is formed by Z1 combined with C—C in Formula (7).

These rings may further have a substituent represented by each of R1 to R7 in Formula (1).

In Formula (7), examples of a 5-membered or 6-membered aromatic heterocycle which is formed by Z1 combined with C—C include: an oxazole ring, an oxadiazole ring, an oxatriazole ring, an isoxazole ring, a tetrazole ring, a thiadiazole ring, a thiatriazole ring, an isothiazole ring, a thiophene ring, a furan ring, a pyrrole ring, a pyridine ring, a pyridazine ring, a pyrimidine ring, a pyrazine ring, a triazine ring, an imidazole ring, a pyrazole ring and a triazole ring.

These rings may further have a substituent represented by each of R1 to R7 in Formula (1).

In Formula (7), the bidentate ligand represented by $P_1$-L1-$P_2$ is synonymous with the bidentate ligand represented by $P_1$-L1-$P_2$ in Formula (5).

In Formula (7), the transition metal element of Group 8 to Group 10 in the periodic table of the elements represented by $M_1$ is synonymous with the transition metal element of Group 8 to Group 10 in the periodic table of the elements represented by $M_1$ in Formula (5).

<<Compounds Represented by Formula (8)>>

Further, among the compounds represented by Formula (7), the compounds represented by Formula (8) are preferable.

In Formula (8), the substituents represented by each of $R_{03}$, $R_{04}$, R95, $R_{06}$, and $R_{07}$ each are synonymous with the substituents represented by R1 to R7 each in Formula (1).

In Formula (8), the bidentate ligand represented by $P_1$-L1-$P_2$ is synonymous with the bidentate ligand represented by $P_1$-L1-$P_2$ in Formula (5).

In Formula (8), the transition metal element of Group 8 to Group 10 in the periodic table of the elements represented by $M_1$ is synonymous with the transition metal element of Group 8 to Group 10 in the periodic table of the elements represented by $M_1$ in Formula (5).

The compounds respectively represented by Formulas (5), (6), (7) and (8) of the present invention can be synthesized by referring to the following ways: by allowing to react a nitrogen containing compound or an imidazole compound with a corresponding halogenated compound as described in Eur. J. Chem, 2005, 1637-1643; and by allowing to react a corresponding amine and glyoxal, and an aldehyde with ammonium chloride as described in SYNTHESIS 2003, 17, 2661-2666.

Specific examples of a compound (it is also called as a metal complex) which are represented by any one of Formulas (5), (6), (7) and (8) of the present invention are shown below, however, the present invention is not limited to these.

D-1
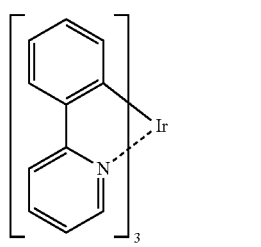

D-2
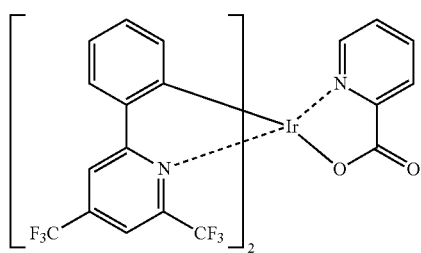

D-3
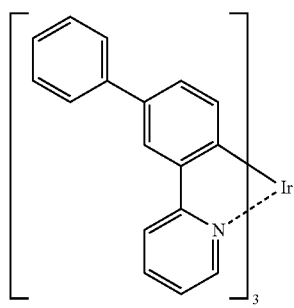

D-4
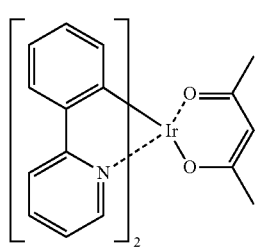

D-5
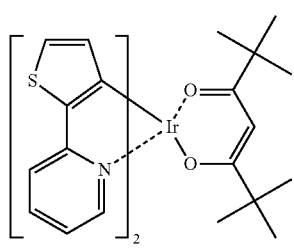

D-6
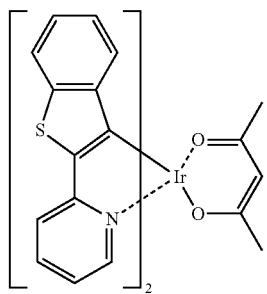

D-7
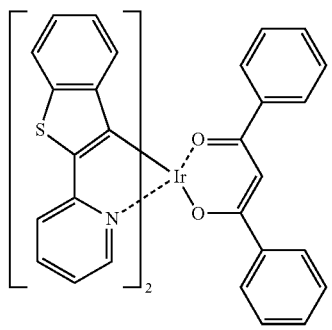

D-8
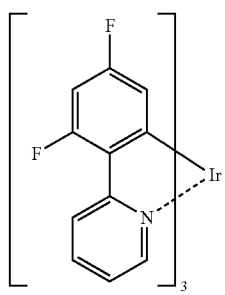

D-9
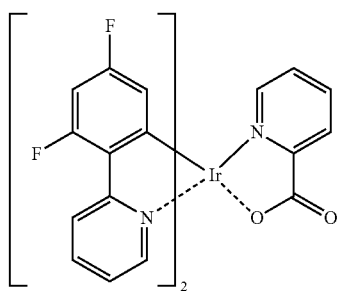

D-10
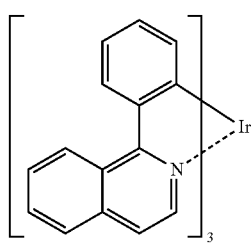

-continued
D-11
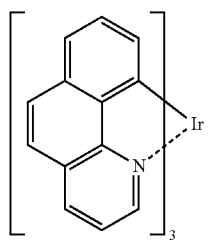
D-12
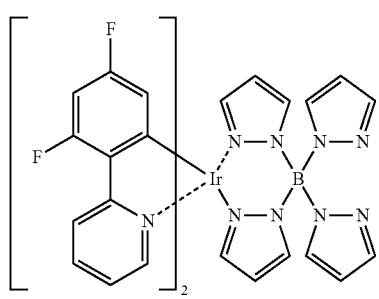
D-13
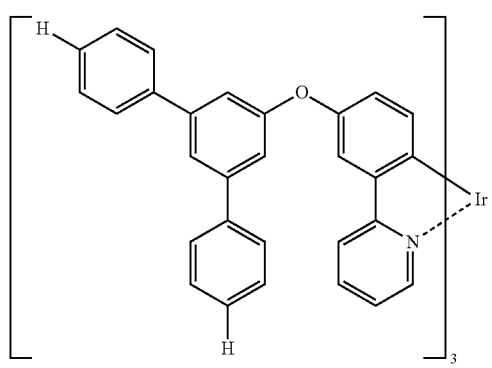
D-14
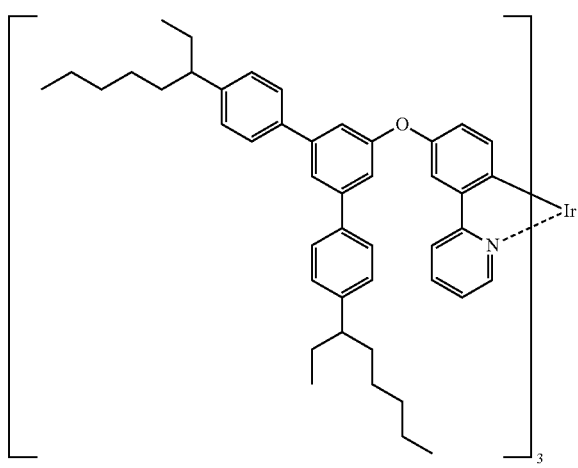
-continued
D-15
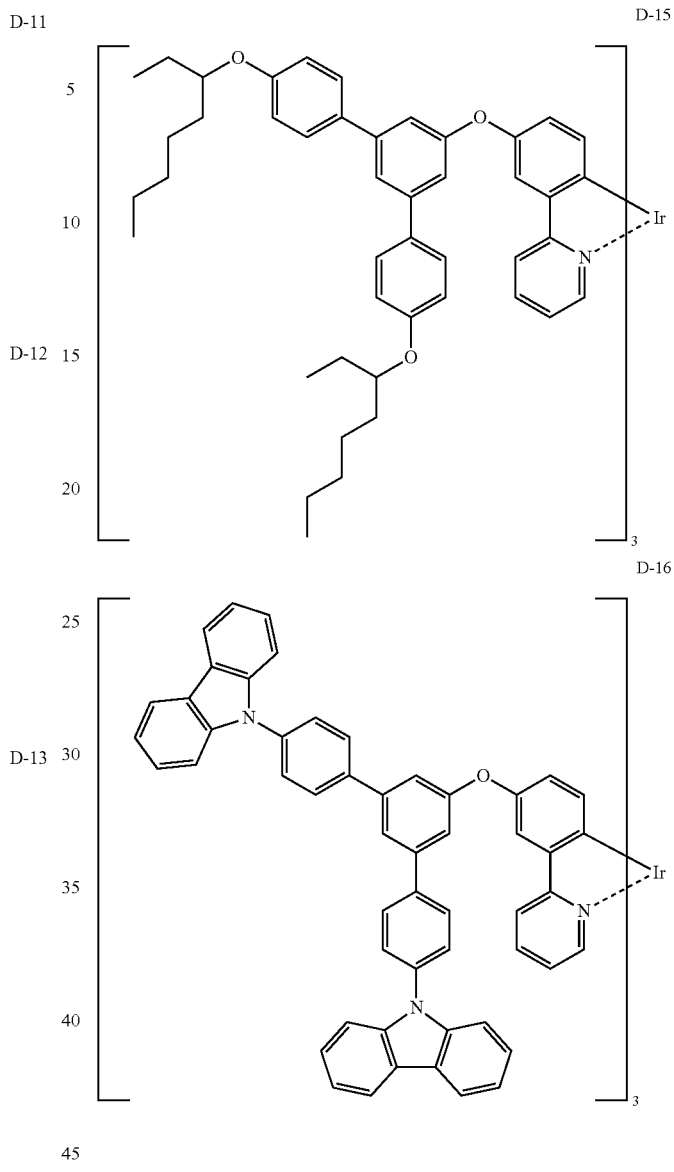
D-16
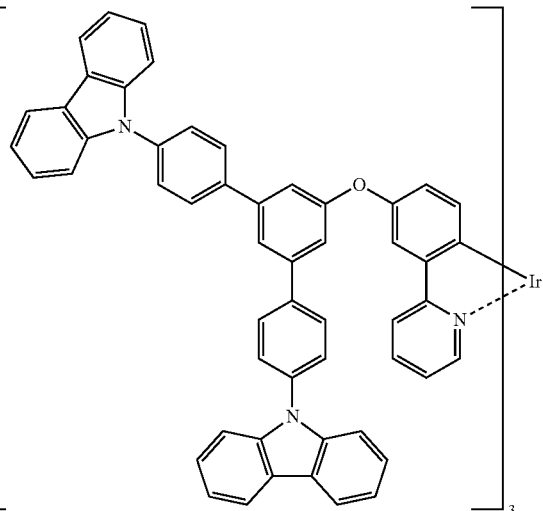
D-17
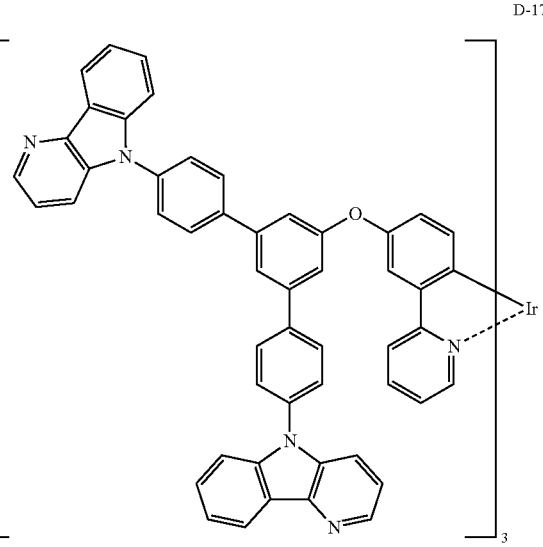

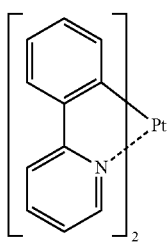
D-18
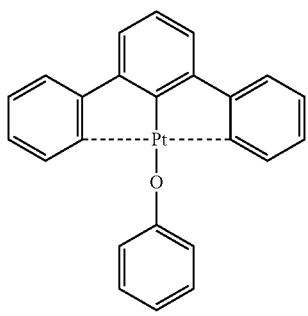
D-19
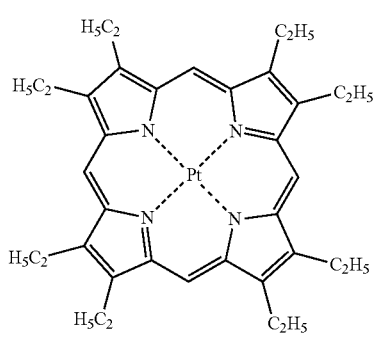
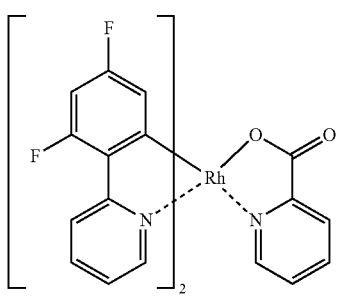
D-21
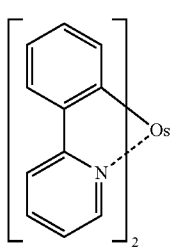
D-22
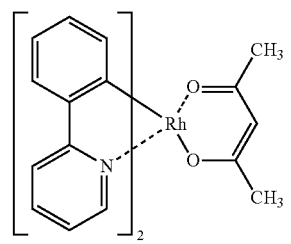
D-23
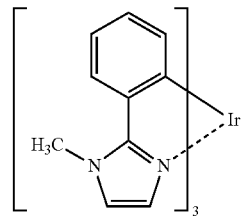
D-24
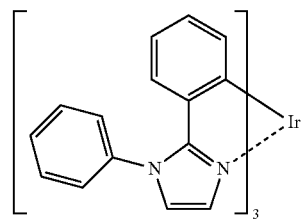
D-25
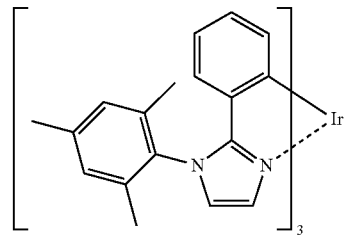
D-26
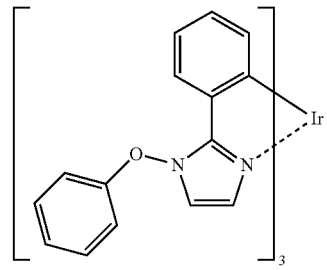
D-27
D-28

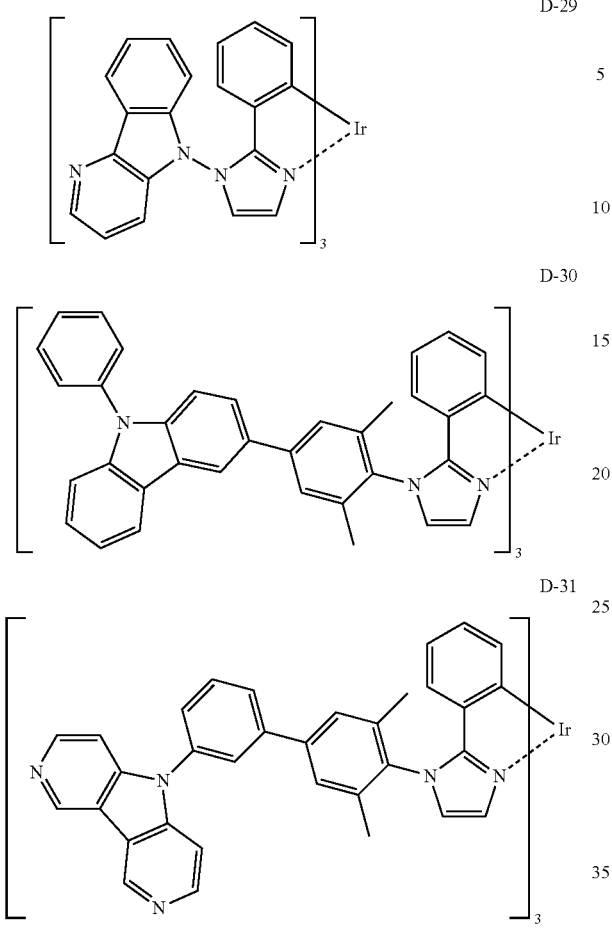
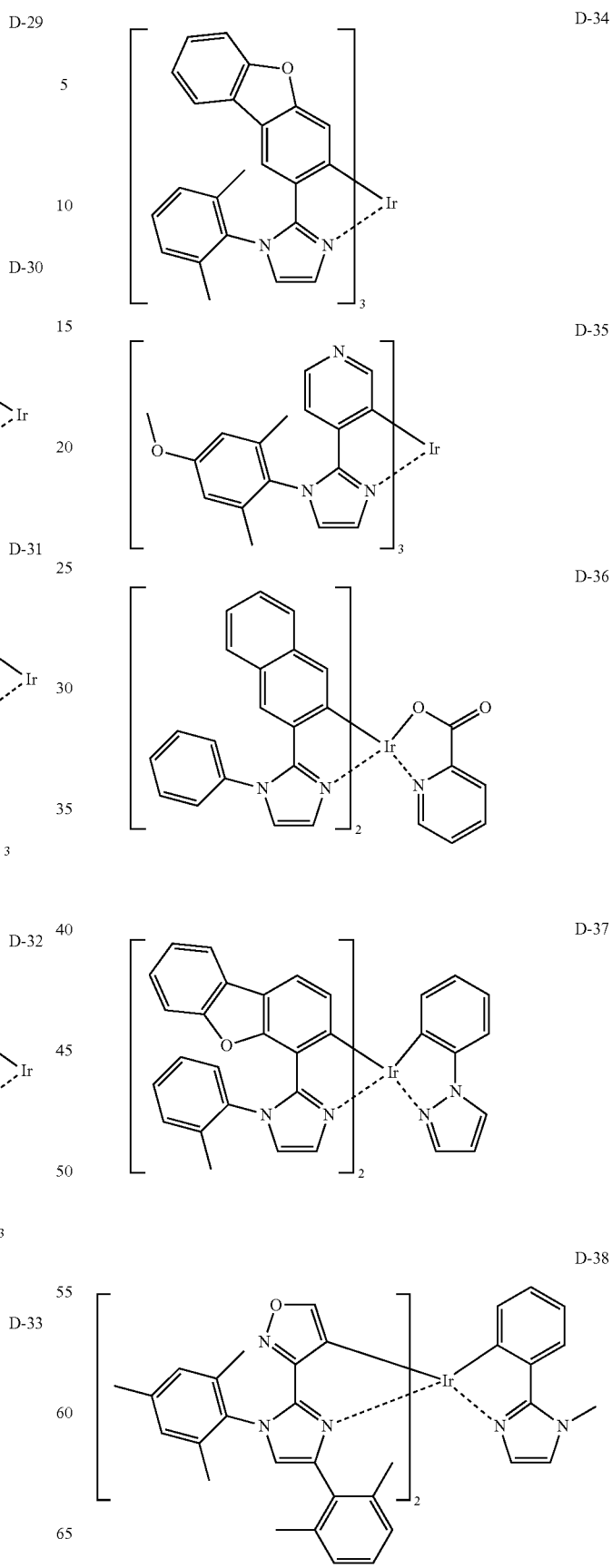

-continued

D-39
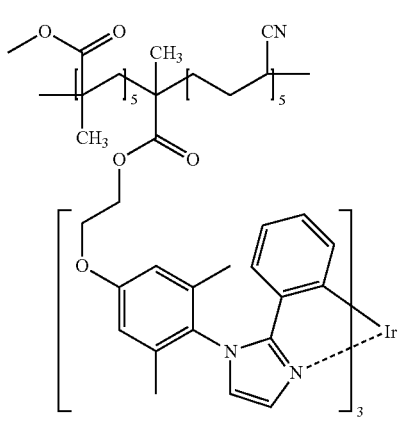

D-40
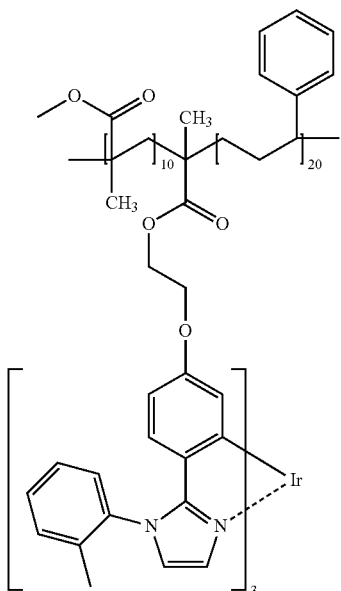

D-41
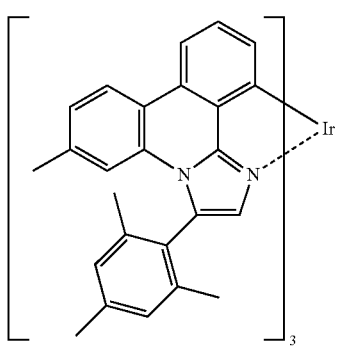

-continued

D-42
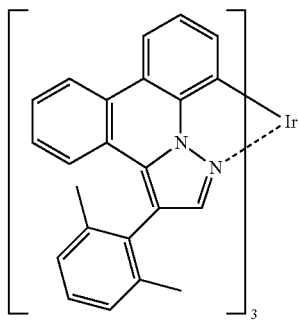

D-43
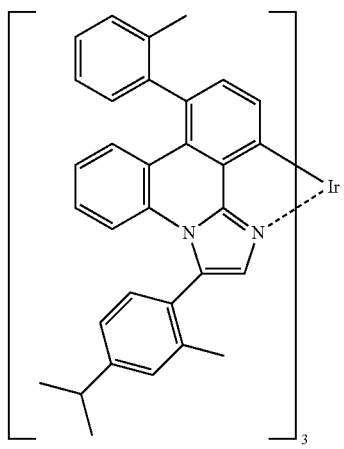

These metal complexes can be synthesized by applying a method described in such as Organic Letter, vol. 3, No. 16, pp. 2579-2581 (2001), Inorganic Chemistry vol. 30, No. 8, pp. 1685-1687 (1991), J. Am. Chem. Soc, vol. 123, p. 4304 (2001), Inorganic Chemistry vol. 40, No. 7, pp. 1704-1711 (2001), Inorganic Chemistry vol. 41, No. 12, pp. 3055-3066 (2002), New Journal of Chemistry, vol. 26, p. 1171 (2002), Organic Letters Vol. 18, No. 3, pp. 415-418 (2006), and reference documents described in these documents.

A representative synthetic example will be shown below.
<<Synthesis of Example Compound D-26>>

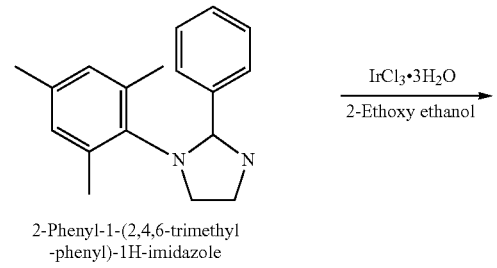

2-Phenyl-1-(2,4,6-trimethyl-phenyl)-1H-imidazole

-continued

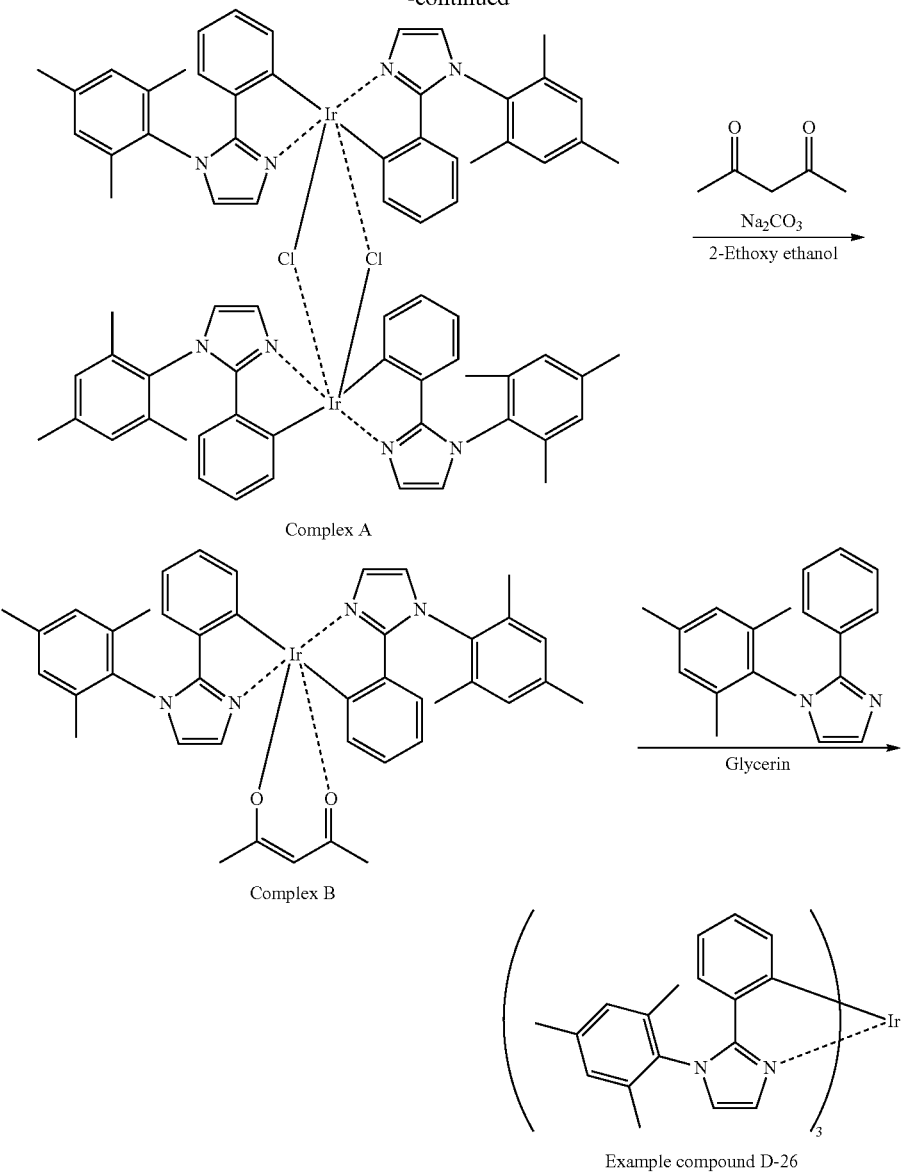

Complex A

Complex B

Example compound D-26

Under a nitrogen atmosphere, to a solution of 18 g (0.06861 mol) of 2-phenyl-(2,4,6-trimethylphenyl)-1H-imidazole dissolved in 350 ml of 2-ethoxy ethanol were added 8.1 g (0.02297 mol) of iridium chloride 3 hydrates and 100 ml of water. Then the mixture was refluxed for 5 hours under a nitrogen atmosphere.

The reaction solution was cooled and 500 ml of methanol was added. The precipitated crystals were separated by filtration. The obtained crystals were washed with methanol then dried to obtain 15.2 g (yield: 88.4%) of Complex A.

Under a nitrogen atmosphere, 14.5 g (0.00966 mol) of Complex A and 14.5 g of sodium carbonate were dispersed in 350 ml of 2-ethoxy ethanol. To this dispersion liquid was added 3.9 g (0.038955 mol) of acetyl acetone, then the mixture was refluxed for 2 hours under a nitrogen atmosphere.

After cooling the reaction solution, sodium carbonate and an inorganic salt were eliminated with reduced pressure filtration. The solvent was condensed under reduced pressure to obtain a solid. After adding 1 L of water to the obtained solid the mixture was dispersed. Then the solid was separated with filtration.

The obtained solid was further washed with a mixed solution of methanol and water (mixing ratio of 1 to 1) and then dried to obtain 14.7 g (yield: 93.6%) of Complex B.

Under a nitrogen atmosphere, 7.5 g (0.009214 mol) of Complex B and 6.0 g (0.02287 mol) of 2-phenyl-(2,4,6-trimethylphenyl)-1H-imidazole were dispersed in 400 ml of glycerin. The mixture was allowed to react at 150 to 160° C. for 2 hours under a nitrogen atmosphere. The reaction was terminated when Complex B was confirmed to be disappeared.

The reaction solution was cooled and 500 ml of methanol was added. The precipitated crystals were separated by filtration.

The obtained solid was further washed with methanol and then dried to obtain 7.1 g (yield: 78.9%) of crude product. This crude product was dissolved in a small amount of methylene chloride, and it was purified with silica gel column chromatography (using methylene chloride) to obtain 6.5 g (yield: 72.2%) of Example compound D-26.

The phosphorescent luminescent wavelength of Example compound D-26 in a solution was 466 ran (in 2-methyl tetrahydrofuran) using a spectrometer F-4500 (made by Hitachi, Ltd.).

<<Constituting Layers of Organic EL Element>>

The layers which constitute the organic EL element of the present invention will now be detailed. Preferred embodiments of the organic EL element of the present invention will be described below, however, the present invention is not limited to these, (i) anode/light emitting layer/electron transport layer/cathode (ii) anode/hole transport layer/light emitting layer/electron transport layer/cathode (iii) anode/hole transport layer/light emitting layer/hole blocking layer/electron transport layer/cathode (iv) anode/hole transport layer/light emitting layer/hole blocking layer/electron transport layer/cathode buffer layer/cathode (v) anode/anode buffer layer/hole transport layer/light emitting layer/hole blocking layer/electron transport layer/cathode buffer layer/cathode Further, there may be present a non-light emitting intermediate layer between the light emitting layers. The organic EL element of the present invention have preferably a white light emitting layer, and lighting devices employing these are preferred.

Each of the layers which constitute the organic EL elements of the present invention will now be detailed.

<<Electron Transport Layer>>

Although the compound represented by any one of Formulas (1), (2), (3) and (4) relating to the present invention is contained at least in an electron transport layer which is one of the constituting layers of the organic EL elements of the present invention, it may be contained in other constituting layers (which will be described later in detail).

An electron transport layer is composed of a material having a function to transfer an electron, and an electron injection layer and a hole blocking layer are included in an electron transport layer in a broad meaning. A single layer or plural layers of an electron transport layer may be provided.

The electron transport layer is only required to have a function of transporting electrons ejected from the cathode to the light emitting layer. As materials to form an electron transport layer, any of the conventional compounds may be selected and they can be jointly employed.

Examples of them (hereinafter, they are called as an electron transport material) include: a nitro-substituted fluorene derivative, a diphenylquinone derivative, a thiopyradineoxide derivative, heterocyclic tetracarboxylic acid anhydride such as naphthalene perylene, carbodiimide, a fluorenylidenemethane derivative, anthraquinonedimethane, an anthrone derivative, an oxadiazole derivative, a carboline derivative, and a compound in which at least one of carbon atoms in a hydrocarbon ring constituting the carboline ring are replaced with one nitrogen atoms.

Further, as examples of an oxadiazole derivative described above, the following compounds can be used as an electron transport material: a thiadiazole derivative in which an oxygen atom in the oxadiazole ring is replaced with a sulfur atom; and a quinoxaline derivative which contains a quinoxaline ring known as an electron withdrawing group.

Polymer materials, in which these materials are introduced in a polymer chain or these materials form the main chain of polymer, can be also utilized.

Further, a metal complex of a 8-quinolinol derivative such as tris(8-quinolinol)aluminum ($Alq_3$), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum and bis(8-quinolinol)zinc (Znq); and metal complexes in which a central metal of the aforesaid metal complexes is substituted by In, Mg, Cu, Ca, Sn, Ga or Pb, can be also utilized as an electron transport material.

Further, metal-free or metal phthalocyanine, or a compound whose terminal is substituted by an alkyl group or a sulfonic acid group, can be preferably utilized as an electron transport material.

An inorganic semiconductor such as an n-type-Si and an n-type-SiC can be also utilized as an electron transport material.

When fee electron transport layer is adjacent to the cathode, the electron transport layer may contain a metal or the metal element compound which belongs to Group 1 or Group 2 of the periodic table of elements and exhibits a standard electrode potential larger than −3 V vs. SHE in a system of the metal ion ($M^{n+}$)/the metal (M).

The electron transport layer can be preferably prepared by forming a thin layer made of the above-described electron transport material with a vacuum evaporation method or a wet preparation method. A wet preparation method is also called as a wet process, and examples of this include: a spin coating method, a cast method, a die coating method, a blade coating method, a roll coating method, an inkjet method, a printing method, a spray coating method, a curtain coating method, and a LB method (Langmuir Blodgett method).

The preparation method of the constituting layers of the organic EL element will be described in detain in the portion of preparation of an organic EL element.

The layer thickness of the electron transport layer of the present invention is not specifically limited; however, it is generally 5 nm-5,000 nm, and preferably it is 5 nm-200 nm. This electron transport layer may be a single layer structure containing of one or more types of the above described materials.

Next, there will be listed specific example compounds (electron transport materials) known in the art and preferably used in the electron transport layer of the white light emitting organic EL element. However, the present invention is not limited to them.

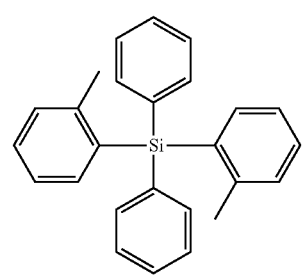

ET-1

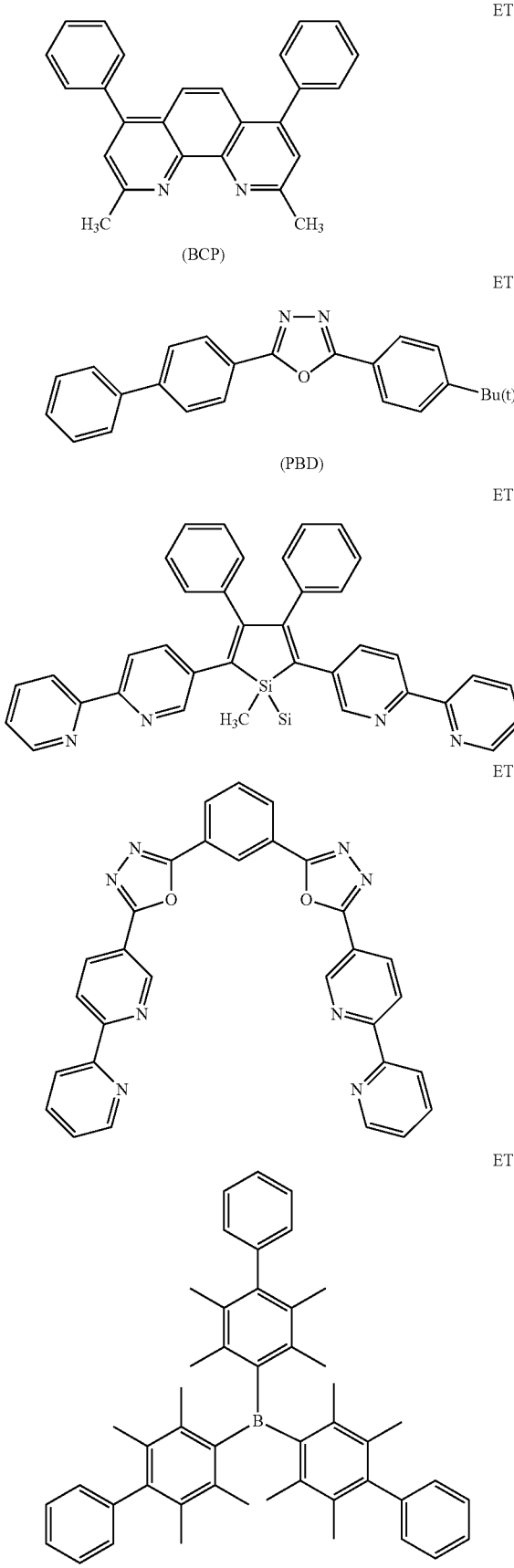

<<Light Emitting Layer>>

The light emitting layer of the present invention is a layer, which emits light via recombination of electrons and holes injected from an electrode or a layer such as an electron transport layer or a hole transport layer. The light emission portion may be present either within the light emitting layer or at the interface between the light emitting layer and an adjacent layer thereof.

The total thickness of the light emitting layer is not particularly limited. However, in view of the layer homogeneity, the minimization of application of unnecessary high voltage during light emission, and the stability enhancement of the emitted light color against the drive electric current, the layer thickness is regulated preferably in the range of 2 nm-5 μm, more preferably in the range of 2 nm-200 nm, but most preferably in the range of 5 nm-100 nm.

The light emitting layer can be prepared by forming a thin layer made of a light emitting dopant and a host compound, which will be described later, with a vacuum evaporation method or a wet preparation method. A wet preparation method is also called as a wet process, and examples of this include: a spin coating method, a cast method, a die coating method, a blade coating method, a roll coating method, an inkjet method, a printing method, a spray coating method, a curtain coating method, and a LB method (Langmuir Blodgett method). When using the compound of the present invention for a light emitting layer, preparation with a wet process is preferable.

It is preferable that the light emitting layer of the organic EL element of the present invention incorporates at least two kinds of compounds: one is a light emitting dopant (a phosphorescent emitting dopant (or it is called as a phosphorescence dopant or a phosphorescence emitting dopant group) or a fluorescent dopant) and the other is a light emitting host compound.

(Light Emitting Dopant Compound)

The light emitting dopant compound (it may be called as the light emitting dopant) of the present invention will now be described.

As light emitting dopants according to the present invention, it can be employed fluorescent dopants (also referred to as fluorescent compounds) and phosphorescent dopants (also referred to as phosphorescent emitting materials, phosphorescent compounds or phosphorescence emitting compounds).

(Phosphorescent Dopant (Also Referred to as Phosphorescence Emitting Dopant))

A phosphorescence dopant of the present invention will be described.

The phosphorescent dopant of the present invention is a compound, wherein emission from an excited triplet state thereof is observed, specifically, emitting phosphorescence at room temperature (25° C.) and exhibiting a phosphorescence quantum yield of at least 0.01 at 25° C. The phosphorescence quantum yield is preferably at least 0.1.

The phosphorescence quantum yield can be determined via a method described in page 398 of Bunko II of Dai 4 Han Jikken Kagaku Koza 7 (Spectroscopy U of 4th Edition Lecture of Experimental Chemistry 7) (1992, published by Maruzen Co., Ltd.). The phosphorescence quantum yield in a solution can be determined using appropriate solvents. However, it is only necessary for the phosphorescent dopant of the present invention to exhibit the above phosphorescence quantum yield (0.01 or more) using any of the appropriate solvents.

Two lands of principles regarding emission of a phosphorescent dopant are cited. One is an energy transfer-type, wherein carriers recombine on a host compound on which the carriers are transferred to produce an excited state of the host compound, and then via transfer of this energy to a phosphorescent dopant, emission from the phosphorescence-emitting dopant is realized. The other is a carrier trap-type, wherein a phosphorescence-emitting dopant serves as a carrier trap and then carriers recombine on the phosphorescent dopant to generate emission from the phosphorescent dopant. In each case, the excited state energy of the phosphorescent dopant is required to be lower than that of the host compound.

The organic EL element of the present invention has at least one light emitting layer containing a phosphorescence emitting organic metal complex (it is also called as a phosphorescence emitting dopant or a phosphorescence dopant). As the phosphorescence emitting organic metal complex, it is preferable that the organic EL element of the present invention contains a compound represented by any one of Formulas (5), (6), (7), and (8).

Further, in the compound represented by any one of Formulas (5), (6), (7) and (8), $M_1$ represents a transition metal element of Group 8 to Group 10 in the periodic table of the elements. In particular, $M_1$ is preferably iridium.

The light emitting layer of the present invention may further incorporate the compounds described in the following patent documents.

The patent documents are: WO 00/70655 pamphlet, JP-A Nos. 2002-280178, 2001-181616, 2002-280179, 2001-181617, 2002-280180, 2001-247859, 2002-299060, 2001-313178, 2002-302671, 2001-345183 and 2002-324679, WO 02/15645 pamphlet, JP-A Nos. 2002-332291, 2002-50484, 2002-322292 and 2002-83684, Japanese Translation of PCT International Application Publication No. 2002-540572, JP-A Nos. 2002-117978, 2002-338588, 2002-170684 and 2002-352960, WO 01/93642 pamphlet, JP-A Nos. 2002-50483, 2002-100476, 2002-173674, 2002-359082, 2002-175884, 2002-363552, 2002-184582 and 2003-7469, Japanese Translation of PCT International Application Publication No. 2002-525808, JP-A 2003-7471, Japanese Translation of PCT International Application Publication No. 2002-525833, JP-A Nos. 2003-31366, 2002-226495, 2002-234894, 2002-235076, 2002-241751, 2001-319779, 2001-319780, 2002-62824, 2002-100474, 2002-203679, 2002-343572 and 2002-203678.

(Fluorescent Dopants (Also Referred to as Fluorescent Compounds))

As fluorescent dopants, listed are compounds exhibiting a high fluorescent quantum efficiency such as: coumarin based dyes, pyran based dyes, cyanine based dyes, croconium based dyes, squarylium based dyes, oxobenzanthracene based dyes, fluorescein based dyes, Rhodamine based dyes, pyrylium based dyes, perylene based dyes, stilbene based dyes, polythiophene based dyes, rare earth complex based fluorescent materials, or laser dyes.

Moreover, two or more sorts of compounds may be combined together and used for the light emitting dopants of the present invention. It is possible to use in combination with phosphorescence dopants each having a different structure or to use in combination of a fluorescence dopant and a phosphorescence dopant.

(Light Emitting Host Compounds (Also Referred to as Light Emitting Hosts))

"Host compounds", as described in the present invention, are defined as compounds, incorporated in a light emitting layer, which result in a weight ratio of at least 20% in the above layer and also result in a phosphorescent quantum yield of the phosphorescence emission of less than 0.1 at room temperature (25° C.). Preferably, the phosphorescent quantum yield is less than 0.01. Further, among the compounds incorporated in the light emitting layer, it is preferable that the weight ratio of the host compound in the aforesaid layer is at least 20%.

Structures of the light emitting host employed in the present invention are not particularly limited. The conventionally known host compounds in organic EL elements can be used. Representative compounds include those having a basic skeleton such as carbazole derivatives, triarylamine derivatives, aromatic compound derivatives, nitrogen-containing heterocyclic compounds, thiophene derivatives, furan derivatives, oligoarylene compounds, carboline derivatives, or diazacarbazole derivatives (here, "a diazacarbazole derivative" indicates a structure in which at least one of the carbon atoms in a hydrocarbon ring constituting the carboline ring is replaced with a nitrogen atom).

A known light emitting host (or emission host) which may be used in the present invention is preferably a compound having a hole transporting ability and an electron transporting ability, as well as preventing elongation of an emission wavelength and having a high Tg (a glass transition temperature).

It may be used an emission host compound of the present invention singly or it may be used in combination with plural host compounds, which may be other host compound of the present invention or a known host compound.

It is possible to control the transfer of charges by making use of a plurality of host compounds, which results in high efficiency of an organic EL element.

In addition, it is possible to mix a different emission lights by making use of a plurality of known phosphorescent dopants as described above. Any required emission color can be obtained thereby.

Further, an emission host used in the present invention may be either a low molecular weight compound or a polymer compound having a repeating unit, in addition to a low molecular weight compound provided with a polymerizing group such as a vinyl group and an epoxy group (an polymerizable emission host). These compounds may be used singly or in combination of two or more compounds.

As specific examples of an emission host compounds, the compounds described in the following Documents are preferable.

For example, JP-A Nos. 2001-257076, 2002-308855, 2001-313179, 2002-319491, 2001-357977, 2002-334786, 2002-8860, 2002-334787, 2002-15871, 2002-334788, 2002-3056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837.

Specific exemplified compounds used as an emission host in the light emitting layer of the organic EL element of the present invention are given below, however, the present invention is not limited to these.

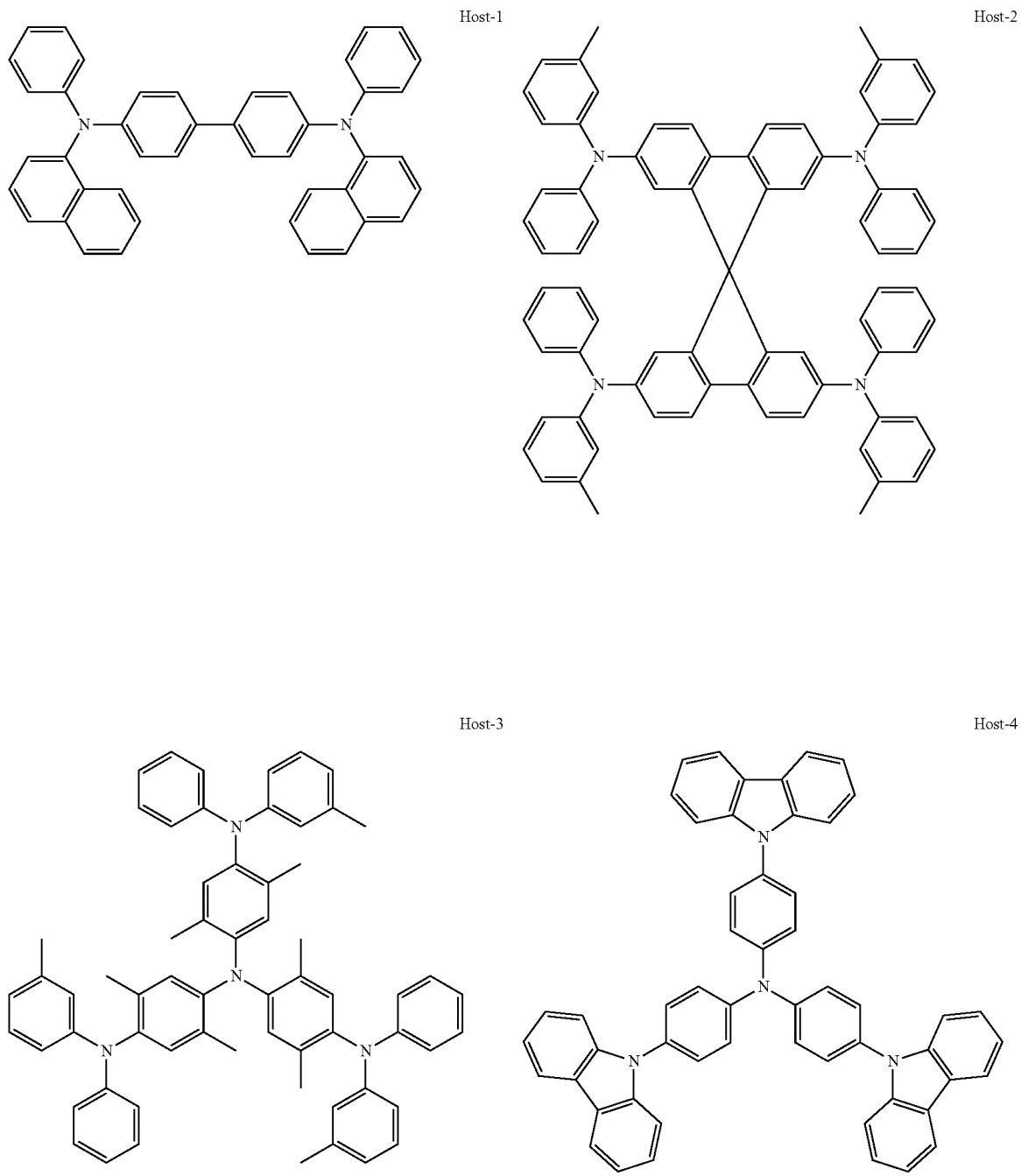

-continued
Host-5
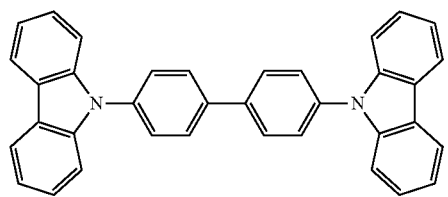
Host-6
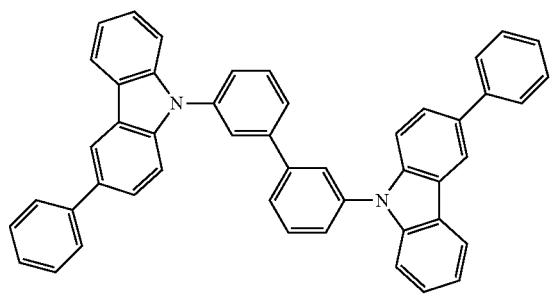
Host-7
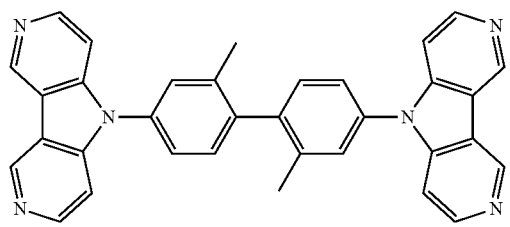
Host-8
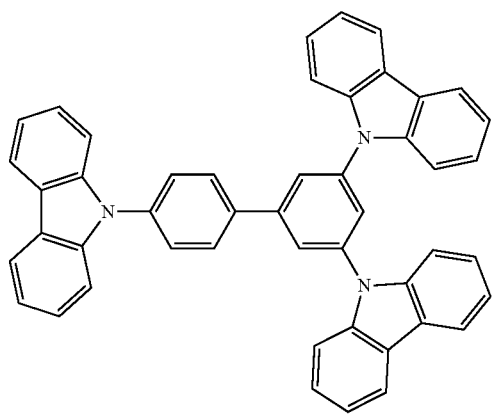
Host-9
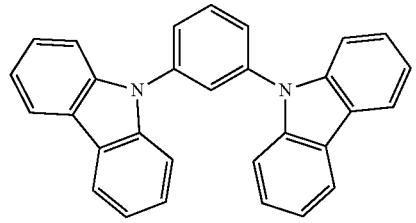
Host-10
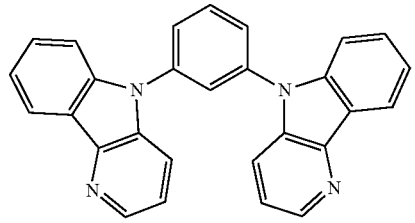
Host-11
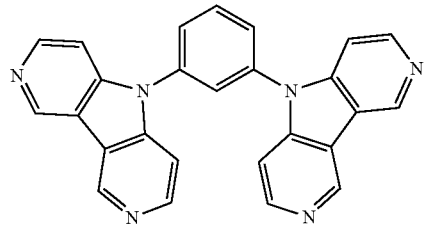
Host-12
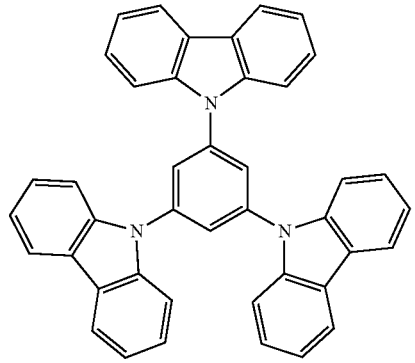

-continued
Host-13
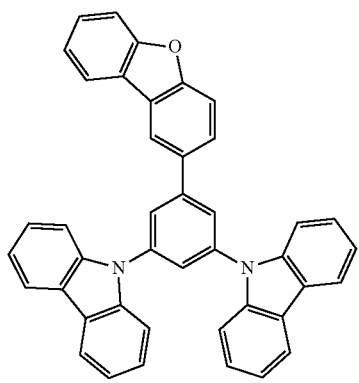
Host-14
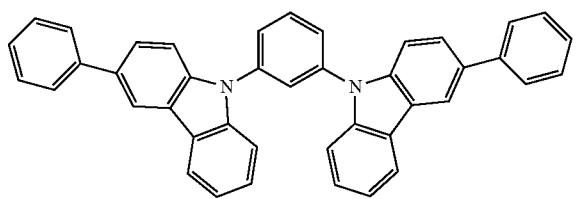
Host-15
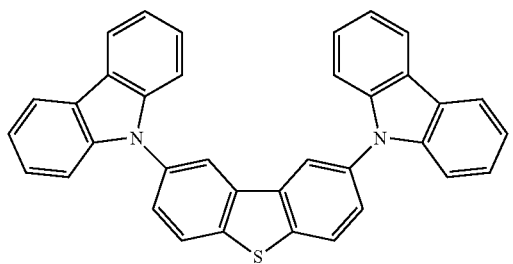
Host-16
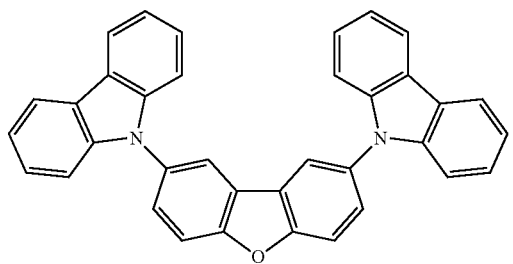
Host-17
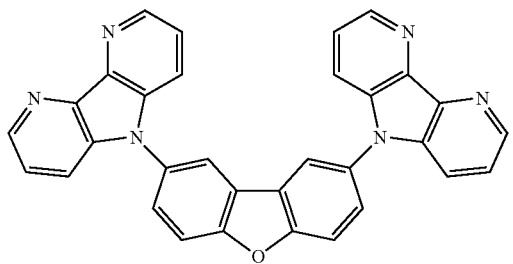
Host-18
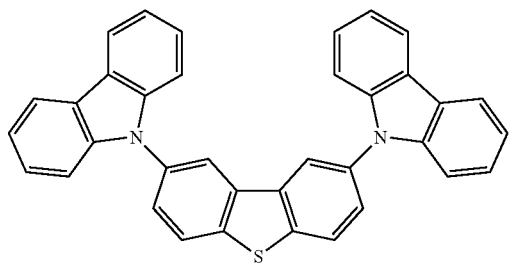
Host-19
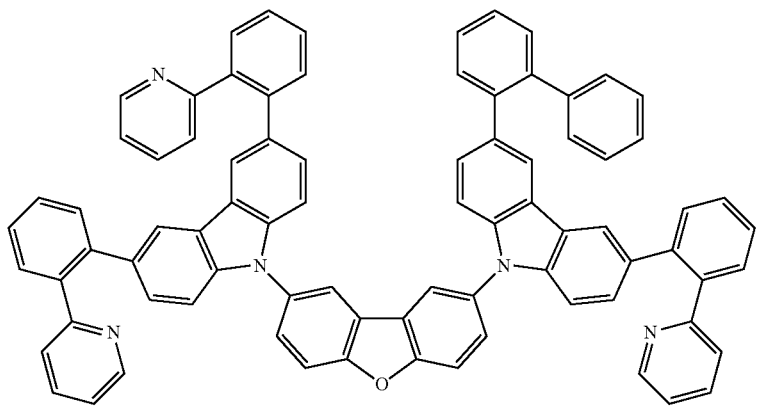

-continued
Host-20
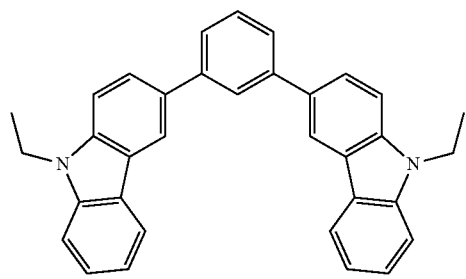
Host-21
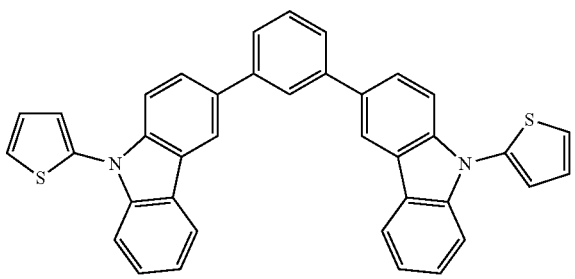
Host-22
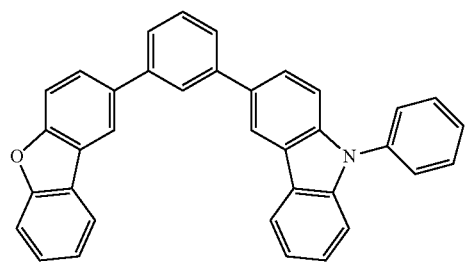
Host-23
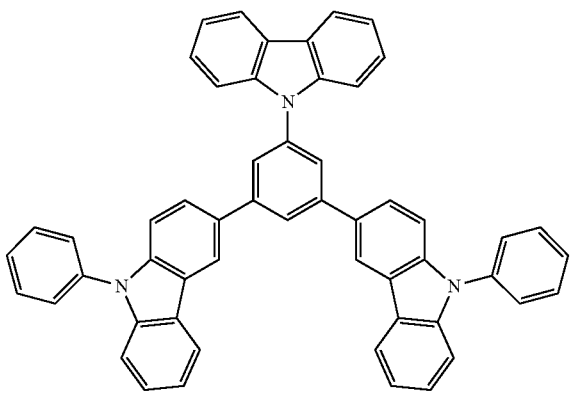
Host-24
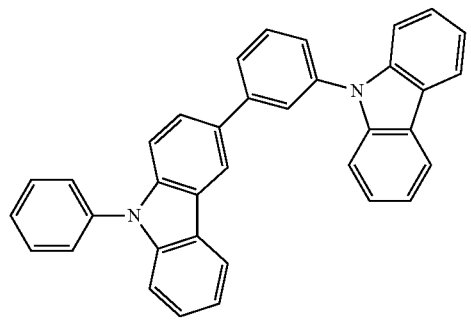
Host-25
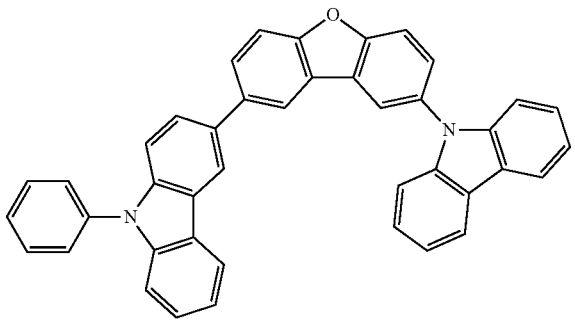
Host-26
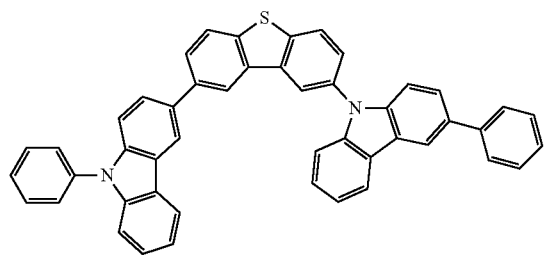
Host-27
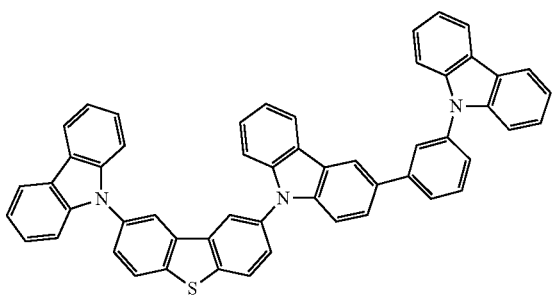

Host-28
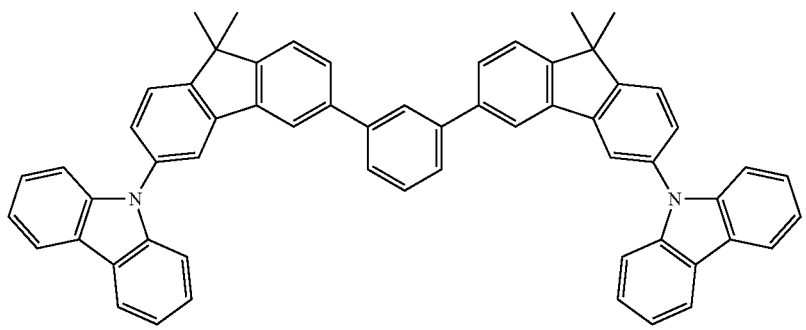
Host-29
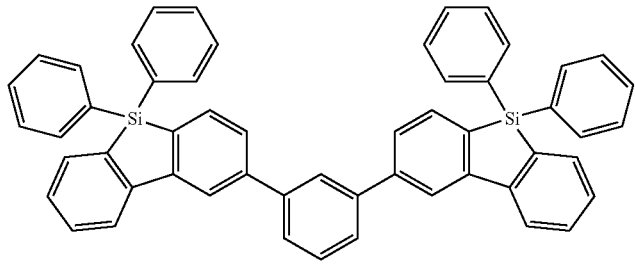
Host-30
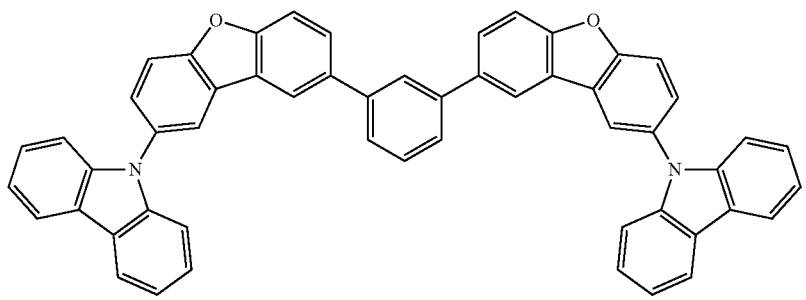
Host-31
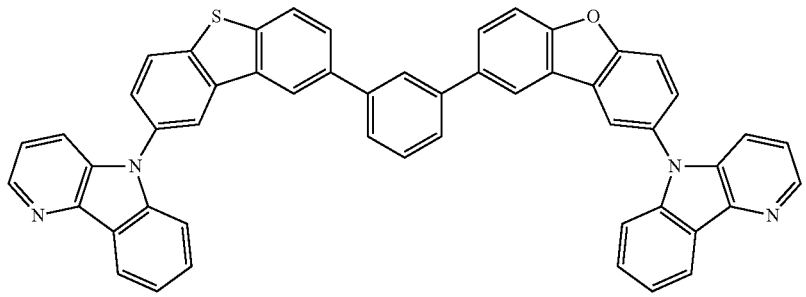
Host-32
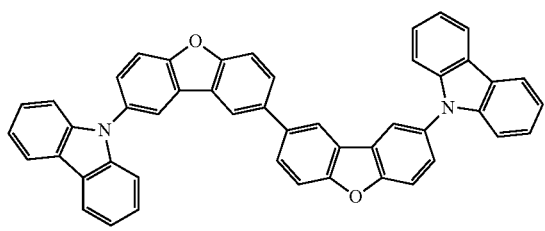
Host-33
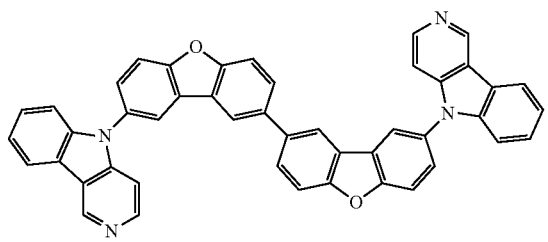

-continued
Host-34
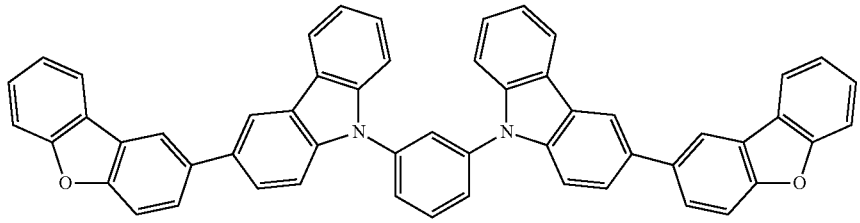
Host-35
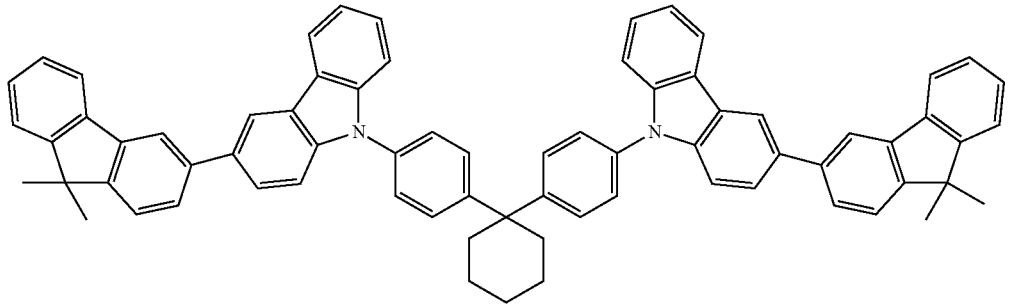
Host-36
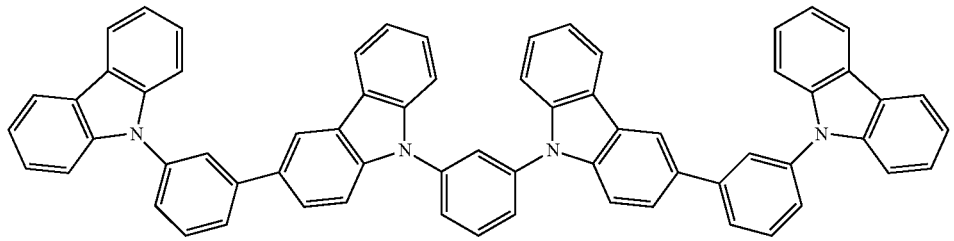
Host-37
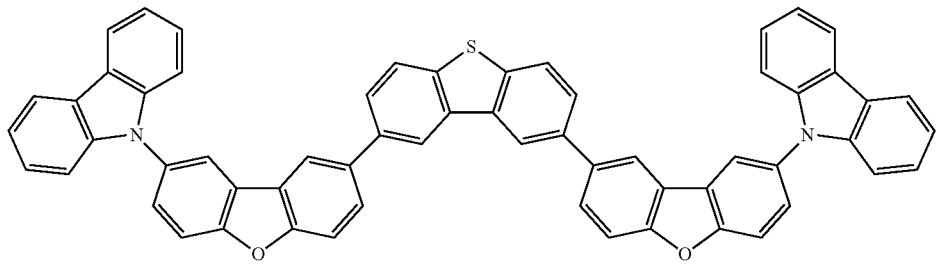
Host-38
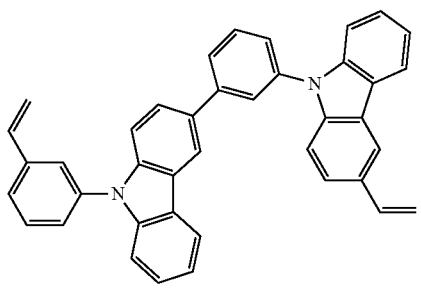
Host-39
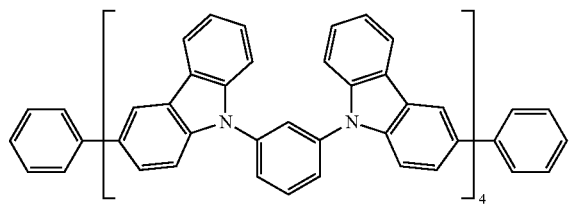

Host-40
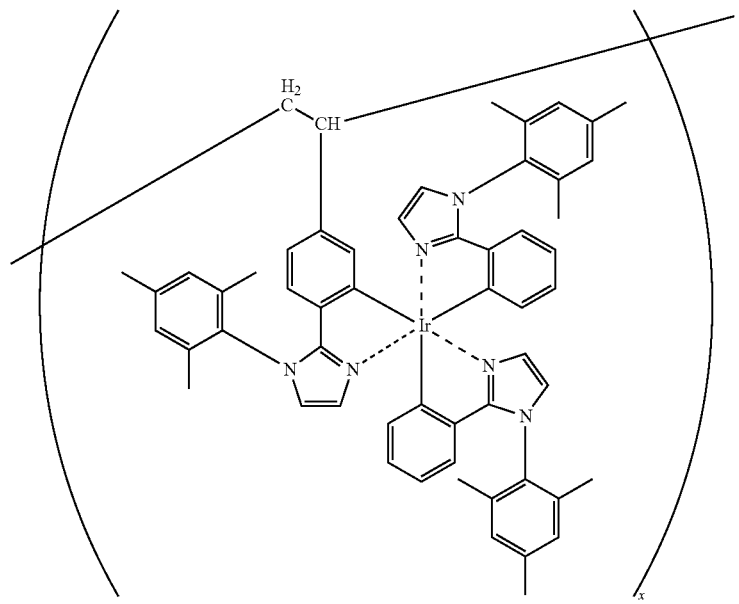
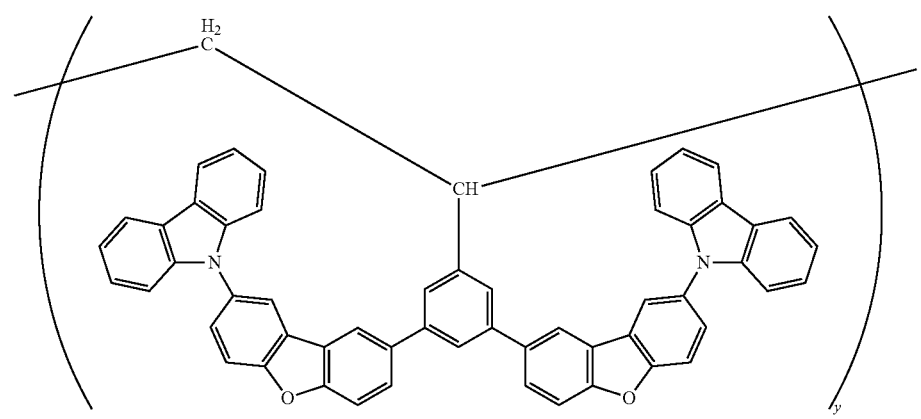
x:y = 1:10
random co-polymer

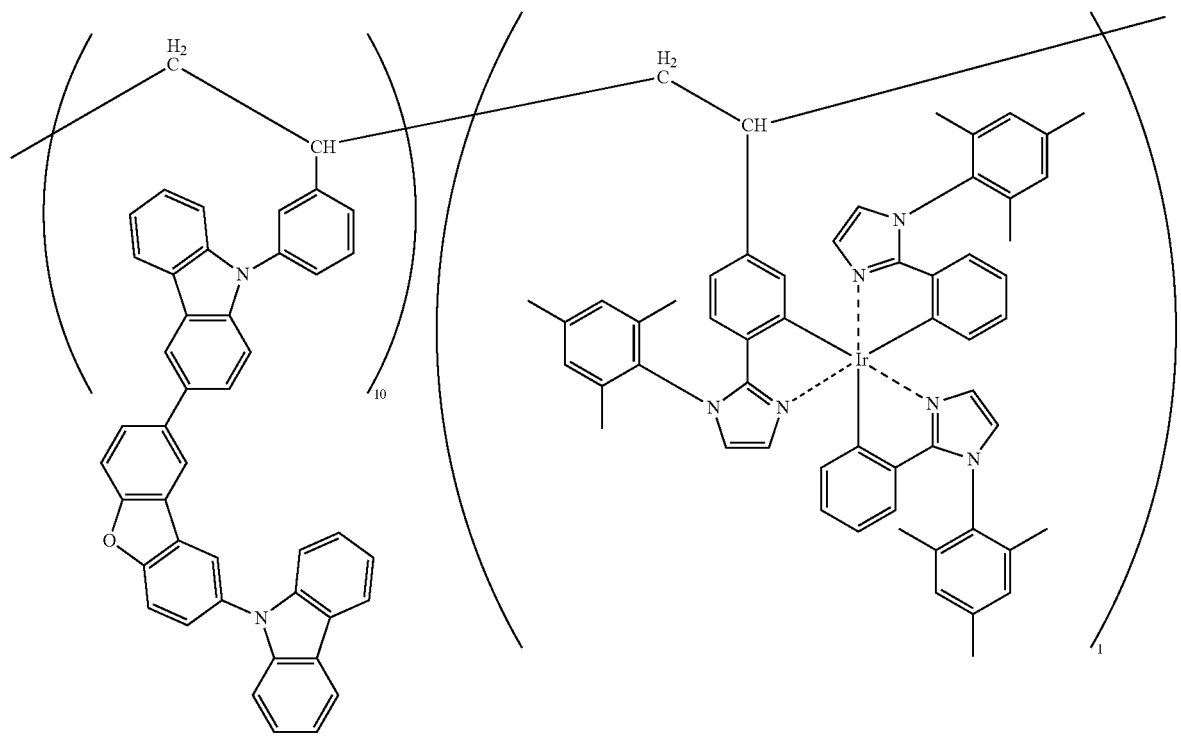
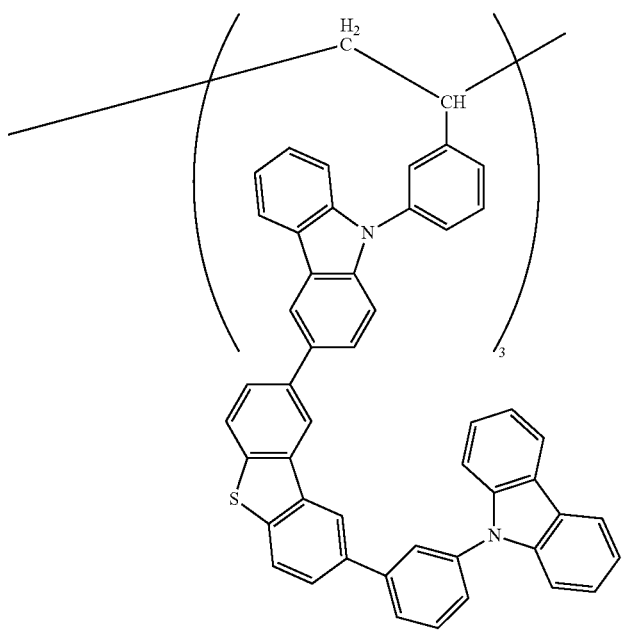

-continued
Host-42
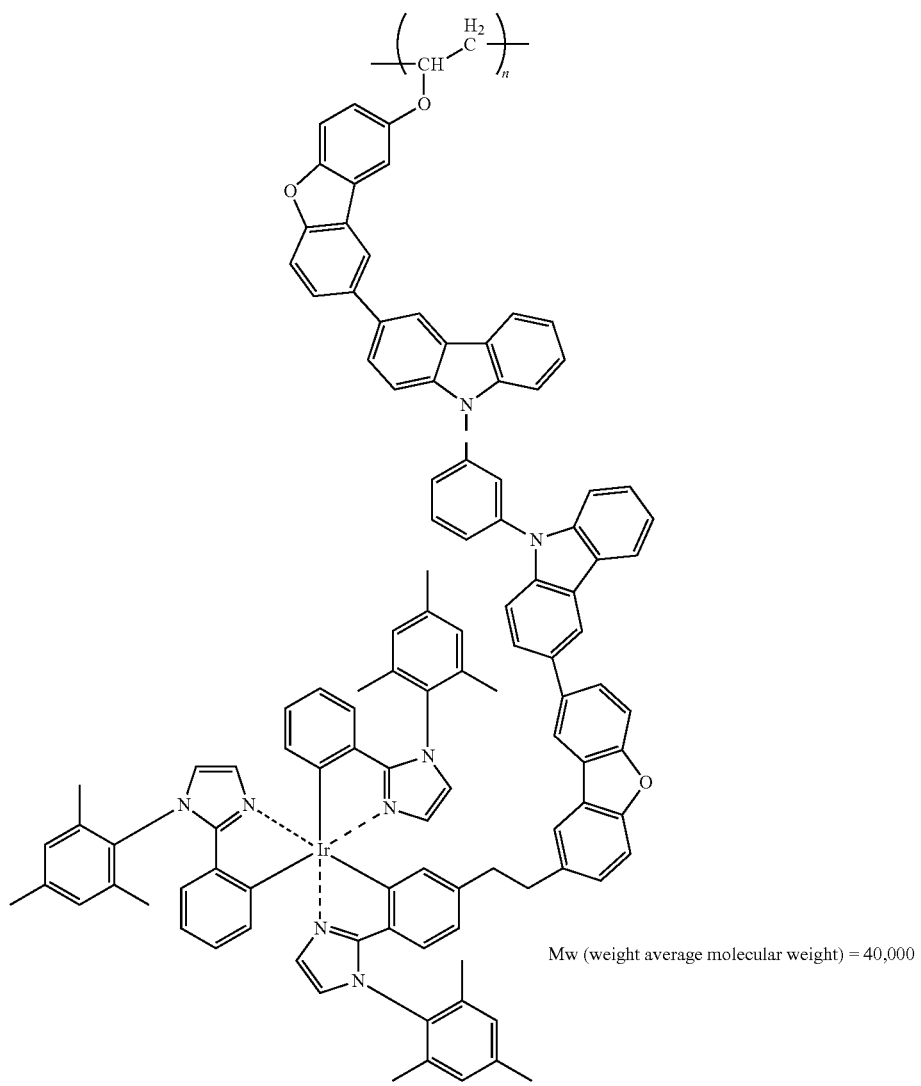
Mw (weight average molecular weight) = 40,000
Host-43
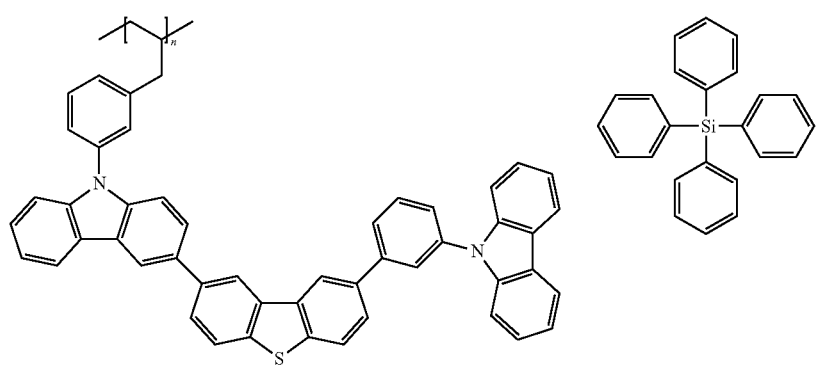
Mw (weight average molecular weight) = 100,000
Host-44

Host-45
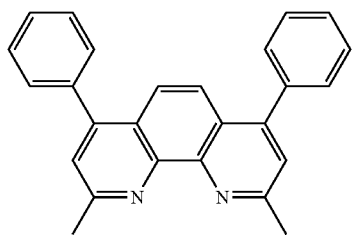
Host-46
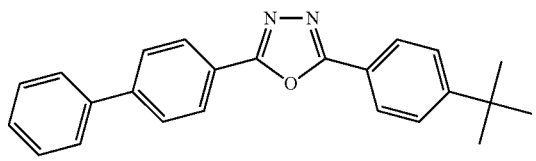
Host-47
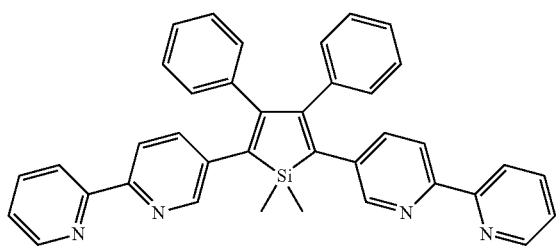
Host-48
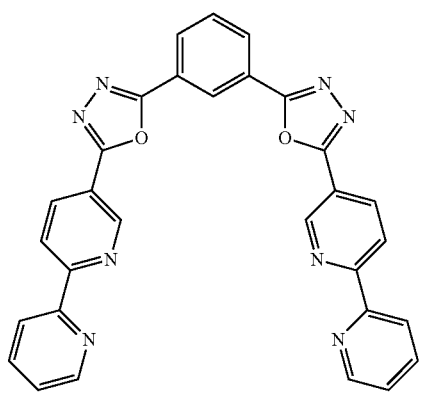
Host-49
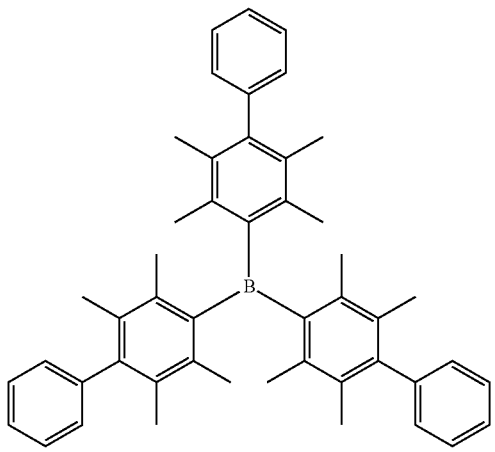
Host-50
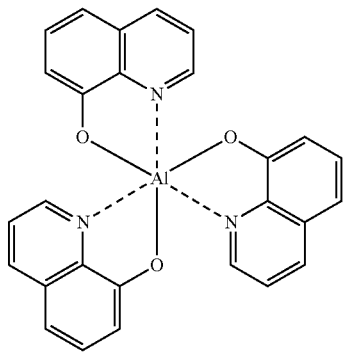
Host-51
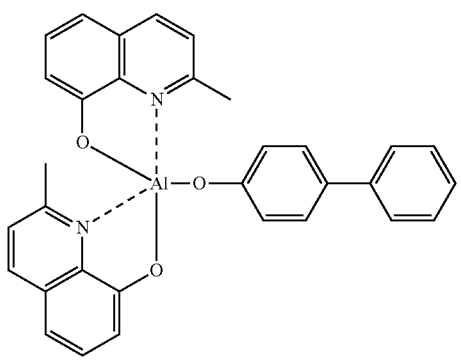

<<Cathode>>

On the other hand, as a cathode according to the present invention, metal, alloy, a conductive compound and a mixture thereof, which have a small work function (not more than 4 eV), are utilized as an electrode substance. Specific examples of such an electrode substance includes such as sodium, sodium-potassium alloy, magnesium, lithium, a magnesium/copper mixture, a magnesium/silver mixture, a magnesium/aluminum mixture, a magnesium/indium mixture, an aluminun/aluminum oxide ($Al_2O_3$) mixture, indium, a lithium/aluminum mixture and rare earth metal.

Among them, with respect to an electron injection property and durability against such as oxidation, preferable are: a mixture of electron injecting metal (which belongs to Group 1 or Group 2 of the periodic table of elements and exhibits a standard electrode potential larger than −3 V vs. SHE in a system of the metal ion ($M^{n+}$)/the metal (M) or a metal compound thereof with the second metal which is stable metal having a work function larger than electron injecting metal; or only the second metal. Examples are: a magnesium/silver mixture, a magnesium/aluminum mixture, a magnesium/indium mixture, an potassium/aluminum mixture and aluminum.

As for a cathode, these electrode substances may be made into a thin layer by a method such as evaporation or spattering. Further, the sheet resistance as a cathode is preferably not more than a few hundreds $\Omega/\square$ and the layer thickness is generally selected in a range of 10 nm-5 $\square$m and preferably of 50 nm-200 nm. Herein, to transmit emission, either one of an anode or a cathode of an organic EL element is preferably transparent or translucent to improve the emission luminance.

Further, after forming, on the cathode, the above metals at a film thickness of 1 nm-20 nm, it is possible to prepare a transparent or translucent cathode in such a manner that electrically conductive transparent materials are prepared thereon By applying the above, it is possible to produce an element in which both anode and cathode are transparent.

<Injection Layer: Electron Injection Layer (Cathode Buffer Layer), Hole Injection Layer>

An injection layer is appropriately provided and includes an electron injection layer and a hole injection layer, which may be arranged between an anode and an emitting layer or a positive transfer layer, and between a cathode and an emitting layer or an electron transport layer, as described above.

An injection layer is a layer which is arranged between an electrode and an organic layer to decrease an operating voltage and to improve an emission luminance, which is detailed in volume 2, chapter 2 (pp. 123-166) of "Organic EL Elements and Industrialization Front thereof (Nov. 30, 1998, published by N. T. S Corp.)", and includes a hole injection layer (an anode buffer layer) and an electron injection layer (a cathode buffer layer).

An anode buffer layer (a hole injection layer) is also detailed in such as JP-A Nos. 945479, 9-260062 and 8-288069, and specific examples include such as a phthalocyanine buffer layer comprising such as copper phthalocyanine, an oxide buffer layer comprising such as vanadium oxide, an amorphous carbon buffer layer, and a polymer buffer layer employing conductive polymer such as polyaniline (or called as emeraldine) or polythiophene.

Examples of a cathode buffer layer (an electron injection layer) include: a metal buffer layer made of such as strontium and aluminum; an oxide buffer layer made of such as aluminum oxide; a metal or metal compound buffer layer made of such as potassium fluoride or calcium fluoride containing an element which belongs to Group 1 or Group 2 of the periodic table of elements and exhibits a standard electrode potential larger than −3V vs. SHE in a system of the metal ion ($M^{n+}$)/the metal (M)).

The above-described buffer layer (injection layer) is preferably a very thin layer, and the layer thickness is preferably in a range of 0.1 nm-5 $\square$m although it depends on a raw material.

The organic EL element of the present invention is characterized in that: in the cathode or in the composing layer which is located in the position adjacent to the above-described cathode (for example, an electron injection layer (a cathode buffer layer)), there is contained a metal or a metal compound which belongs to Group 1 or Group 2 of the periodic table of elements, and exhibits a standard electrode potential larger than −3 V vs. SHE in a system of the metal ion ($M^{n+}$)/the metal (M).

Here, a metal compound indicates a chloride, a complex or an organic metal compound.

A standard electrode potential $E^0$ in the system of [$M^{n+}$/M] of the present invention is an electrode potential in an aqueous solution at 25° C. having an activity of 1 for all of the solutes with respect to a standard hydrogen electrode. It can be referred to the values described, for example, in Table 12•46 at page II-474 of "Chemical Handbook, Fundamental part II, revised $3^{rd}$ edition" edited by Japan Chemical Society.

Further, as a metal or a metal compound of the present invention which belongs to Group 1 or Group 2 of the periodic table, and exhibits a standard electrode potential larger than −3 V vs. SHE in a system of the metal ion ($M^{n+}$)/the metal (M)), specifically cited are K (−2.925 (V)), Ca (−2.840 (V)), Na (−2.714 (V)), Mg (−2.356 (V)), and Cs (−2.923 (V)). In particular, K, Na, and Cs are preferably used from the viewpoints of an electron injection property and stability.

<Blocking Layer: Hole Blocking Layer, Electron Blocking Layer>

An blocking layer is appropriately provided in addition to the basic constitution layers composed of organic thin layers as described above. Examples are described in such as JP-A Nos. 11-204258 and 11-204359 and p. 273 of "Organic EL Elements and Industrialization Front Thereof (Nov. 30 (1998), published by N. T. S Corp.)" is applicable to a hole blocking (hole block) layer according to the present invention.

A hole blocking layer, in a broad meaning, is provided with a function of electron transport layer, being comprised of a material having a function of transporting an electron but a very small ability of transporting a hole, and can improve the recombination probability of an electron and a hole by blocking a hole while transporting an electron.

Further, a constitution of an electron transport layer described above can be appropriately utilized as a hole blocking layer according to the present invention.

The hole blocking layer of the organic EL element of the present invention is preferably arranged adjacent to the light emitting layer.

It is preferable that the hole blocking layer incorporates a carbazole derivative, or a azacarbazole derivative (here, "a azacarbazole derivative" indicates a compound in which at least one of the carbon atoms constituting the carbazole ring is replaced with a nitrogen atom) listed as a host compound as described above.

Further, in the present intention, in the case in which a plurality of light emitting layers which differ in a plurality of different emitted light colors, it is preferable that the light emitting layer which results in the shortest wavelength of the emitted light maximum wavelength is nearest to the anode in all light emitting layers. However, in such a case, it is preferable to additionally arrange the hole blocking layer between the aforesaid shortest wavelength layer and the light emitting layer secondly near the anode. Further, at least 50% by weight of the compounds incorporated in the hole blocking layer arranged in the aforesaid position preferably exhibits the ionization potential which is greater by at least 0.3 eV than that of the host compounds of the aforesaid shortest wavelength light emitting layer.

The ionization potential is defined as energy which is necessary to release electrons in the HOMO (being the highest occupied molecular orbital) to the vacuum level, and may be determined via, for example, the method described below.

(1) By employing Gaussian98 (Gaussian98, Revision A. 11.4, M. J. Frisch, et al. Gaussian 98 (Gaussian98, Revision A. 11.4, M. J. Frisch, et al, Gaussian, Inc., Pittsburg Pa., 2002), which is a molecular orbital calculation software, produced by Gaussian Co. in the United State of America, and by employing B3LYP/6-31G* as a key word, the value (in terms of corresponding eV unit) was computed, and it is possible to obtain the ionization potential by rouging off the second decimal point. The background in which the resulting calculated values are effective, is that the calculated values obtained by the above method exhibit high relationship with the experimental values.

(2) It is possible to determine the ionization potential via a method in which ionization potential is directly determined employing a photoelectron spectrometry. For example, by employing a low energy electron spectrophotometer "Model AC-1", produced by Riken Keiki Co., or appropriately employ a method known as an ultraviolet light electron spectrometry.

On the other hand, the electron blocking layer, as described herein, has a function of the hole transport layer in a broad sense, and is composed of materials having markedly small capability of electron transport, while having capability of transporting holes and enables to enhance the recombination probability of electrons and holes by inhibiting electrons, while transporting electrons.

Further, it is possible to employ the constitution of the hole transport layer, described below, as an electron blocking layer when needed. The thickness of the hole blocking layer and the electron transport layer according to the present invention is preferably 3-100 nm, but is more preferably 3-30 nm.

<<Hole Transport Layer>>

A hole transport layer contains a material having a function of transporting a hole, and in a broad meaning, a hole injection layer and an electron blocking layer are also included in a hole transport layer. A single layer of or plural layers of a hole transport layer may be provided.

A hole transport material is those having any one of a property to inject or transport a hole or a barrier property to an electron, and may be either an organic substance or an inorganic substance.

For example, listed are a triazole derivative, an oxadiazole derivative, an imidazole derivative, a polyarylalkane derivative, a pyrazolone derivative, a phenylenediamine derivative, an arylamine derivative, an amino substituted chalcone derivative, an oxazole derivatives, a styrylanthracene derivative, a fluorenone derivative, a hydrazone derivative, a stilbene derivative, a silazane derivative, an aniline type copolymer, or conductive polymer oligomer and specifically preferably such as thiophene oligomer.

As a hole transport material, those described above can be utilized, however, it is preferable to utilized a porphyrin compound, an aromatic tertiary amine compound and a styrylamine compound, and specifically preferably an aromatic tertiary amine compound.

Typical examples of an aromatic tertiary amine compound and a styrylamine compound include: N,N,N',N'-tetraphenyl-4,4'-diaminophenyl; N,N'-diphenyl-N,N'-bis(3-methylphenyl)-(1,1'-biphenyl)-4,4'-diamine (TDP); 2,2-bis(4-di-p-tolylaminophenyl)propane; 1,1-bis(4-di-p-tolylaminophenyl)cyclohexane; N,N,N',N'-tetra-p-tolyl 4,4'-diaminobiphenyl; 1,1-bis(4-di-p-tolylaminophenyl)-4-phenylcyclohexane; bis(4-dimethylamino-2-methyl)phenylmethane; bis(4-di-p-tolylaminophenyl)phenylmethane; N,N'-diphenyl-N,N'-di(4-methoxyphenyl)-4,4'-diaminobiphenyl; N,N, N',N'-tetraphenyl-4,4'-diaminophenylether; 4,4'-bis(diphenylamino)quadriphenyl; N,N,N-tri(p-tolyl)amine; 4-(di-p-tolylamino)-4'-[4-(di-p-triamino)styryl]stilbene; 4-N,N-diphenylamino-(2-diphenylvinyl)benzene; 3-methoxy-4'-N,N-diphenylaminostilbene; and N-phenylcarbazole, in addition to those having two condensed aromatic rings in a molecule described in U.S. Pat. No. 5,061,569, such as 4,4'-bis[N-(1-naphthyl)-N-phenylamino]biphenyl (NDP), and 4,4',4"-tris[N-(3-methylphenyl)-N-phenylamino]triphenylamine (MDTDATA), in which three of triphenylamine units are bonded in a star burst form, described in JP-A No. 4-308688.

Polymer materials, in which these materials are introduced in a polymer chain or constitute the main chain of polymer, can be also utilized.

Further, an inorganic compound such as a p type-Si and a p type-SiC can be utilized as a hole injection material and a hole transport material Further, it is possible to employ so-called p type hole transport materials, as described in Japanese Patent Publication Open to Public Inspection (referred to as JP-A) No. 11-251067, and J. Huang et al. reference (Applied Physics Letters 80 (2002), p. 139). In the present invention, since high efficiency light emitting elements are prepared, it is preferable to employ these materials.

This hole transport layer can be prepared by forming a thin layer made of the above-described hole transport material according to a method well known in the art such as a vacuum evaporation method, a spin coating method, a cast method, an inkjet method and a LB method.

The layer thickness of a hole transport layer is not specifically limited, however, it is generally 5 nm-5 μm, and preferably 5 nm-200 nm. This positive transport layer may have a single layer structure comprised of one or not less than two types of the above described materials.

Further, it is possible to employ a hole transport layer of a higher p property which is doped with impurities. As its example, listed are those described in each of JP-A Nos. 4-297076, 2000-196140, 2001-102175, as well as in J. Appl. Phys., 95, 5773 (2004).

In the present invention, it is preferable to employ a hole transport layer of such a high p property, since it is possible to produce an element of lower electric power consumption.

There are given examples of the compound preferably used for formation of the hole transporting layer of the organic EL element of the present invention. However, the present invention is not limited to these.

HT-1 (TPD)
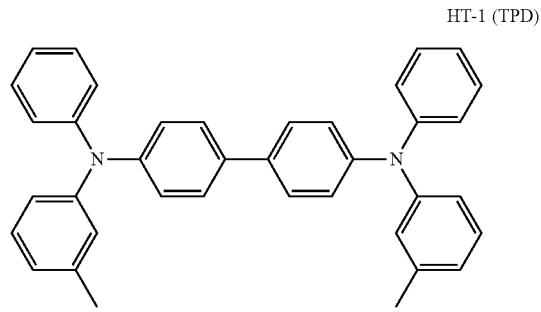
HT-2 (α-NPD)
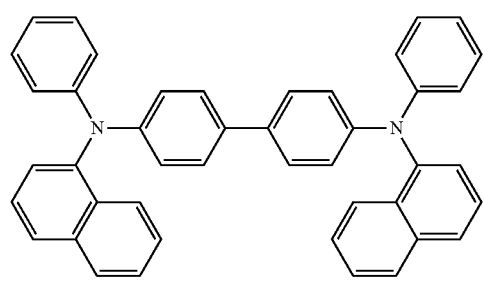
HT-3
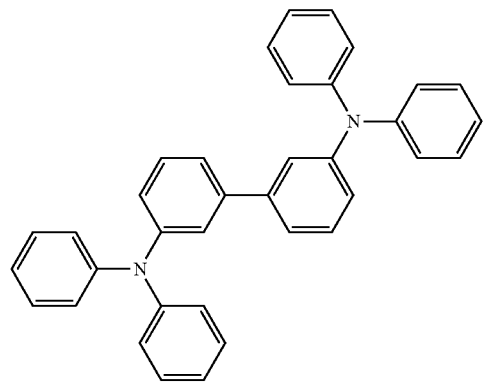
HT-4
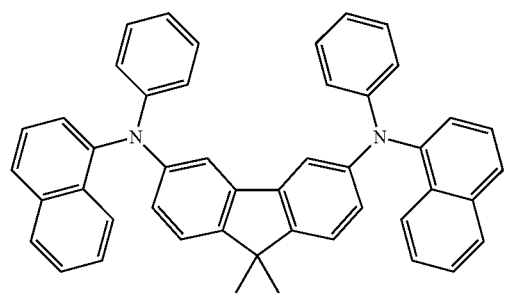
-continued
HT-5
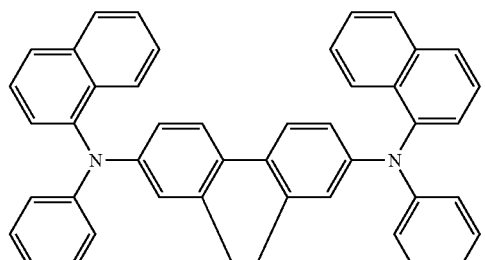
HT-6
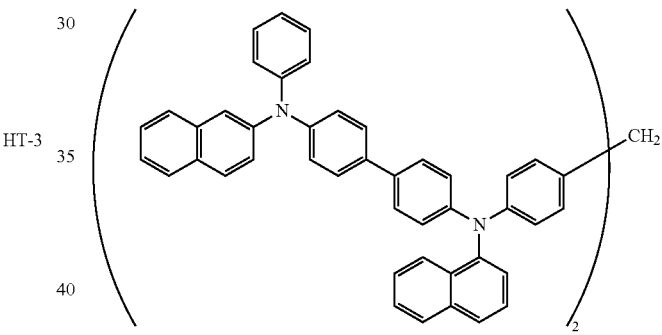
HT-7
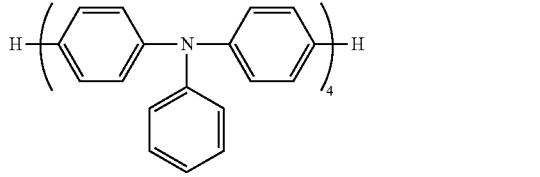
HT-8
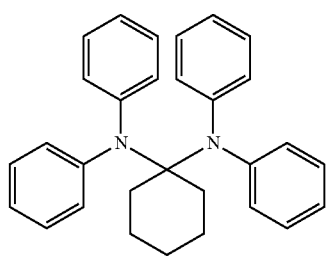

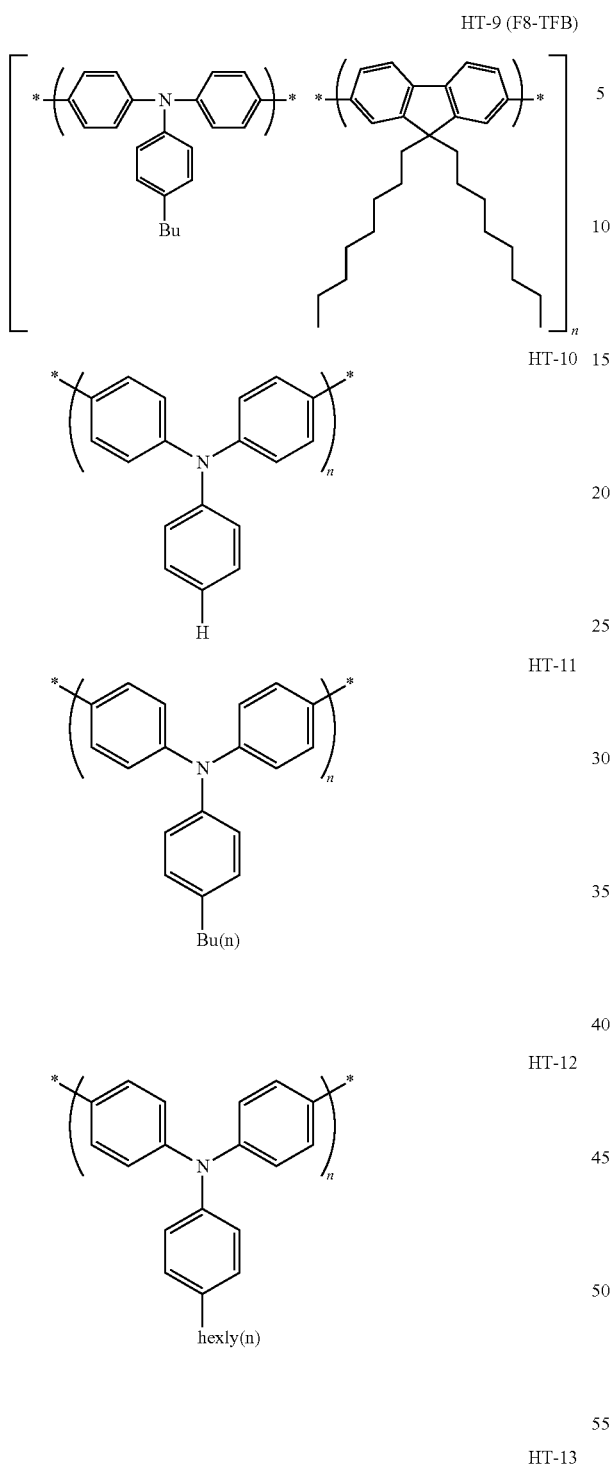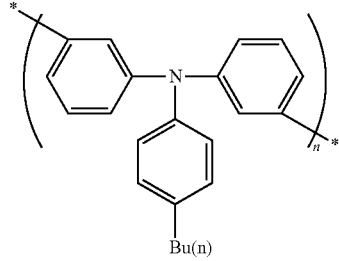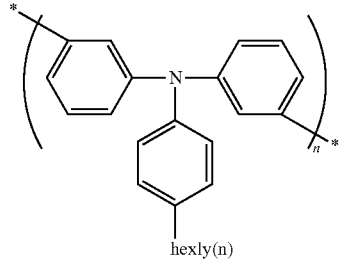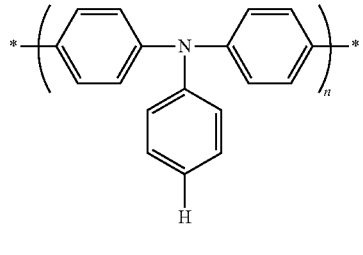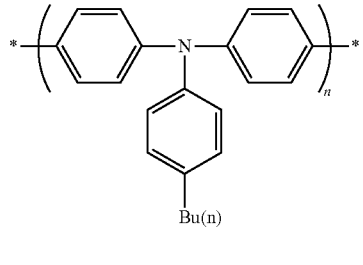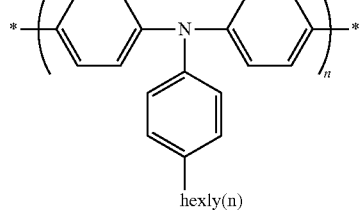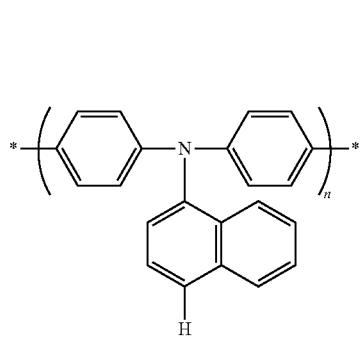

-continued

HT-20
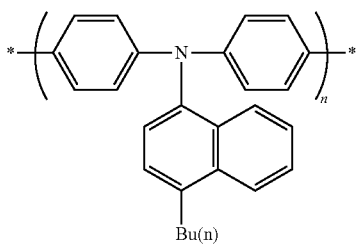
Bu(n)

HT-21
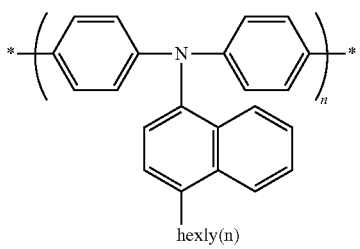
hexly(n)

HT-22
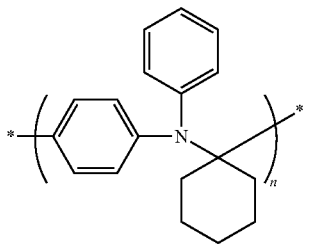

HT-23
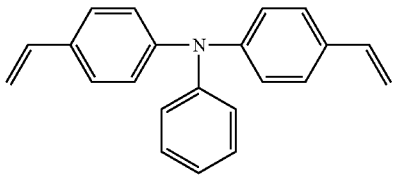

HT-24
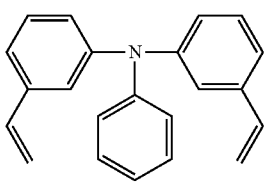

HT-25
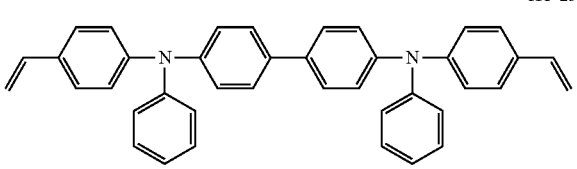

HT-26
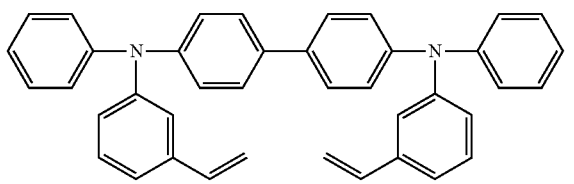

-continued

HT-25
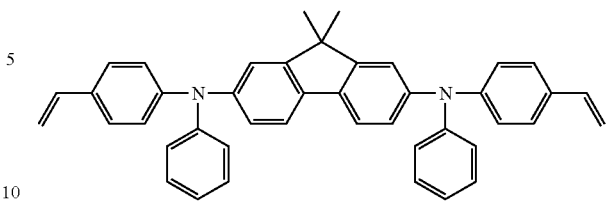

HT-26
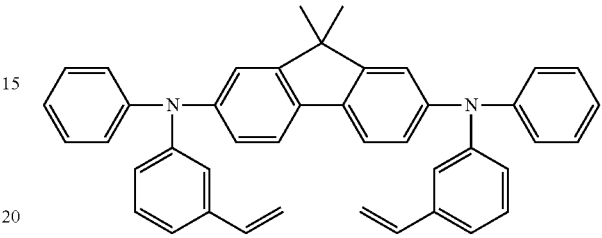

<<Anode>>

As an anode according to an organic EL element of the present invention, those comprising metal, alloy, a conductive compound, which is provided with a large work function (not less than 4 eV), and a mixture thereof as an electrode substance are preferably utilized. Specific examples of such an electrode substance include a conductive transparent material such as metal like Au, CuI, indium tin oxide (ITO), $SnO_2$ and ZnO.

Further, a material such as IDIXO ($In_2O_3$—ZnO), which can prepare an amorphous and transparent electrode, may be also utilized. As for an anode, these electrode substances may be made into a thin layer by a method such as evaporation or spattering and a pattern of a desired form may be formed by means of photolithography, or in the case of requirement of pattern precision is not so severe (not less than 100 □m), a pattern may be formed through a mask of a desired form at the time of evaporation or spattering of the above-described substance.

Alternatively, when coatable materials such as organic electrically conductive compounds are employed, it is possible to employ a wet system filming method such as a printing system or a coating system. When emission is taken out of this anode, the transmittance is preferably set to not less than 10% and the sheet resistance as an anode is preferably not more than a few hundreds □/□.

Further, although the layer thickness depends on a material, it is generally selected in a range of 10 nm-1,000 nm and preferably of 10 nm-200 nm.

<<Substrate>>

A substrate according to an organic EL element of the present invention is not specifically limited with respect to types of such as glass and plastics. They me be transparent or opaque. However, a transparent substrate is preferable when the emitting light is taken from the side of substrate. Substrates preferably utilized includes such as glass, quartz and transparent resin film. A specifically preferable substrate is resin film capable of providing an organic EL element with a flexible property.

Resin film includes such as: polyesters such as polyethylene terephthalate (PET) and polyethylene naphthalate (PEN); polyethylene, polypropyrene; cellulose esters or their derivatives such as cellophane, cellulose diacetate, cellulose triacetate, cellulose acetate butylate, cellulose acetate propionate (CAP), cellulose acetate phthalate (TAC)

and cellulose nitrate; polyvinylidene chloride, polyvinyl alcohol, polyethylene vinyl alcohol, syndiotactic polystyrene, polycarbonate, norbornene resin, polymethylpentene, polyether ketone, polyimide, polyether sulfone (PES), polyphenylene sulfide, polysulfones, polyetherimide, polyether ketone imide, polyamide, fluororesin, Nylon, polymethylmethacrylate, acrylic resin, polyacrylate; and cycloolefine resins such as ARTON (produced by JSR Co. Ltd.) and APEL (produce by Mitsui Chemicals, Inc.)

On the surface of a resin film, it may be formed a film incorporating an inorganic or an organic compound or a hybrid film incorporating both compounds. Barrier films are preferred at a water vapor permeability (25±0.5° C., and relative humidity (90±2)% RH) of at most 0.01 g/(m$^2$·24 h), determined based on JIS K 7129-1992. Further, high barrier films are preferred at an oxygen permeability of at most $1 \times 10^{-3}$ ml/(m$^2$·24 h·MPa), and at a water vapor permeability of at most $10^{-5}$ g/(m$^2$·24 h), determined based on JIS K 7126-1987.

As materials forming a barrier film, employed may be those which retard penetration of moisture and oxygen, which deteriorate the element. For example, it is possible to employ silicon oxide, silicon dioxide, and silicon nitride. Further, in order to improve the brittleness of the aforesaid film, it is more preferable to achieve a laminated layer structure of inorganic layers and organic layers. The laminating order of the inorganic layer and the organic layer is not particularly limited, but it is preferable that both are alternatively laminated a plurality of times.

Barrier film forming methods are not particularly limited, and examples of employable methods include a vacuum deposition method, a sputtering method, a reactive sputtering method, a molecular beam epitaxy method, a cluster ion beam method, an ion plating method, a plasma polymerization method, a plasma CVD method, a laser CVD method a thermal CVD method, and a coating method. Of these, specifically preferred is a method employing an atmospheric pressure plasma polymerization method, described in JP-A No. 2004-68143.

Examples of opaque support substrates include metal plates such aluminum or stainless steel, films, opaque resin substrates, and ceramic substrates.

The external extraction efficiency of light emitted by the organic EL element of the present invention is preferably at least 1% at room temperature, but is more preferably at least 5%.

External quantum yield (%)=(the number of photons emitted by the organic EL element to the exterior/the number of electrons fed to organic EL element)×100

Further, even by simultaneously employing color hue improving filters such as a color filter, simultaneously employed may be color conversion filters which convert emitted light color from the organic EL element to multi-color by employing fluorescent materials. When the color conversion filters are employed, it is preferable that λmax of light emitted by the organic EL element is at least 480 nm.

<<Preparation Method of Organic EL Element>>

As one example of the preparation method of the organic EL element of the present invention, there will be described the preparation method of the organic EL element composed of: anode/hole injection layer/hole transport layer/light emitting layer/hole blocking layer/electron transport layer/cathode buffer layer (electron injection layer)/cathode.

Initially, a thin film composed of desired electrode substances, for example, anode substances is formed on an appropriate base material to reach a thickness of at most 1 μm, but preferably 10 nm-200 nm, whereby an anode is prepared.

Subsequently, on the above, formed are organic compound thin layers including a hole injection layer, a hole transport layer, a light emitting layer, a hole blocking layer, an electron transport layer, and a cathode buffer layer, which contain organic materials.

Examples of a wet process include: a spin coating method, a cast method, a die coating method, a blade coating method, a roll coating method, an inkjet method, a printing method, a spray coating method, a curtain coating method, and a LB method. From the viewpoint of enabling to form a precise thin layer with a high productivity, a die coating method, a roll coating method, an inkjet method and a spray coating method are preferably used. These methods are suitable for applying to a roll to roll production method. It may be possible to use a different film production method for every layer.

As liquid media which are employed to dissolve or disperse organic metal complexes according to the present invention, employed may be, for example, ketones such as methyl ethyl ketone or cyclohexanone, fatty acid esters such as ethyl acetate, halogenated hydrocarbons such as dichlorobenzene, aromatic hydrocarbons such as toluene, xylene, mesitylene, and cyclohexylbenzene, aliphatic hydrocarbons such as cyclohexane, decaline, and dodecane, and organic solvents such as DMF or DMSO.

Further, with regard to dispersion methods, it is possible to achieve dispersion employing dispersion methods such as ultrasonic waves, high shearing force dispersion or media dispersion.

After forming these layers, a thin layer composed of cathode materials is formed on the above layers so that the film thickness reaches at most 1 μm, but is preferably in the range of 50-200 nm, whereby a cathode is arranged, and the desired organic EL element is prepared.

Further, by reversing the preparation order, it is possible to achieve preparation in order of a cathode, a cathode buffer layer, an electron injection layer, an electron transport layer, a light emitting layer, a hole transport layer, a hole injection layer, and an anode.

When direct current voltage is applied to the multicolor display device prepared as above, the anode is employed as "+" polarity, while the cathode is employed as "−" polarity. When 2-40 V is applied, it is possible to observe light emission. Further, alternating current voltage may be applied. The wave form of applied alternating current voltage is not specified.

It is preferable to produce an organic EL element of the present invention with one vacuum operation, from formation of a hole injection layer to formation of a cathode without interruption. However, it may be possible to interrupt the operation and take out the intermediate product in order to apply a different film forming method. In that case, working under a dry inert gas atmosphere is preferable.

<<Sealing>>

As sealing means employed in the present invention, listed may be, for example, a method in which sealing members, electrodes, and a supporting substrate are subjected to adhesion via adhesives.

The sealing members may be arranged to cover the display region of an organic EL element, and may be an engraved plate or a flat plate. Neither transparency nor electrical insulation is limited.

Specifically listed are glass plates, polymer plate-films, metal plates, and films. Specifically, it is possible to list, as glass plates, soda-lime glass, barium-strontium containing glass, lead glass, aluminosilicate glass, borosilicate glass, barium borosilicate glass, and quartz.

Further, listed as polymer plates may be polycarbonate, acryl, polyethylene terephthalate, polyether sulfide, and polysulfone. As a metal plate, listed are those composed of at least one metal selected from the group consisting of stainless steel, iron, copper, aluminum magnesium, nickel, zinc, chromium, titanium, molybdenum, silicon, germanium, and tantalum, or alloys thereof.

In the present invention, since it is possible to convert the element to a thin film, it is possible to preferably employ a metal film.

Further, the oxygen permeability of the polymer film is preferably at most $1\times10^{-3}$ ml/(m$^2$·24 h·MPa), determined by the method based on JIS K 7126-1987, while its water vapor permeability (at 25±0.5° C. and relative humidity (90±2)%) is at most $10^{-5}$ g/(m$^2$·24 h), determined by the method based on JIS K 7129-1992.

Conversion of the sealing member into concave is carried out employing a sand blast process or a chemical etching process.

In practice, as adhesives, listed may be photo-curing and heat-curing types having a reactive vinyl group of acrylic acid based oligomers and methacrylic acid as well as moisture curing types such as 2-cyanoacrylates. Further listed may be thermal and chemical curing types (mixtures of two liquids) such as epoxy based ones. Still further listed may be hot-melt type polyamides, polyesters, and polyolefins. Yet further listed may be cationically curable type ultraviolet radiation curable type epoxy resin adhesives.

In addition, since an organic EL element is occasionally deteriorated via a thermal process, those are preferred which enable adhesion and curing between room temperature and 80° C. Further, desiccating agents may be dispersed into the aforesaid adhesives. Adhesives may be applied onto sealing portions via a commercial dispenser or printed on the same in the same manner as screen printing.

Further, it is appropriate that on the outside of the aforesaid electrode which interposes the organic layer and faces the support substrate, the aforesaid electrode and organic layer are covered, and in the form of contact with the support substrate, inorganic and organic material layers are formed as a sealing film. In this case, as materials forming the aforesaid film may be those which exhibit functions to retard penetration of those such as moisture or oxygen which results in deterioration. For example, it is possible to employ silicon oxide, silicon dioxide, and silicon nitride.

Still further, in order to improve brittleness of the aforesaid film, it is preferable that a laminated layer structure is formed, which is composed of these inorganic layers and layers composed of organic materials. Methods to form these films are not particularly limited. It is possible to employ, for example, a vacuum deposition method, a sputtering method, a reactive sputtering method, a molecular beam epitaxy method, a cluster ion beam method, an ion plating method, a plasma polymerization method, an atmospheric pressure plasma polymerization method, a plasma CVD method, a thermal CVD method, and a coating method.

In a gas phase and a liquid phase, it is preferable to inject inert gases such as nitrogen or argon, and inactive liquids such as fluorinated hydrocarbon or silicone oil into the space between the sealing member and the surface region of the organic EL element. Further, it is possible to form vacuum. Still further, it is possible to enclose hygroscopic compounds in the interior.

Examples of hygroscopic compounds include metal oxides (for example, sodium oxide, potassium oxide, calcium oxide, barium oxide, magnesium oxide, and aluminum oxide); sulfates (for example, sodium sulfate, calcium sulfate, magnesium sulfate, and cobalt sulfate); metal halides (for example, calcium chloride, magnesium chloride, cesium fluoride, tantalum fluoride, cerium bromide, magnesium bromide, barium iodide, and magnesium iodide); perchlorates (for example, barium perchlorate and magnesium perchlorate). In sulfates, metal halides, and perchlorates, suitably employed are anhydrides.

<<Protective Film and Protective Plate>>

The aforesaid sealing film on the side which nips the organic layer and faces the support substrate or on the outside of the aforesaid sealing film, a protective or a protective plate may be arranged to enhance the mechanical strength of the element. Specifically, when sealing is achieved via the aforesaid sealing film, the resulting mechanical strength is not always high enough, whereby it is preferable to arrange the protective film or the protective plate described above. Usable materials for these include glass plates, polymer plate-films, and metal plate-films which are similar to those employed for the aforesaid sealing. However, in terms of light weight and a decrease in thickness, it is preferable to employ polymer films.

<<Light Extraction>>

It is generally known that an organic EL element emits light in the interior of the layer exhibiting the refractive index (being about 1.7-about 2.1) which is greater than that of air, whereby only about 15-about 20% of light generated in the light emitting layer is extracted.

This is due to the fact that light incident to an interface (being an interface of a transparent substrate to air) at an angle of θ which is at least critical angle is not extracted to the exterior of the element due to the resulting total reflection, or light is totally reflected between the transparent electrode or the light emitting layer and the transparent substrate, and light is guided via the transparent electrode or the light emitting layer, whereby light escapes in the direction of the element side surface.

Means to enhance the efficiency of the aforesaid light extraction include, for example, a method in which roughness is formed on the surface of a transparent substrate, whereby total reflection is minimized at the interface of the transparent substrate to air (U.S. Pat. No. 4,774,435), a method in which efficiency is enhanced in such a manner that a substrate results in light collection (JP-A No. 63-314795), a method in which a reflection surface is formed on the side of the element (JP-A No. 1-220394), a method in which a flat layer of a middle refractive index is introduced between the substrate and the light emitting body and an antireflection film is formed (JP-A No. 62-172691), a method in which a flat layer of a refractive index which is equal to or less than the substrate is introduced between the substrate and the fight emitting body (JP-A No. 2001-202827), and a method in which a diffraction grating is formed between the substrate and any of the layers such as the transparent electrode layer or the light emitting layer (including between the substrate and the outside) (JP-A No. 11-283751).

In the present invention, it is possible to employ these methods while combined with the organic EL element of the present invention. Of these, it is possible to appropriately employ the method in which a flat layer of a refractive index which is equal to or less than the substrate is introduced between the substrate and the light emitting body and the method in which a diffraction grating is formed between the substrate and any of the layers such as the transparent electrode layer or the light emitting layer (including between the substrate and the outside).

By combining these means, the present invention enables the production of elements which exhibit higher luminance or excel in durability.

When a low refractive index medium of a thickness, which is greater than the wavelength of light, is formed between the transparent electrode and the transparent substrate, the extraction efficiency of light emitted from the transparent electrode to the exterior increases as the refractive index of the medium decreases.

As materials of the low refractive index layer, listed are, for example, aerogel, porous silica, magnesium fluoride, and fluorine based polymers. Since the refractive index of the transparent substrate is commonly about 1.5-about 1.7, the refractive index of the low refractive index layer is preferably at most approximately 1.5, but is more preferably at most 1.35.

Further, thickness of the low refractive index medium is preferably at least two times the wavelength in the medium. The reason is that when the thickness of the low refractive index medium reaches nearly the wavelength of light so that electromagnetic waves oozed via evernescent enter into the substrate, effects of the low refractive index layer are lowered.

The method in which the interface which results in total reflection or a diffraction grating is introduced in any of the media is characterized in that light extraction efficiency is significantly enhanced.

The above method works as follows. By utilizing properties of the diffraction grating capable of changing the light direction to the specific direction different from diffraction via so-called Bragg diffraction such as primary diffraction or secondary diffraction of the diffraction grating, of light emitted from the light emitting layer, light, which is not emitted to the exterior due to total reflection between layers, is diffracted via introduction of a diffraction grating between any layers or in a medium (in the transparent substrate and the transparent electrode) so that light is extracted to the exterior.

It is preferable that the introduced diffraction grating exhibits a two-dimensional periodic refractive index. The reason is as follows. Since light emitted in the light emitting layer is randomly generated to all directions, in a common one-dimensional diffraction grating exhibiting aperiodic refractive index distribution only in a certain direction, light which travels to the specific direction is only diffracted, whereby light extraction efficiency is not sufficiently enhanced.

However, by changing the refractive index distribution to a two-dimensional one, light, which travels to all directions, is diffracted, whereby the light extraction efficiency is enhanced.

As noted above, a position to introduce a diffraction grating may be between any layers or in a medium (in a transparent substrate or a transparent electrode). However, a position near the organic light emitting layer, where light is generated, is desirous.

In this case, the cycle of the diffraction grating is preferably about ½-about 3 times the wavelength of light in the medium.

The preferable arrangement of the diffraction grating is such that the arrangement is two-dimensionally repeated in the form of a square lattice, a triangular lattice, or a honeycomb lattice.

<<Light Collection Sheet>>

Via a process to arrange a structure such as a micro-lens array shape on the light extraction side of the organic EL element of the present invention or via combination with a so-called light collection sheet, light is collected in the specific direction such as the front direction with respect to the light emitting element surface, whereby it is possible to enhance luminance in the specific direction.

In an example of the micro-lens array, square pyramids to realize a side length of 30 μm and an apex angle of 90 degrees are two-dimensionally arranged on the light extraction side of the substrate. The side length is preferably 10 μm-100 μm. When it is less than the lower limit, coloration results due to generation of diffraction effects, while when it exceeds the upper limit, the thickness increases undesirably.

It is possible to employ, as a light collection sheet, for example, one which is put into practical use in the LED backlight of liquid crystal display devices. It is possible to employ, as such a sheet, for example, the luminance enhancing film (BEF), produced by Sumitomo 3M Limited.

As shapes of a prism sheet employed may be, for example, Δ shaped stripes of an apex angle of 90 degrees and a pitch of 50 μm formed on a base material, a shape in which the apex angle is rounded, a shape in which the pitch is randomly changed, and other shapes.

Further, in order to control the light radiation angle from the light emitting element, simultaneously employed may be a light diffusion plate-film. For example, it is possible to employ the diffusion film (LIGHT-UP), produced by Kimoto Co., Ltd.

<<Application>>

It is possible to employ the organic EL element of the present invention as display devices, displays, and various types of light emitting sources. Examples of light emitting sources include, but are not limited to lighting apparatuses (home lighting and car lighting), clocks, backlights for liquid crystals, sign advertisements, signals, light sources of light memory media, light sources of electrophotographic copiers, light sources of light communication processors, and light sources of light sensors.

It is effectively employed especially as backlights of liquid crystal display devices and lighting sources.

If needed, the organic EL element of the present invention may undergo patterning via a metal mask or an ink-jet printing method during film formation. When the patterning is carried out, only an electrode may undergo patterning, an electrode and a light emitting layer may undergo patterning, or all element layers may undergo patterning. During preparation of the element, it is possible to employ conventional methods.

Figure 4:
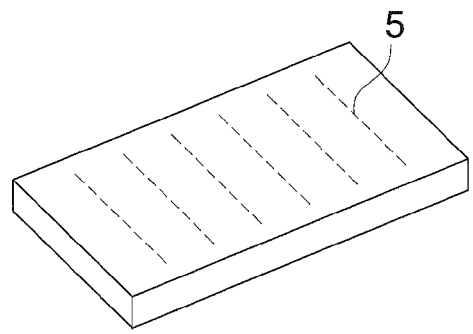
FIG. 4 is a schematic drawing of a full color display device according to a passive matrix mode.
Figure 4:
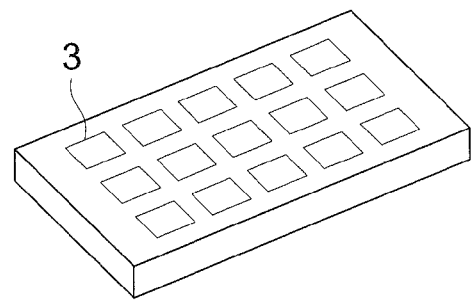
Figure 4:
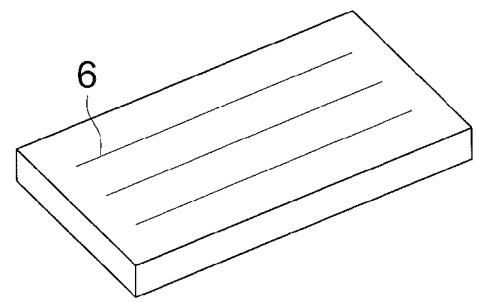

Color of light emitted by the organic EL element of the present invention and compounds according to the present invention is specified as follows. In FIG. 4.16 on page 108 of "Shinpen Shikisai Kagaku Handbook (New Edition Color Science Handbook)" (edited by The Color Science Association of Japan, Tokyo Daigaku Shuppan Kai, 1985), values determined via a spectroradiometric luminance meter CS-1000 (produced by Konica Minolta Sensing Inc.) are applied to the CIE chromaticity coordinate, whereby the color is specified.

Further, when the organic EL element of the present invention is a white element, "white", as described herein, means that when 2-degree viewing angle front luminance is determined via the aforesaid method, chromaticity in the CIE 1931 Color Specification System is within the region of X=0.33±0.07 and Y=0.33±0.07.

<<Display Device>>

A display device of the present invention will now be explained. The display device of the present invention includes the above-described organic EL element.

A display device of the present invention may be either monochromatic or multi-colored. Here explained will be a multicolor display device. In the case of a multicolor display device, a shadow mask is provided only at the time of emission layer formation, and layers can be formed all over the surface by such as an evaporation method, a cast method, a spin coat method, an inkjet method and a printing method.

When patterning is performed only for producing a light emitting layer, the method is not specifically limited; however, preferable are an evaporation method, an inkjet method, a spin coating method and a printing method.

The constitution of the organic EL element used for a display device can be selected from the embodiments of the organic EL element as described above, in accordance with the requirement.

The production method of the organic EL element was described above for one of the embodiments of the organic EL element of the present invention.

When a direct current voltage is applied on the multicolor display device thus prepared emission can be observed by application of a voltage of approximately 2-40 V setting an anode to + polarity and a cathode to − polarity. Further, no current flows and no emission generate at all even when a voltage is applied with a reversed polarity. Further, in the case of alternate current voltage being applied, emission generates only in a state of an anode being + and a cathode being −. Herein, the wave shape of alternate current may be arbitrary.

A multicolor display device can be utilized as a display device, a display and various types of emission light sources. In a display device and a display, full-colored display is possible by employing three types of organic EL elements providing blue, red and green emissions.

A display device and a display include a TV, a personal computer, a mobile instrument, an AV instrument, a character broadcast display and an information display in a car. Particularly, the display device and the display may be also utilized as a display to playback still images and moving images, and may adopt either a simple matrix (a passive matrix) mode or an active matrix mode when being utilized as a display device for moving image playback.

An illumination light source includes a home use illumination, a car room illumination, a backlight of a watch or a liquid crystal, a panel advertisement, a signal, a light source of an optical memory medium, a light source for an electrophotographic copier, a light source for an optical telecommunication processor and a light source for a photosensor, however, the present invention is not limited thereto.

In the following, one example of a display device provided with an organic EL element of the present invention will be explained with reference to figures.

FIG. 1 is a schematic drawing to show an example of a display device constituted of an organic EL element. It is a schematic drawing of a display, which displays image information by emission of an organic EL element, such as a mobile phone.

Display 1 is constituted of display section A having plural number of pixels and control section B which performs image scanning of display section A based on image information.

Control section B, which is electrically connected to display section A, sends a scanning signal and an image data signal to plural number of pixels based on image information from the outside and pixels of each scanning line successively emit depending on the image data signal by a scanning signal to perform image scanning, whereby image information is displayed on display section A.

Figure 2:
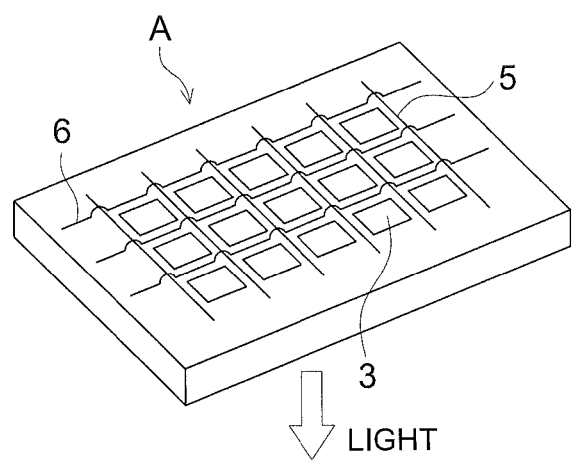
FIG. 2 is a schematic drawing of display section A.

FIG. 2 is a schematic drawing of display section A.

Display section A is provided with such as a wiring part, which contains plural scanning lines 5 and data lines 6, and plural pixels 3 on a substrate. Primary part materials of display section A will be explained in the following.

In the drawing, shown is the case that light emitted by pixel 3 is taken out along the white allow (downward).

Scanning lines 5 and plural data lines 6 in a wiring part each are comprised of a conductive material, and scanning lines 5 and data lines 6 are perpendicular in a grid form and are connected to pixels 3 at the right-angled crossing points (details are not shown in the drawing).

Pixel 3 receives an image data from data line 6 when a scanning signal is applied from scanning line 5 and emits according to the received image data.

Full-color display device is possible by appropriately arranging pixels having an emission color in a red region, pixels in a green region and pixels in a blue region, side by side on the same substrate.

Next, an emission process of a pixel will be explained.

Figure 3:
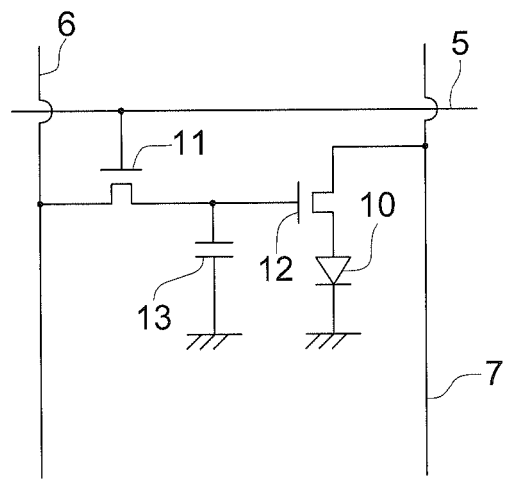
FIG. 3 is an equivalent circuit diagram of an image pixel.

FIG. 3 is a schematic drawing of a pixel.

A pixel is equipped with such as organic EL element 10, switching transistor 11, operating transistor 12 and capacitor 13. Red, green and blue emitting organic EL elements are utilized as organic EL element 10 for plural pixels, and full-color display device is possible by arranging these side by side on the same substrate.

In FIG. 3, an image data signal is applied on the drain of switching transistor 11 via data line 6 from control section B. Then, when a scanning signal is applied on the gate of switching transistor 11 via scanning line 5 from control section B, operation of switching transistor is on to transmit the image data signal applied on the drain to the gates of capacitor 13 and operating transistor 12.

Operating transistor 12 is on, simultaneously with capacitor 13 being charged depending on the potential of an image data signal, by transmission of an image data signal. In operating transistor 12, the drain is connected to electric source line 7 and the source is connected to the electrode of organic EL element 10, and an electric current is supplied from electric source line 7 to organic EL element 10 depending on the potential of an image data applied on the gate.

When a scanning signal is transferred to next scanning line 5 by successive scanning of control section B, operation of switching transistor 11 is off. However, since condenser 13 keeps the charged potential of an image data signal even when operation of switching transistor 11 is off, operation of operating transistor 12 is kept on to continue emission of organic EL element 10 until the next scanning signal is applied. When the next scanning signal is applied by successive scanning, operating transistor 12 operates depending on the potential of an image data signal synchronized to the scanning signal and organic EL element 10 emits.

That is, emission of each organic EL element 10 of plural pixels 3 is performed by providing switching transistor 11 and operating transistor 12 against each organic EL element 10 of plural pixels 3. Such an emission method is called as an active matrix mode.

Herein, emission of organic EL element 10 may be either emission of plural gradations based on a multiple-valued image data signal having plural number of gradation potentials or on and off of a predetermined emission quantity based on a binary image data signal. Further, potential hold of capacitor 13 may be either continuously maintained until the next scanning signal application or discharged immediately before the next scanning signal application.

In the present invention, emission operation is not necessarily limited to the above-described active matrix mode but may be a passive matrix mode in which organic EL element is emitted based on a data signal only when a scanning signal is scanned.

FIG. 4 is a schematic drawing of a display device based on a passive matrix mode. In FIG. 4, plural number of scanning lines 5 and plural number of image data lines 6 are arranged grid-wise, opposing to each other and sandwiching pixels 3.

When a scanning signal of scanning line 5 is applied by successive scanning, pixel 3 connected to scanning line 5 applied with said signal emits depending on an image data signal.

Since pixel 3 is provided with no active element in a passive matrix mode, decrease of manufacturing cost is possible.

<<Lighting Device>>

A lighting device of the present invention will now be explained. The lighting device of the present invention includes the above-described organic EL element.

An organic EL element of the present invention can be utilized as an organic EL element provided with a resonator structure, and a utilization purpose of such an organic EL element provided with a resonator structure includes such as a light source for an optical memory medium, a light source for an electrophotographic copier, a light source for a optical telecommunication processor and a light source for a photosensor, however, is not limited thereto. Further, the organic EL element may be utilized for the above-described applications by being made to perform laser emission.

Further, an organic EL element of the present invention may be utilized as one type of a lamp like an illumination and an exposure light, and may be also utilized as a display device of a projector of an image projecting type and a display device (a display) of a type to directly view still images and moving images.

An operating mode in the case of being utilized as a display device for playback of moving images may be either a simple matrix (a passive matrix) mode or an active matrix mode. In addition, a full-color display device can be prepared by utilizing at least two types of organic EL elements of the present invention which emit different emitting colors.

An organic EL element material of the present invention can be also applied to an organic EL element to generate emission of practically white color as a lighting device. Plural emission colors are simultaneously emitted by plural number of emission materials to obtain white light by mixing colors. A combination of plural emission colors may be either the one, in which three emission maximum wavelengths of three primary colors of blue, green and red are contained, or the other, in which two emission maximum wavelengths, utilizing a relationship of complimentary colors such as blue and yellow, or blue and orange, are contained.

Further, a combination of emission materials to obtain plural number of emission colors may be either a combination comprising plural number of materials which emit phosphoresce or fluorescence, or a combination of a material which emits phosphoresce or fluorescence and a dye material which emits by light from an emission material as exiting light, however, in a white organic electroluminescence element according to the present invention, it is enough only to mix plural emission dopants in combination.

A mask is provided only at the time of forming such as an emission layer, a hole transport layer or an electron transport layer, to only simply arrange the plural emission dopants such as by separately painting through the mask, while other layers are commonly utilized to require no patterning such as a mask. Therefore, such as an electrode can be formed all over the plane by such as an evaporation method, a cast method, a spin coat method, an inkjet method and a printing method, resulting in improvement of productivity.

According to this method, different from a white organic EL device in which plural colors of emission elements are arranged parallel in an alley form, an element itself is white emitting.

An emission material utilized in an emission layer is not specifically limited, and in the case of a backlight of a liquid crystal display element, any combination by arbitrary selection among platinum complexes according to the present invention or emission materials well known in the art can be utilized so as to be fitted to the wavelength range corresponding to CF (color filter) characteristics, whereby white emission can be obtained.

<<One Embodiment of Lighting Device of the Present Invention>>

The non-light emitting surface of the organic EL element of the present invention was covered with a glass case, and a 300 μm thick glass substrate was employed as a sealing substrate. An epoxy based light curable type adhesive (LUXTRACK LC0629B produced by Toagosei Co., Ltd.) was employed in the periphery as a sealing material. The resulting one was superimposed on the aforesaid cathode to be brought into close contact with the aforesaid transparent support substrate, and curing and sealing were carried out via exposure of UV radiation onto the glass substrate side, whereby the lighting device shown in FIGS. 5 and 6 was formed.

Figure 5:
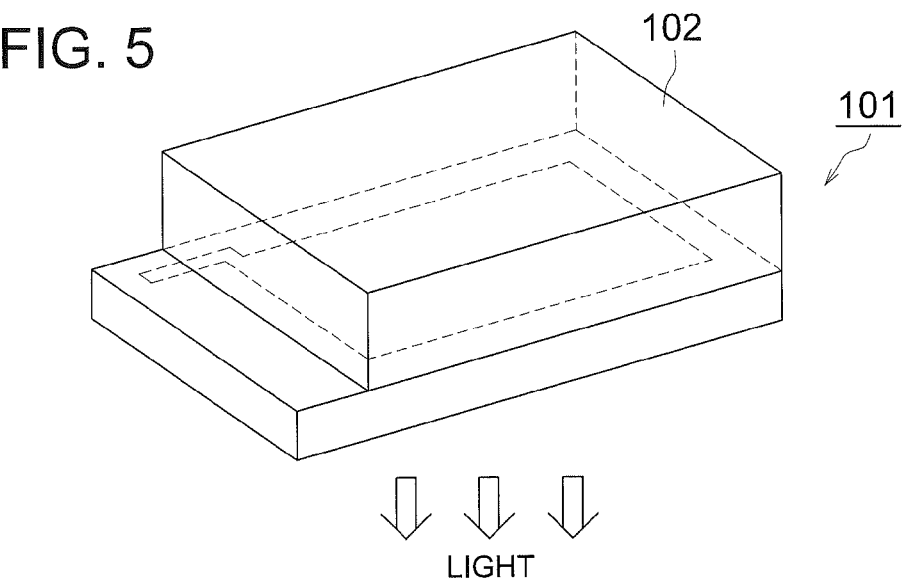
FIG. 5 is a schematic drawing of a lighting device.

FIG. 5 is a schematic view of a lighting device and Organic EL element 101 is covered with glass cover 102 (incidentally, sealing by the glass cover was carried out in a globe box under nitrogen ambience (under an ambience of high purity nitrogen gas at a purity of at least 99.999%) so that Organic EL Element 101 was not brought into contact with atmosphere.

Figure 6:
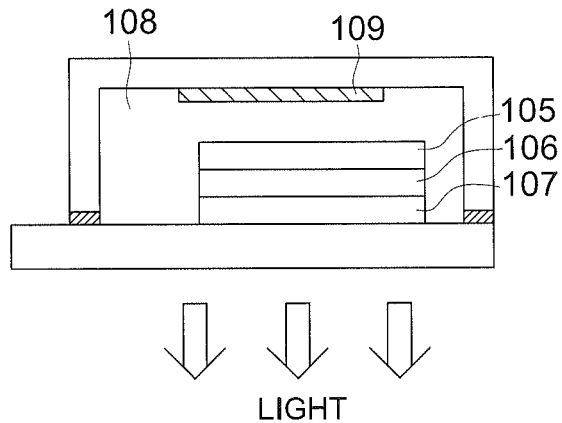
FIG. 6 is a cross-sectional drawing of a lighting device.
Figure 7A:
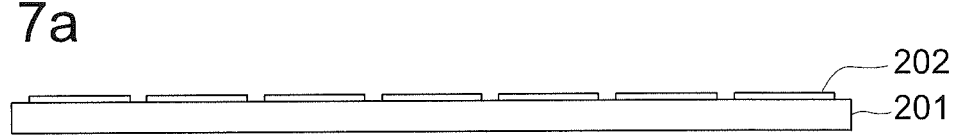
FIGS. 7a to 7e are a schematic structural drawing of a full color organic EL display device.
Figure 7B:
Figure 7C:
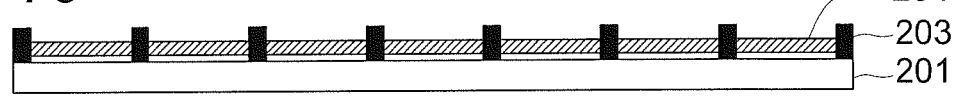
Figure 7D:
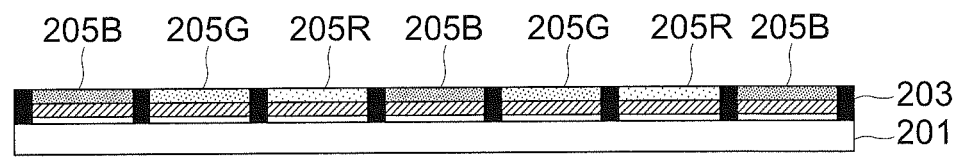
Figure 7E:
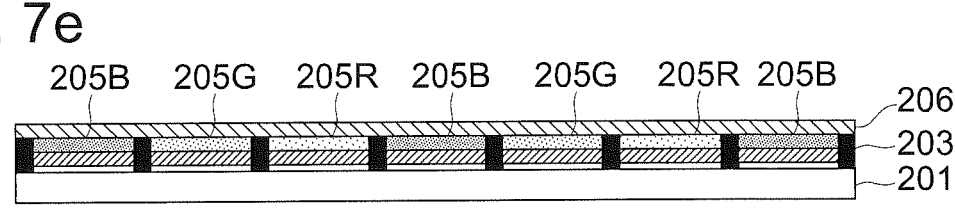

FIG. 6 is a cross-sectional view of a lighting device, and in FIG. 6, 105 represents a cathode, 106 represents an organic EL layer, and 107 represents a glass substrate fitted with a transparent electrode.

Further, the interior of glass cover 102 is filled with nitrogen gas 108 and water catching agent 109 is provided.

EXAMPLES

The present invention will now be described with reference to examples, however the present invention is not limited thereto.

The chemical structures of the compounds used in Examples are shown in the followings.

Electron transport compound 1
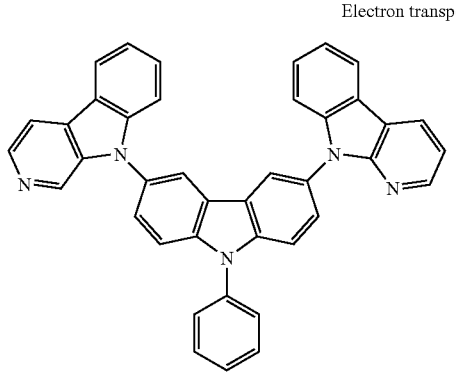
Electron transport compound 2
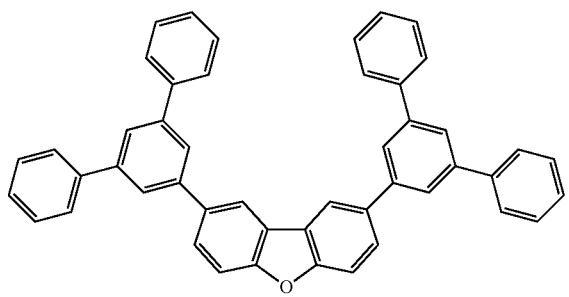
Electron transport compound 3
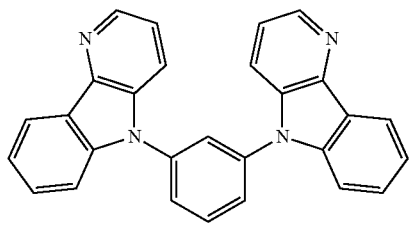
Electron transport compound 4
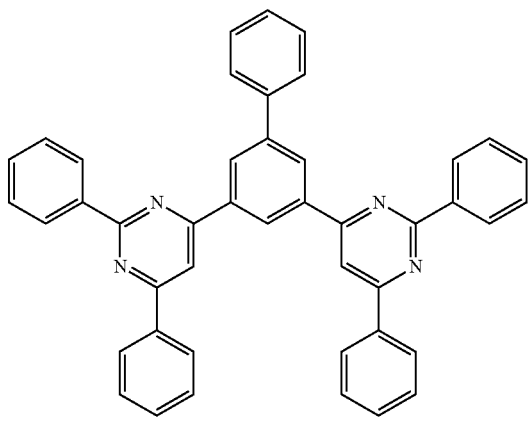
Electron transport compound 5
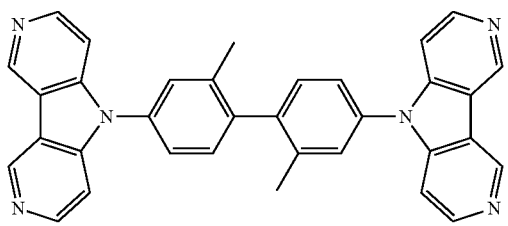
Electron transport compound 6
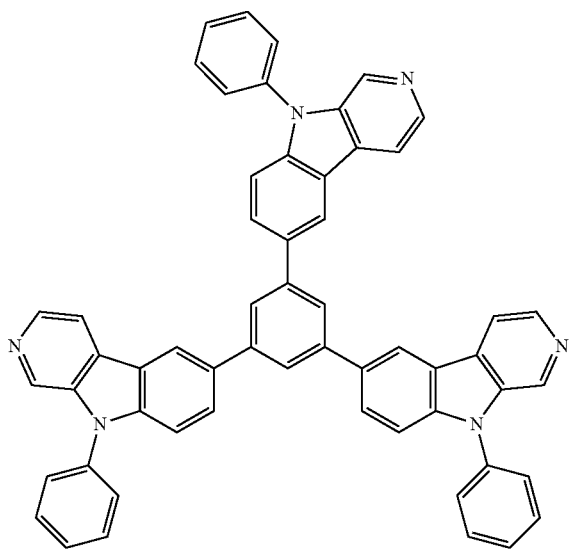

Electron transport compound 7
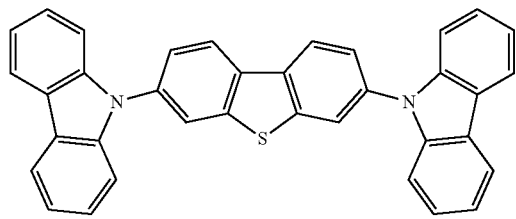
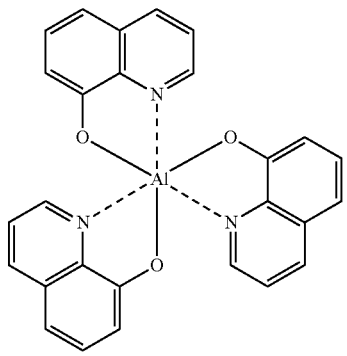
Alq₃
Hole transport compount 1
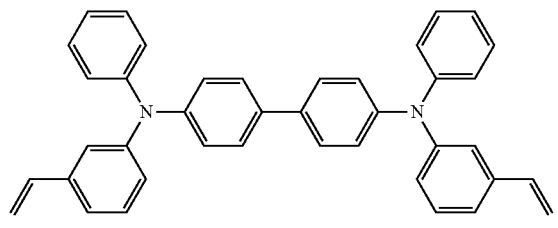
Hole transport compount 2
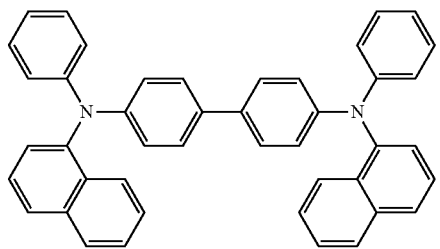
Hole transport compount 3
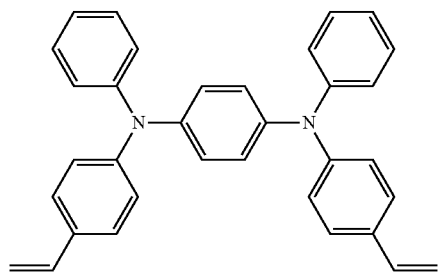
Hole transport compount 4
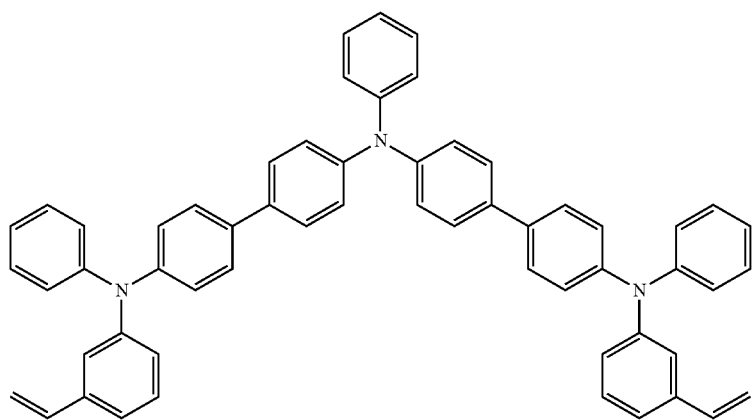

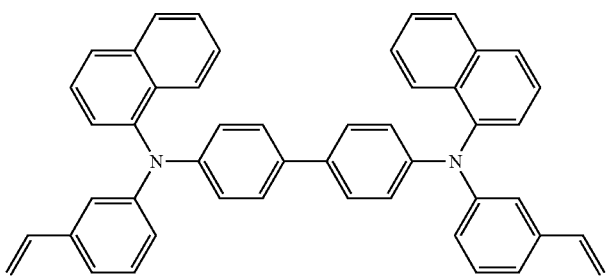

Hole transport compount 5

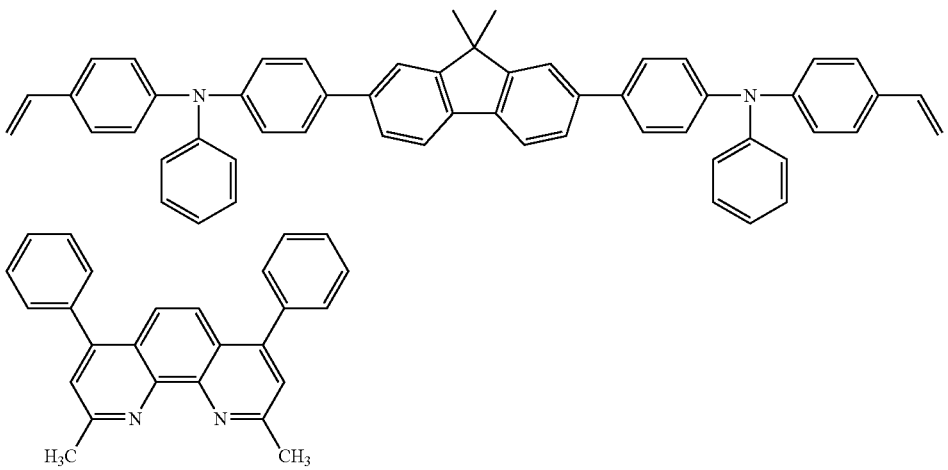

Hole transport compount 6

BCP

Example 1

Preparation of Organic EL Element 1-1

An anode was prepared by making patterning to a glass substrate of 100 mm×100 mm×1.1 mm (NA45 produced by NH Techno Glass Corp.) on which a 100 nm film of ITO (indium tin oxide) was formed. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

On the transparent support substrate thus prepared was applied a 70% solution of poly(3,4-ethylenedioxythiphene)-polystyrene sulfonate (PEDOT/PSS, Baytron P AI4083 made by Bayer AG.) diluted with water by using a spin coating method at 3,000 rpm for 30 seconds to form a film and then it was dried at 200° C. for one hour. A hole transport layer having a thickness of 20 nm was prepared.

The aforesaid substrate was transferred under an atmosphere of nitrogen, and a solution containing 50 mg of Hole transport compound 1 dissolved in 10 ml of toluene was applied on the aforesaid hole transport layer by using a spin coating method at 1,500 rpm for 30 seconds to form a film. The film was irradiated with UV rays for 180 seconds so as to achieve photopolymerization and cross-linking. A $2^{nd}$ hole transport layer having a thickness of 20 nm was thus prepared.

One the $2^{nd}$ hole transport layer was applied a solution containing 100 mg of Host-24 and 10 mg of D-1 dissolved in 10 ml of toluene by using a spin coating method at 600 rpm for 30 seconds to form a film. The film was subjected to a vacuum drying at 60° C. for one hour to obtain a light emitting layer having a thickness of 70 nm.

One the light emitting layer was applied a solution containing 50 mg of Electron transport compound 1 dissolved in 10 ml of hexafluoroisopropanol (HFIP) by using a spin coating method at 1,000 rpm for 30 seconds to form a film. The film was subjected to a vacuum drying at 60° C. for one hour to obtain an electron transport layer having a thickness of 30 nm.

Subsequently, the substrate was fixed to the substrate holder of the vacuum deposition apparatus, and the pressure of the vacuum tank was reduced to $4\times10^{-4}$ Pa. Then, 0.4 nm thick sodium fluoride was deposited to form a cathode buffer layer, then 110 nm thick aluminum was deposited to form a cathode, whereby Organic EL element 1-1 was prepared.

<<Preparation of Organic EL Elements 1-2 to 1-4>>

Organic EL elements 1-2 to 1-4 were prepared in the same manner as preparation of Organic EL element 1-1, except that Electron transport compound 1 was replaced with the compounds as are listed below.

<<Evaluation of Organic EL Elements 1-1 to 1-4>>

In order to evaluate the obtained organic EL elements 1-1 to 1-4, the following processes were done to them. The non-light emitting surface of each of the organic EL elements was covered with a glass cover. As a sealing material, an epoxy based light curable type adhesive (LUXTRACK LC0629B produced by Toagosei Co., Ltd.) was applied to the periphery of the glass cover where the glass cover and the grass substrate prepared thereon Organic EL element were contacted. The resulting one was superimposed on the aforesaid cathode side to be brought into close contact with the aforesaid transparent support substrate, and curing and sealing were carried out via exposure of UV radiation onto the glass substrate side, whereby the lighting device shown in FIGS. 5 and 6 was formed. The organic EL elements were evaluated using the lighting devices. The aging stability of the Organic EL elements was evaluated based on the following evaluations method.

(Aging Stability)

Each Organic EL element was kept at aging condition of 85° C. for 24 hours. Each electric power of Organic EL elements before aging and after aging driven at a constant current of 2.5 mA/cm² was measured. Electric power ratios of before aging and after aging were measured according to the following formula. This value was used for evaluating aging stability.

Aging stability (%)=(Electric power after kept at aging condition(2.5 mA/cm²)/Electric power before kept at aging condition(2.5 mA/cm²))× 100

The obtained results are shown below.

| Organic EL element | Electron transport material | Aging stability (%) | Remarks |
| --- | --- | --- | --- |
| 1-1 | Electron transport compound 1 | 147 | Comparative example |
| 1-2 | 47 | 123 | Present invention |
| 1-3 | 45 | 119 | Present invention |
| 1-4 | 1 | 114 | Present invention |

From the results described above, it is clear that increase of voltage after aging was suppressed for Organic EL elements of the present invention, and Organic EL elements of the present invention were excellent in aging stability (storage property) compared with a comparative organic EL element.

Example 2

Preparation of Organic EL Element 2-1

An anode was prepared by making patterning to a glass substrate of 100 mm×100 mm×1.1 mm (NA45 produced by NH Techno Glass Corp.) on which a 100 nm film of TTO (indium tin oxide) was formed. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

The resulting transparent support substrate was fixed to the substrate holder of a commercial vacuum deposition apparatus. Separately, 200 mg of Hole transport compound 2 (NPD) was placed in a molybdenum resistance heating boat, 200 mg of Host-34 as a host compound was placed in another molybdenum resistance heating boat, D-25 was placed in further another molybdenum resistance heating boat, Electron transport compound 2 was placed in yet another molybdenum resistance heating boat, and the resulting boats were fitted in the vacuum deposition apparatus.

Subsequently, after reducing the pressure of the vacuum tank to 4×10⁻⁴ Pa, the aforesaid heating boat, in which Hole transport compound 2 was placed, was heated via application of electric current and deposition was carried out onto the transparent support substrate at a deposition rate of 0.1 nm/second, whereby a hole transport layer was arranged. Further, the aforesaid heating boats each respectively containing Host-34 and D-25 were heated via application of electric current and co-deposition was carried out onto the aforesaid hole transport layer at a respective deposition rate of 0.2 nm/second and 0.012 nm/second, whereby a light emitting layer was arranged.

Here, the temperature of the substrate during the deposition was room temperature. Further, the aforesaid heating boat containing Electron transport compound 2 was heated via application of electric current and deposition was carried out onto the aforesaid light emitting layer at a deposition rate of 0.1 nm/second, whereby an electron transport layer was arranged. Here, the temperature of the substrate during the deposition was room temperature.

Subsequently, 0.5 nm thick potassium fluoride and 110 nm thick aluminium were vapor deposited to form a cathode, whereby Organic EL element 2-1 was prepared.

<<Preparation of Organic EL Elements 2-2 to 2-4>>

Organic EL elements 2-2 to 2-4 were prepared in the same manner as preparation of Organic EL element 2-1, except that Electron transport compound 2 was replaced with the compounds as are listed below.

<<Evaluation of Organic EL Elements 2-1 to 2-4>>

In order to evaluate the obtained organic EL elements 2-1 to 2-4, the same sealing processes was done as done to Organic EL elements 1-1 to 1-4 in Example 1, whereby the lighting device shown in FIGS. 5 and 6 was formed. The organic EL elements were evaluated using the lighting devices.

The following evaluation was made for the obtained Organic EL elements.

<Aging Stability>

Each Organic EL element was kept at aging condition of 60° C. and 70% RH for one month. In the same manner as in Example 1, each electric power of Organic EL elements before aging and after aging driven at a constant current of 2.5 mA/cm² was measured. Electric power ratios of before aging and after aging were measured according to the following formula. This value was used for evaluating aging stability.

Aging stability (%)=(Electric power after kept at aging condition(2.5 mA/cm²)/Electric power before kept at aging condition(2.5 mA/cm²))× 100

The obtained results are shown below.

| Organic EL element | Electron transport material | Aging stability (%) | Remarks |
| --- | --- | --- | --- |
| 2-1 | Electron transport compound 2 | 136 | Comparative example |
| 2-2 | 41 | 121 | Present invention |
| 2-3 | 40 | 116 | Present invention |
| 2-4 | 36 | 110 | Present invention |

From the results described above, it is clear that increase of voltage after aging was suppressed for Organic EL elements of the present invention, and Organic EL elements of the present invention were excellent in aging stability (storage property) compared with a comparative organic EL element.

Example 3

Preparation of Organic EL Element 3-1

An anode was prepared by making patterning to a glass substrate of 100 mm×100 mm×1.1 mm (NA45 produced by NH Techno Glass Corp.) on which a 100 nm film of ITO (indium tin oxide) was formed. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

On the transparent support substrate thus prepared was applied a 70% solution of poly(3,4-ethylenedioxythiphene)-polystyrene sulfonate (PEDOT/PSS, Baytron P Al 4083 made by Bayer AG.) diluted with water by using a spin coating method at 3,000 rpm for 30 seconds to form a film and then it was dried at 200° C. for one hour. A hole transport layer having a thickness of 20 nm was prepared.

The resulting transparent support substrate was fixed to the substrate holder of a commercial vacuum deposition apparatus. Separately, 200 mg of Hole transport material 2 (NPD) was placed in a molybdenum resistance heating boat, 200 mg of Host-30 as a host compound was placed in another molybdenum resistance heating boat, D-26 was placed in further another molybdenum resistance heating boat, Electron transport compound 3 was placed in yet another molybdenum resistance heating boat, and the resulting boats were fitted in the vacuum deposition apparatus.

Subsequently, after reducing the pressure of the vacuum tank to $4 \times 10^{-4}$ Pa, the aforesaid heating boat, in which Hole transport compound 2 was placed, was heated via application of electric current and deposition was carried out onto the transparent support substrate at a deposition rate of 0.1 nm/second, whereby a hole transport layer 2 was arranged.

Further, the aforesaid heating boats each respectively containing Host-30 and D-26 were heated via application of electric current and co-deposition was carried out onto the aforesaid hole transport layer 2 at a respective deposition rate of 0.2 nm/second and 0.012 nm/second, whereby a light emitting layer was arranged.

Here, the temperature of the substrate during the deposition was room temperature. Further, the aforesaid heating boat containing Electron transport compound 3 was heated via application of electric current and deposition was carried out onto the aforesaid light emitting layer at a deposition rate of 0.1 nm/second, whereby an electron transport layer was arranged. Here, the temperature of the substrate during the deposition was room temperature.

Subsequently, 0.5 nm thick potassium fluoride and 110 nm thick aluminium were vapor deposited to form a cathode, whereby Organic EL element 3-1 was prepared.
<<Preparation of Organic EL Elements 3-2 to 3-4>>

Organic EL elements 3-2 to 3-4 were prepared in the same manner as preparation of Organic EL element 3-1, except that Electron transport compound 3 was replaced with the compounds as are listed below.
<<Evaluation of Organic EL Elements 3-1 to 2-4>>

In order to evaluate the obtained organic EL elements 3-1 to 3-4, the same sealing processes was done as done to Organic EL elements 1-1 to 1-4, whereby the lighting device shown in FIGS. 5 and 6 was formed. The organic EL elements were evaluated using the lighting devices.

The following evaluations were made for the obtained Organic EL elements.
(External Quantum Efficiency)

Each organic EL element was allowed to emit a light with a constant electric current of 2.5 mA/cm² at room temperature (at about 23 to 25° C.). The external quantum efficiency ($\eta$) was determined by measuring the luminance (L) (cd/m²) measured immediately after starting to emit light.

Here, the measurement of luminance was done with a spectro radiometric luminance meter CS-1000 (produced by Konica Minolta Sensing Inc.). The external quantum efficiency was represented by the relative value when the external quantum efficiency of Organic EL element 3-1 was set to be 100.
(Emission Lifetime)

Organic EL element was driven with a constant electric current of 2.5 mA/cm² at room temperature (at about 23 to 25° C.) to continuously emit a light. The time required for a decease in one half of the luminance of immediately after the initiation of light emission (being the initial luminance) was determined, and the resulting value was employed as an index of the lifetime in terms of a half lifetime ($\tau_{1/2}$). The emission lifetime was represented as a relative value when the lifetime of Organic EL element 3-1 was set to be 100.

The obtained results are shown in the following.

| Organic EL element | Electron transport material | External quantum efficiency (%) | Emission lifetime | Remarks |
|---|---|---|---|---|
| 3-1 | Electron transport compound 3 | 100 | 100 | Comparative example |
| 3-2 | | 42 | 124 | 330 | Present invention |
| 3-3 | | 43 | 123 | 410 | Present invention |
| 3-4 | | 27 | 127 | 500 | Present invention |

From the results described above, it is clear that Organic EL elements of the present invention had high external quantum efficiency and a long lifetime.

Example 4

Preparation of Organic EL Element 4-1

Organic EL elements 4-1 was prepared in the same manner as preparation of Organic EL element 1-1, except that Hole transport material 1 was replaced with a mixture of 5 mg of Hole transport compound 3 and 45 mg of Hole transport compound 4 dissolved in 10 ml of toluene; and Host-24 was replaced with Host-25; D-1 was replaced with D-30; and Electron transport compound 1 was replaced with BCP.
<<Preparation of Organic EL Elements 4-2 to 4-5>>

Organic EL elements 4-2 to 4-5 were prepared in the same manner as preparation of Organic EL element 4-1, except that BCP was replaced with the compounds as are listed below.
<<Evaluation of Organic EL Elements 4-1 to 4-5>>

In order to evaluate the obtained organic EL elements 4-1 to 4-5, the same sealing processes was done as done to Organic EL elements 1-1 to 1-4, whereby the lighting device shown in FIGS. 5 and 6 was formed. The organic EL elements were evaluated using the lighting devices.

The following evaluations were made for the obtained Organic EL elements.
(Emission Luminance)

Emission luminance (cd/m²) of each organic EL element was measured when it was allowed to emit a light with a direct-current voltage of 4 V at room temperature (about 23 to 25° C.).
(External Quantum Efficiency)

In the same manner as evaluating Organic EL elements 3-1 to 3-4 in Example 3, external quantum efficiency was determined under the condition of a constant electric current of 2.5 mA/cm².

Here, emission luminance and external quantum efficiency were represented by the relative value when the values of Organic EL element 4-1 were set to be 100.

(Voltage Increasing Ratio)

Organic EL element was driven with a constant electric current of 6 mA/cm². The initial voltage and the voltage after driving 150 hours each were measured. The relative value of the voltage after 150 hour driving with respect to the initial voltage was defined as a voltage increasing ratio.

The obtained results are shown in the following.

| Organic EL element | Electron transport material | External quantum efficiency (%) | Emission lifetime | Voltage increasing ratio | Remarks |
|---|---|---|---|---|---|
| 4-1 | BCP | 100 | 100 | 122 | Comparative example |
| 4-2 | Electron transport compound 4 | 114 | 164 | 120 | Comparative example |
| 4-3 | | 44 | 127 | 365 | 114 | Present invention |
| 4-4 | | 38 | 129 | 410 | 112 | Present invention |
| 4-5 | | 29' | 138 | 555 | 111 | Present invention |

From the results described above, it is clear that Organic EL elements of the present invention had high external quantum efficiency, a long lifetime and a small voltage increasing ratio.

Example 5

Preparation of Organic EL Element 5-1

Organic EL elements 5-1 was prepared in the same manner as preparation of Organic EL element 1-1, except that Host-24 was replaced with Host-9; D-1 was replaced with D-24; Electron transport compound 1 was replaced with Electron transport compound 5; and sodium fluoride was replaced with lithium fluoride.

<<Preparation of Organic EL Elements 5-2 to 5-5>>

Organic EL elements 5-2 to 5-5 each were prepared in the same manner as preparation of Organic EL element 5-1, except that lithium fluoride and Electron transport compound were replaced with a combination of the compounds as listed below.

<<Evaluation of Organic EL Elements 5-1 to 5-5>>

In order to evaluate the obtained organic EL elements 4-1 to 4-5, the same sealing processes was done as done to Organic EL elements 1-1 to 1-4, whereby the lighting device shown in FIGS. 5 and 6 was formed. The organic EL elements were evaluated using the lighting devices.

The obtained Organic EL elements were evaluated in the same manner as evaluating Organic EL elements 3-1 to 3-4 in Example 3. External quantum efficiency and Voltage were determined under the condition of a constant electric current of 2.5 mA/cm².

Here, evaluation values were represented by the relative value when the results of Organic EL element 5-1 were set to be 100.

| Organic EL element | Electron transport material | Electron injection layers | External quantum efficiency (%) | Voltage increasing ratio | Remarks |
|---|---|---|---|---|---|
| 5-1 | Electron transport compound 5 | LiF | 100 | 100 | Comparative example |
| 5-2 | 46 | LiF | 110 | 86 | Comparative example |
| 5-3 | Electron transport compound 5 | KF | 105 | 62 | Comparative example |
| 5-4 | 46 | KF | 117 | 45 | Present invention |
| 5-5 | 2 | KF | 119 | 43 | Present invention |

Here, a standard electrode potential of a metal element composing LiF and KF, which were used for forming the above-described electron injection layers are shown in the following.

Li: −3.045 (V) (Comparative example)
K: −2.925 (V) (Present invention)

From the results described above, it is clear that Organic EL elements of the present invention had high external quantum efficiency, and a small voltage increasing ratio compared with comparative elements.

Example 6

Preparation of Organic EL Element 6-1

Organic EL elements 6-1 was prepared in the same manner as preparation of Organic EL element 3-1, except that Host-30 was replaced with Host-25; D-26 was replaced with D-9; and Electron transport compound 3 was replaced with Electron transport compound 6.

<<Preparation of Organic EL Elements 6-2 to 6-4>>

Organic EL elements 6-2 to 6-4 were prepared in the same manner as preparation of Organic EL element 6-1, except that D-9 and Electron transport compound 6 were replaced with a combination of the compounds as listed below.

<<Evaluation of Organic EL Elements 6-1 to 6-4>>

In order to evaluate the obtained organic EL elements 6-1 to 6-4, the same sealing processes was done as done to Organic EL elements 1-1 to 1-4, whereby the lighting device shown in FIGS. 5 and 6 was formed. The organic EL elements were evaluated using the lighting devices.

The obtained Organic EL elements 6-1 to 6-4 were evaluated in the same manner as evaluating Organic EL elements 3-1 to 3-4 in Example 3. External quantum efficiency and Emission lifetime were determined under the condition of a constant electric current of 2.5 mA/cm².

Moreover, the Organic EL elements were visually evaluated by observing the luminescent color at the time of performing continuous luminescence under the constant current conditions of 2.5 mA/cm². Evaluation values were represented by the relative value when the results of Organic EL element 6-1 were set to be 100.

The obtained results are shown in the following.

| Organic EL element | Dopant | Electron transport material | External quantum efficiency (%) | Emission lifetime | Luminescent color | Remarks |
|---|---|---|---|---|---|---|
| 6-1 | D-9 | Electron transport compound 6 | 100 | 100 | Blue | Comparative example |

-continued

| Organic EL element | Dopant | Electron transport material | External quantum efficiency (%) | Emission lifetime | Luminescent color | Remarks |
|---|---|---|---|---|---|---|
| 6-2 | D-9 | 24 | 109 | 150 | Blue | Present invention |
| 6-3 | D-24 | 24 | 113 | 680 | Blue | Present invention |
| 6-4 | D-26 | 24 | 123 | 4500 | Blue | Present invention |

From the results described above, it was found that Organic EL elements of the present invention had high external quantum efficiency and a long lifetime compared with comparative elements.

Example 7

Preparation of Organic EL Element 7-1

Organic EL elements 7-1 was prepared in the same manner as preparation of Organic EL element 1-1, except that Host-24 was replaced with Host-15; D-1 was replaced with D-10; and Electron transport compound 1 was replaced with Electron transport compound 4.

<<Preparation of Organic EL Elements 7-2 and 7-3>>

Organic EL elements 7-2 and 7-3 were prepared in the same manner as preparation of Organic EL element 7-1, except that a host compound and an electron transport compound were replaced with a combination of the compounds as listed below.

<<Evaluation of Organic EL Elements 7-1 to 7-3>>

In order to evaluate the obtained organic EL elements 7-1 to 7-3, the same sealing processes was done as done to Organic EL elements 1-1 to 1-4, whereby the lighting device shown in FIGS. 5 and 6 was formed. The organic EL elements were evaluated using the lighting devices.

The obtained Organic EL elements were evaluated in the same manner as evaluating Organic EL elements 3-1 to 3-4 in Example 3. External quantum efficiency and Emission lifetime were determined under the condition of a constant electric current of 2.5 mA/cm$^2$.

Here, evaluation values were represented by the relative value when the results of Organic EL element 7-1 were set to be 100.

The obtained results are shown in the following.

| Organic EL element | Host compound | Electron transport material | External quantum efficiency (%) | Emission lifetime | Remarks |
|---|---|---|---|---|---|
| 7-1 | Host-15 | Electron transport compound 4 | 100 | 100 | Comparative example |
| 7-2 | Host-15 | 37 | 130 | 350 | Present invention |
| 7-3 | Host-16 | 37 | 134 | 720 | Present invention |

From the results described above, it was found that Organic EL elements of the present invention had high external quantum efficiency and a long lifetime compared with comparative elements.

Example 8

Preparation of Full Color Organic EL Display Device

FIGS. 7a to 7e are a schematic structural drawing of a full color organic EL display device. An anode was prepared by making patterning to glass substrate 201 of 100 mm×100 mm×1.1 mm (NA45 produced by NH Techno Glass Corp.) on which 100 nm film of TTO transparent electrode (202) was formed. Thereafter, there were provided dividing walls 203 (20 μm of width, and 2.0 μm of thickness) made of non-photosensitive polyimide between ITO transparent electrodes prepared on the glass substrate via a photolithography.

Between the polyimide dividing walls on the ITO transparent electrodes was injected the following hole injection layer composition through an ink-jet head (MJ800C, made by Epson Co., Ltd.). Then, injected composition was irradiating with UV rays for 200 seconds and subjected to drying process at 60° C. for 10 minutes. Thus, hole injection layer 204 having a thickness of 40 nm was prepared.

On this hole injection layer were injected the following blue light emitting layer composition, green light emitting layer composition and red light emitting layer composition through the ink-jet head as described above. Then, injected compositions were subjected to drying process at 60° C. for 10 minutes. Thus, light emitting layers (205B, 205G and 205R) each were formed. Next, 20 nm of Example compound 25 was vacuum vapor-deposited upwards so that the light emission layer might be covered, and also 0.6 nm of lithium fluoride and further 130 nm of Al (206) were vacuum deposited to make a cathode. Thus, the targeted organic EL element was produced.

It was found that the produced organic EL element showed luminescence of blue, green, and red respectively, and can be used as a full color display device by impressing voltage to each electrode.

| (Hole injection layer composition) | |
|---|---|
| Hole transport compound 5 | 20 mass parts |
| Cyclohexylbenzene | 50 mass parts |
| Isopropylbiphenyl | 50 mass parts |
| (Blue light emitting layer composition) | |
| Host-9 | 0.7 mass parts |
| D-26 | 0.04 mass parts |
| Cyclohexylbenzene | 50 mass parts |
| Isopropylbiphenyl | 50 mass parts |
| (Green light emitting layer composition) | |
| Host-9 | 0.7 mass parts |
| D-1 | 0.04 mass parts |
| Cyclohexylbenzene | 50 mass parts |
| Isopropylbiphenyl | 50 mass parts |
| (Red light emitting layer composition) | |
| Host-9 | 0.7 mass parts |
| D-10 | 0.04 mass parts |
| Cyclohexylbenzene | 50 mass parts |
| Isopropylbiphenyl | 50 mass parts |

Example 9

Preparation of White Light Emitting Organic EL Element 9-1

An anode was prepared by making patterning to a glass substrate of 100 mm×100 mm×1.1 mm (NA45 produced by NH Techno Glass Corp.) on which a 100 nm film of ITO (indium tin oxide) was formed. Thereafter, the above transparent support substrate provided with the ITO transparent electrode was subjected to ultrasonic washing with isopropyl alcohol, followed by drying with desicated nitrogen gas, and was subjected to UV ozone washing for 5 minutes.

On the transparent support substrate thus prepared was applied a 70% solution of poly(3,4-ethylenedioxythiphene)-polystyrene sulfonate (PEDOT/PSS, Baytron P Al 4083 made by Bayer AG.) diluted with water by using a spin coating method at 3,000 rpm for 30 seconds to form a film and then it was dried at 200° C. for one hour. A $1^{st}$ hole transport layer having a thickness of 30 nm was prepared.

The aforesaid substrate was transferred under an atmosphere of nitrogen, and a solution containing 50 mg of Hole transport compound 6 dissolved in 10 ml of toluene was applied on the aforesaid $1^{st}$ hole transport layer by using a spin coating method at 1,000 rpm for 30 seconds to form a film. The film was irradiated with UV rays for 180 seconds so as to achieve photopolymerization and cross-linking. Then it was subjected to a vacuum drying at 60° C. for one hour to obtain a $2^{nd}$ hole transport layer.

Next, it was applied a solution containing 60 mg of Host-25, 3.0 mg of D-6, and 3.0 mg of D-24 dissolved in 6 ml of toluene by using a spin coating method at 1,000 rpm for 30 seconds to form a film. The film was subjected to a vacuum drying at 60° C. for one hour to obtain a light emitting layer.

Further, one the light emitting layer was applied a solution containing 30 mg of Example compound 3 dissolved in 5 ml of hexafluoroisopropanol (HFIP) by using a spin coating method at 1,500 rpm for 30 seconds to form a film. The film was subjected to a vacuum drying at 60° C. for one hour to obtain an electron transport layer.

Subsequently, the substrate was fixed to the substrate holder of the vacuum deposition apparatus, and 200 mg of Alq$_3$ was placed in a molybdenum resistance heating boat and was fixed to the vacuum deposition apparatus. After the pressure of the vacuum tank was reduced to $4 \times 10^{-4}$ Pa, the aforesaid heating boat including Alq$_3$ was heated via application of electric current and deposition was carried out onto the aforesaid $1^{st}$ electron transport layer at an evaporation rate of 0.1 nm/second, whereby a 40 nm thick $2^{nd}$ electron transport layer was further arranged.

Here, the temperature of the substrate during the deposition was room temperature (23 C.° to 25 C.°).

Subsequently, 0.5 nm thick potassium fluoride was deposited, then 110 nm thick aluminum was deposited to form a cathode, whereby Organic EL element 9-1 was prepared.

When this prepared Organic EL element was electrified the almost white light was obtained, and it was revealed that this organic EL element can be used as a lighting devise. In addition, even if the used compounds were replaced with other example compounds of the present invention, it was found that white luminescence was obtained similarly.

DESCRIPTION OF SYMBOLS

1: display
3: pixel
5: scanning line
6: data line
7: electric source line
10: organic EL element
11: switching transistor
12: operating transistor
13: capacitor
A: display section
B: control diction
101: organic EL element
102: glass cover
105: cathode
106: organic EL layer
107: glass substrate having a transparent electrode
108: nitrogen gas
109: water catching agent
201: glass substrate
202: ITO transparent electrode
203: dividing wall
204: hole injection layer
205B, 205G and 205R: light emitting layer

The invention claimed is:

1. An organic electroluminescence element comprising an anode, a cathode and a plurality of composing layers including a light emitting layer sandwiched between the anode and the cathode, wherein an electron transport layer containing a compound represented by any one of Formulas (2) to (4) is included in the composing layers; the light emitting layer contains a phosphorescence emitting organic metal complex; and the cathode or one composing layer adjacent to the cathode contains a metal or a metal compound belonging to Group 1 or Group 2 of the periodic table of elements, provided that the metal exhibits a standard electrode potential larger than −3 V vs. SHE in a system of the metal ion ($M^{n+}$)/the metal (M):

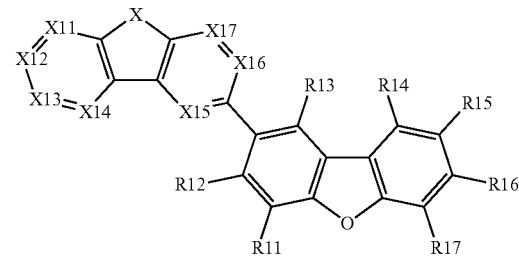

Formula (2)

wherein R11 to R17 each represent a hydrogen atom or a substituent; X represents —S—; and X11 to X17 represents —C(R18)=, or —N=, R18 represents a hydrogen atom or a substituent, and when a plurality of —C(R18)= exists, the plurality of R18s may be the same or different, provided that at least one of R11 to R18 represents a benzene ring having a substituent of an aromatic hydrocarbon ring group or an aromatic heterocyclic group;

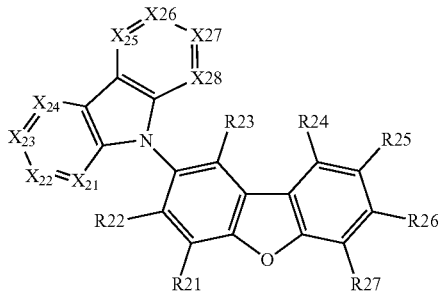

Formula (3)

wherein R21 to R27 each represent a hydrogen atom or a substituent; X21 to X23, and X26 to X28 each represent —C(R28)=, or —N=; X24 and X25 each represent —C(R28)=, provided that at least one of X21 to X23, and X26 to X28 represents —N=, R28 represents a hydrogen atom or a substituent, and when a plurality of —C(R28)= exists, the plurality of R28s may be the same or different, provided that at least one of R28s represents a substituent selected from the group consisting of a pyridyl group, a pyrimidinyl group, a pyradinyl group, a pyridazinyl group, and a triazinyl group; and

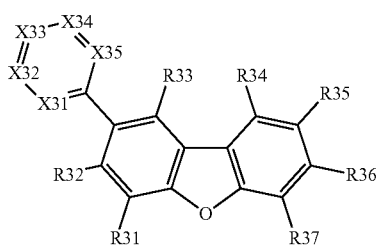

Formula (4)

wherein R31 to R37 each represent a hydrogen atom or a substituent; X31 to X35 each represent —C(R38)=, or —N=, provided that at least one of X31 to X32 represents —N=, and R38 represents a hydrogen atom or a substituent, and at least one of X31 to X35 represents —C(R38)= in which R38 represents an aromatic heterocyclic group, and when a plurality of —C(R38)= exists, the plurality of R38s may be the same or different.

2. The organic electroluminescence element of claim 1, wherein in Formula (2), R11 to R14, R16, and R17 each represent a hydrogen atom; and X11, X12 and X14 to X17 each represent —CH=.

3. The organic electroluminescence element of claim 1, wherein X21, X22, X27 and X28 in Formula (3) each represent —CH=, or —N=.

4. The organic electroluminescence element of claim 1, wherein R31 to R34, R36 and R37 in Formula (4) each represent a hydrogen atom; and X33 represents —CH=, or —N=.

5. The organic electroluminescence element of claim 1, wherein the compound represented by any one of Formulas (2) to (4) contains as a partial structure at least one pyridine ring or one condensed aromatic heterocycle containing a pyridine ring.

6. The organic electroluminescence element of claim 1, wherein the metal element is sodium, potassium or cesium.

7. The organic electroluminescence element of claim 1, wherein the phosphorescence emitting organic metal complex is a compound represented by Formula (5):

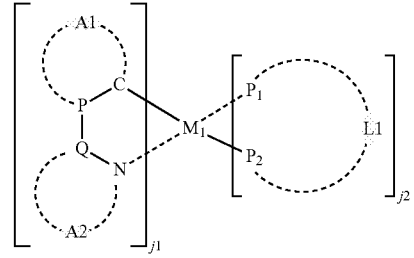

Formula (5)

wherein P and Q each represent a carbon atom or a nitrogen atom; A1 represents a group of atoms necessary to form an aromatic hydrocarbon ring or an aromatic heterocycle together with P—C; A2 represents a group of atoms necessary to form an aromatic heterocycle together with Q-N; $P_1$-L1-$P_2$ represents a bidentate ligand, $P_1$ and $P_2$ each independently represent a carbon atom, a nitrogen atom, or an oxygen atom, and L1 represents a group of atoms necessary to form a bidentate ligand together with $P_1$ and $P_2$; j1 is an integer of 1 to 3, and j2 is an integer of 0 to 2, provided that the sum of j1 and j2 is 2 or 3; $M_1$ represents a metal element of Group 8 to Group 10 in the periodic table.

8. The organic electroluminescence element of claim 7, wherein the compound represented by Formula (5) is a compound represented by Formula (6):

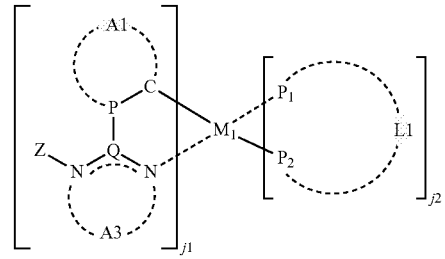

Formula (6)

wherein Z represents a hydrocarbon ring group or a heterocyclic group; P and Q each represent a carbon atom or a nitrogen atom; A1 represents a group of atoms necessary to form an aromatic hydrocarbon ring or an aromatic heterocycle together with P—C; A3 represents —C($R_{01}$)=C($R_{02}$)—, —N=C($R_{02}$)—, —C($R_{01}$)=N—, or —N=N—, and $R_{01}$ and $R_{02}$ each represent a hydrogen atom or a substituent; $P_1$-L1-$P_2$ represents a bidentate ligand, $P_1$ and $P_2$ each independently represent a carbon atom, a nitrogen atom, or an oxygen atom, and L1 represents a group of atoms necessary to form a bidentate ligand together with $P_1$ and $P_2$; j1 is an integer of 1 to 3, and j2 is an integer of 0 to 2, provided that the sum of j1 and j2 is 2 or 3; and $M_1$ represents a transition metal element of Group 8 to Group 10 in the periodic table.

9. The organic electroluminescence element of claim 8, wherein the compound represented by Formula (6) is a compound represented by Formula (7):

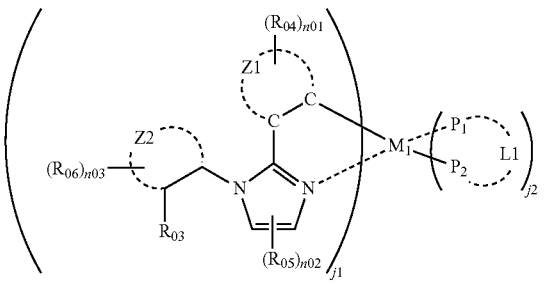

Formula (7)

wherein $R_{03}$ represents a substituent; $R_{04}$ represents a hydrogen atom or a substituent, and a plurality of $R_{04}$s may be joined together to form a ring, n01 is an integer of 1 to 4; $R_{05}$ represents a hydrogen atom or a substituent, and a plurality of $R_{05}$s may be joined together to form a ring, n02 is an integer of 1 to 2; $R_{06}$ represents a hydrogen atom or a substituent, and a plurality of $R_{06}$s may be joined together to form a ring, n03 is an integer of 1 to 4; Z1 represents a group of atoms necessary to form a 6-membered aromatic hydrocarbon ring, or a 5 or 6-membered aromatic heterocycle together with C—C; Z2 represents a group of atoms necessary to form a hydrocarbon ring or a heterocycle; $P_1$-L1-$P_2$ represents a bidentate ligand, $P_1$ and $P_2$ each independently represent a carbon atom, a nitrogen atom, or an oxygen atom, and L1 represents a group of atoms necessary to form a bidentate ligand together with $P_1$ and $P_2$; j1 is an integer of 1 to 3, and j2 is an integer of 0 to 2, provided that the sum of j1 and j2 is 2 or 3; $M_1$ represents a transition metal element of Group 8 to Group 10 in the periodic table; and $R_{03}$ and $R_{06}$, $R_{04}$ and $R_{06}$, and $R_{05}$ and $R_{06}$ may be joined together to form a ring.

10. The organic electroluminescence element of claim 9, wherein the compound represented by Formula (7) is a compound represented by Formula (8):

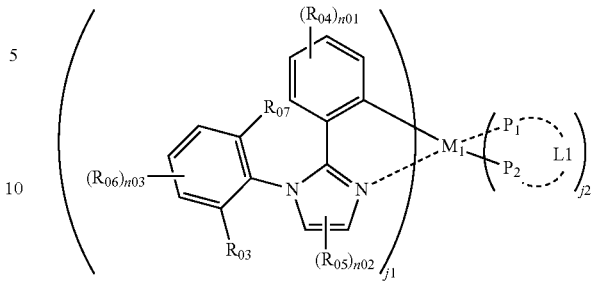

Formula (8)

wherein $R_{03}$ represents a substituent; $R_{04}$ represents a hydrogen atom or a substituent, and a plurality of $R_{04}$s may be joined together to form a ring, n01 is an integer of 1 to 4; $R_{05}$ represents a hydrogen atom or a substituent, and a plurality of $R_{05}$s may be joined together to form a ring, n02 is an integer of 1 to 2; $R_{06}$ represents a hydrogen atom or a substituent, and a plurality of $R_{06}$s may be joined together to form a ring, n03 is an integer of 1 to 3; $R_{07}$ represents a substituent or a single bond; $P_1$-L1-$P_2$ represents a bidentate ligand, $P_1$ and $P_2$ each independently represent a carbon atom, a nitrogen atom, or an oxygen atom, L1 represents a group of atoms necessary to form a bidentate ligand together with $P_1$ and $P_2$; j1 is an integer of 1 to 3, and j2 is an integer of 0 to 2, provided that the sum of j1 and j2 is 2 or 3; and $M_1$ represents a transition metal element of Group 8 to Group 10 in the periodic table.

11. The organic electroluminescence element of claim 7, wherein $M_1$ represents iridium.

12. The organic electroluminescence element of claim 1, wherein at least two organic layers including the electron transport layer and the light emitting layer are formed with a wet method.

13. The organic electroluminescence element of claim 1, wherein the organic electroluminescence element emits a white light.

14. A lighting device comprising the organic electroluminescence element of claim 1.

15. A display device comprising the organic electroluminescence element of claim 1.

16. The organic electroluminescence element of claim 1, wherein at least one of R11 to R18 in Formula (2) represents a benzene ring having a substituent selected from the group consisting of a pyridyl group, a pyrimidinyl group, a pyrrolyl group, an imidazolyl group, a benzoimidazolyl group, a pyrazolyl group, a pyradinyl group, a triazolyl group, an oxazolyl group, a benzoxazolyl group, a thiazolyl group, an isooxazolyl group, an isothiazolyl group, a furazanyl group, an indolyl group, a carbazolyl group, a carbolinyl group, a diazacarbazolyl group, a quinoxalinyl group, a pyridazinyl group, a triazinyl group, a quinazolinyl group, and a phthalazinyl group.

* * * * *